(12) United States Patent
Rogers et al.

(10) Patent No.: US 7,541,096 B2
(45) Date of Patent: Jun. 2, 2009

(54) ELECTROLUMINESCENT DEVICE

(75) Inventors: Jonathan Rogers, White Plains, NY (US); Anthony David DeBellis, Stony Point, NY (US); Stephen Daniel Pastor, Mayhill, NM (US); Norihisa Dan, Yawata (JP); François Maike, Geispitzen (FR)

(73) Assignee: Ciba Specialty Chemicals Corporation, Tarrytown, NY (US)

(*) Notice: Subject to any disclaimer, the term of this patent is extended or adjusted under 35 U.S.C. 154(b) by 294 days.

(21) Appl. No.: 10/517,411

(22) PCT Filed: May 30, 2003

(86) PCT No.: PCT/EP03/05698

§ 371 (c)(1),
(2), (4) Date: Dec. 3, 2004

(87) PCT Pub. No.: WO03/105538

PCT Pub. Date: Dec. 18, 2003

(65) Prior Publication Data

US 2005/0175856 A1    Aug. 11, 2005

Related U.S. Application Data

(60) Provisional application No. 60/386,306, filed on Jun. 6, 2002.

(51) Int. Cl.
*H01J 1/62* (2006.01)
*C09K 11/06* (2006.01)

(52) U.S. Cl. .......... 428/690; 428/917; 252/301.16; 252/301.27; 313/504; 313/506

(58) Field of Classification Search ........ 428/690, 428/917; 313/504, 506; 252/301.16, 301.27; 257/40, 89, 90, 102, 103
See application file for complete search history.

(56) References Cited

U.S. PATENT DOCUMENTS

| | | | |
|---|---|---|---|
| 2,713,056 A | 7/1955 | Sartori | 260/304 |
| 2,784,183 A | 3/1957 | Keller et al. | 260/240 |
| 2,784,197 A | 3/1957 | Zweidler et al. | 260/308 |
| 3,288,786 A | 11/1966 | Strobel et al. | 260/240 |
| 3,341,530 A | 9/1967 | Strobel et al. | 260/240 |
| 3,793,315 A | 2/1974 | Siegrist | 260/240 |
| 4,533,612 A | 8/1985 | Eilingsfeld et al. | 430/59 |
| 5,006,662 A | 4/1991 | Lund et al. | 548/260 |
| 5,104,740 A | 4/1992 | Shinkai et al. | 428/457 |
| 5,116,708 A | 5/1992 | Shikatani et al. | 430/59 |
| 5,486,406 A | 1/1996 | Shi | 428/209 |
| 5,518,824 A | 5/1996 | Funhoff et al. | 428/690 |
| 5,629,389 A | 5/1997 | Roitman et al. | 525/534 |
| 5,779,937 A * | 7/1998 | Sano et al. | 252/301.16 |
| 6,280,859 B1 | 8/2001 | Onikubo et al. | 428/690 |
| 6,962,755 B2 * | 11/2005 | Ise et al. | 428/690 |

FOREIGN PATENT DOCUMENTS

| | | |
|---|---|---|
| CA | 2185878 | 3/1997 |
| EP | 0418385 | 3/1991 |
| EP | 0764712 | 3/1997 |
| EP | 0866110 | 9/1998 |
| GB | 1150408 | 4/1969 |
| GB | 1269004 | 3/1972 |
| JP | 98140145 | 5/1998 |
| JP | 00256667 | 9/2000 |
| WO | 03/105538 | 12/2003 |

OTHER PUBLICATIONS

Beilstein Registry No. 286124 for Chmatal et al., Collect. Czech. Chem. Commun., vol. 24, (1959), pp. 494, 499.
Beilstein Registry No. 310010 for Charrier et al, Gazz. Chim. Ital., vol. 57, (1927), p. 753.
Beilstein Registry No. 557484 for Garmatter et al., Helv. Chim. Acta., vol. 57, (1974), pp. 945-979.
Beilstein Registry No. 167844 for Elbs, J. Prakt. Chem., vol. 108, (1924), p. 223.
Beilstein Registry No. 146520 for Fries et al., Justus Liebigs Ann. Chem., vol. 511, (1934), pp. 213, 240.
Beilstein Registry No. 28432 for Willgerodt et al., J. Prakt. Chem., vol. 71, (1905), p. 396.
Beilstein Registry No. 205560 for Krollpfeiffer et al., Justus Liebigs Ann. Chem., vol. 515, (1935), p. 119.
Beilstein Registry No. 167842 for Zanirato, J. Chem. Soc. Chem. Commun., vol. 19, (1983), pp. 1065-1067.
Beilstein Registry No. 25415 for Joshi et al, J. Indian Chem. Soc., vol. 35, (1958), pp. 681, 682, 685.
Beilstein Registry No. 20521 for Charrier, Gazz. Chim. Ital., vol. 40, (1910), p. 138.
Beilstein Registry No. 13989 for Poskocil et al., Collect. Czech. Chem. Commun., vol. 22, (1957), pp. 548, 555.
Beilstein Registry No. 7652458 for Butler et al., J. Chem. Soc. Perkin Trans. 1, (1997), pp. 1047-1050.
Beilstein Registry No. 8506620 for Katritzky et al., Heterocycles, vol. 52, No. 1, (2000), pp. 203-214.
Beilstein Registry No. 554478 for Iwamoto et al., Yuki Gosei Kagaku Kyokaishi, vol. 23, (1965) p. 51.
P. López-Alvarado et al., J. Org. Chem., (1995), vol. 60, pp. 5678-5682.
Yasuda, J. Heterocyclic Chem., vol. 35, pp. 365-369, (1998).
Patent Abstracts of Japan Publication No. 11040355, (1999).
Tsutsui et al., Synthetic Metals, vol. 85, (1997), pp. 1201-1204.
English language abstract for JP 58009151 (1983).
G. Woessner et al., J. Phys. Chem. (1985), vol. 89, pp. 3629-3636.
Chem. Abstract 55:51370 for DE 1052405 (1959).

* cited by examiner

*Primary Examiner*—D. Lawrence Tarazano
*Assistant Examiner*—Camie S Thompson
(74) *Attorney, Agent, or Firm*—Shiela A. Loggins

(57) ABSTRACT

Disclosed are electroluminescent devices that comprise organic layers that contain certain 2H-benzotriazole compounds. The 2H-benzotriazole compounds of blue-emitting, durable, organo-electroluminescent layers. The electroluminescent devices may be employed for full color display panels in for example mobile phones, televisions and personal computer screens.

7 Claims, No Drawings

ELECTROLUMINESCENT DEVICE

This application is a national stage of international application PCT/EP03/05698, filed May 30, 2003, which application claims benefit under 35 USC 119(e) of U.S. provisional application No. 60/386,306, filed Jun. 6, 2002.

The present invention relates to organo-electroluminescent (EL) devices, in particular EL devices that comprise durable, blue-emitting organo-electroluminescent layers. The organo-electroluminescent layers comprise certain 2H-benzotriazoles.

Progress has been made towards developing organic-based electroluminescent devices suitable for full color displays. Generally, an EL device is comprised of a light-emitting layer or layers and a pair of facing electrodes sandwiching the light-emitting layer(s). Application of an electric field between the electrodes results in the injection of electrons and holes to the system, resulting in the release of energy as light.

However, organo EL devices have not been developed that have suitable stability under continuous operation. In particular, there remains a need for blue-emitting, stable organo EL devices.

U.S. Pat. No. 5,104,740 teaches an electroluminescent element that comprises a fluorescent layer containing a coumarinic or azacoumarinic derivative and a hole transport layer, both made of organic compounds and laminated on top of the other. Certain of the coumarinic compounds disclosed have 2H-benzotriazole substitutents.

U.S. Pat. No. 6,280,859 discloses certain polyaromatic organic compounds for use as a light-emitting material in organo-electroluminescent devices. A 2H-benzotriazole moiety is listed among a long list of possible divalent aromatic linking groups.

U.S. Pat. No. 5,116,708 is aimed at a hole transport material for EL devices.

U.S. Pat. No. 5,518,824 teaches an EL device comprising one or more organic layers, wherein at least one of the layers is obtained by thermal or radiation-induce crosslinking. Certain benzotriazoles are disclosed as suitable charge transport compounds.

U.S. Pat. No. 4,533,612 discloses electrophotographic recording materials that comprise certain 2H-benzotriazoles as charge carrier-transporting compounds.

JP 58009151 discloses the use of certain polyaromatic benzotriazole systems in a charge transport layer of an electrophotographic photoreceptor.

U.S. Pat. No. 5,629,389 discloses an electroluminescent device having a layer that comprises 2-(2H-benzotriazole-2-yl)-4,6-bis(1-methyl-1-phenylethyl)phenol.

EP 764712 discloses ortho hydroxyphenyl-2H-benzotriazoles as stabilizers in EL devices. Tsutsui, et al., in *Synthetic Metals*, 1997 (85) 1201-1204, discloses 2-(2-hydroxy-5-methylphenyl)-2H-benzotriazole as a fluorescence quencher in an electron transport layer.

U.S. Pat. Nos. 2,784,183, 2,713,056, 2,784,197, 3,288,786, 3,341,530, 5,006,662, GB-A-1150408, DE-A-1052405, and DE-A-1919181 disclose naphthobenzotriazoles used as optical brighteners.

U.S. Pat. No. 3,793,315 teaches stilbenyl benzotriazole derivatives as optical brighteners. Woessner, et al., in *J. Phys. Chem.*, 1985 (89), 3629-3636 studied the emission of 2-(2-hydroxy-5-methylphenyl)-2H-benzotriazole, and the methoxy analogue thereof.

U.S. Pat. No. 5,486,406 teaches the use of metal complexes of ortho hydroxyphenyl-2H-benzotriazoles in organic light emitting devices.

JP 00256667 and JP 98140145 disclose metal complexes of ortho hydroxyphenyl-2H-benzotriazoles for use in electroluminescent devices.

Certain 2H-benzotriazole derivatives are found to be suitable for use in organo-electroluminescent devices. In particular, certain 2H-benzotriazole derivatives are suitable blue emitters with good durability.

The present invention is aimed at an electroluminescent device comprising an organic light-emitting layer comprising a blue-emitting 2H-benzotriazole compound.

The 2H-benzotriazole compound comprises for example one or more 2H-benzotriazole moieties:

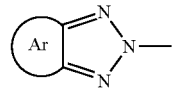

Ar can be any form of an aromatic or heteroaromatic ring (or ring system). That is 2H-benzotriazole compound in the context of the present invention means a 2H-benzotriazole or hetero-2H-benzotriazole because Ar can be any form of an aromatic ring (not only carbons).

Examples that specify the possibilities for the

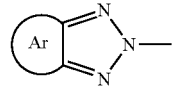

group designated above are as follows:

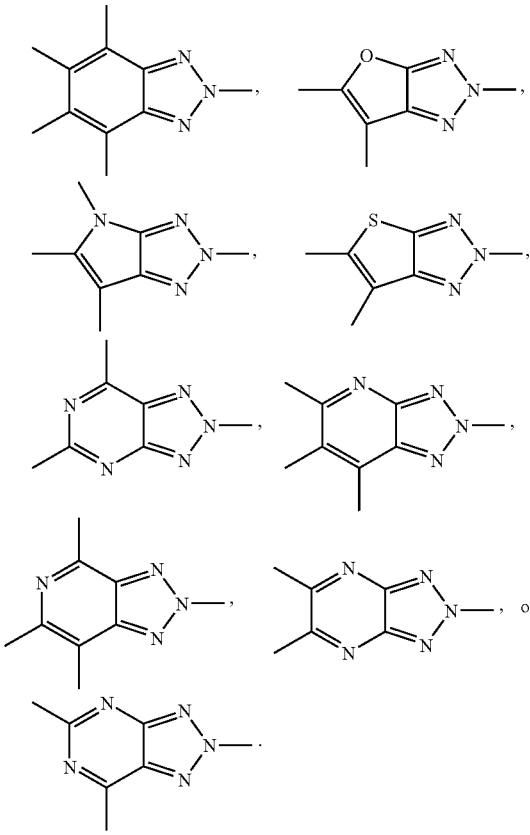

For example, the present 2H-benzotriazole compounds comprise one, two, three or four 2H-benzotriazole moieties. It is understood that the open valences in the 2H-benzotriazole moiety represents a covalent bond that is not limited in its substitution. According to the present invention the EL device comprise at least a 2H-benzotriazole compound, i.e. it may comprise two or more 2H-benzotriazole compounds.

The 2H-benzotriazole compound or compounds should emit light below about 520 nm, especially between about 380 nm and about 520 nm. The 2H-benzotriazole compound or compounds should have a NTSC coordinate of between about (0.12, 0.05) and about (0.16, 0.10), especially a NTSC coordinate of about (0.14, 0.08).

The 2H-benzotriazole compound or compounds should have a melting point above about 150° C., especially above about 200° C., more preferred above about 250° C., most preferred above about 300° C.

Accordingly, the present invention relates to an electroluminescent device (EL device), comprising a 2H-benzotriazole compound, especially a compound of the formula

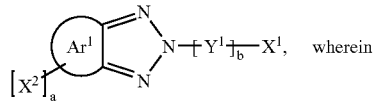  (I)

wherein a is 0, or 1,
b is 0, or 1,
$X^1$ is a group of formula

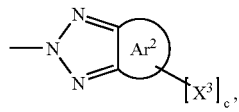

if b is 1, or $Y^3$, if b is 0, wherein
c is 0, or 1,
$X^2$ and $X^3$ are independently of each other a group of formula

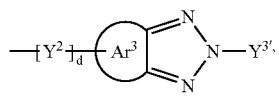

wherein d is 0, or 1,
$Ar^1$, $Ar^2$, and $Ar^3$ are independently of each other aryl or heteroaryl, which can optionally be substituted, especially $C_6$-$C_{30}$aryl or a $C_2$-$C_{26}$heteroaryl, which can optionally be substituted,
$Y^1$ and $Y^2$ are independently of each other a divalent linking group, and
$Y^3$ and $Y^{3'}$ are Independently of each other aryl or heteroaryl, which can optionally be substituted, especially $C_6$-$C_{30}$aryl or a $C_2$-$C_{26}$heteroaryl, which can optionally be substituted.

In more detail, the present invention relates to an electroluminescent device, comprising a 2H-benzotriazole compound of the formula $Ar^1$, $Ar^2$, $Ar^3$, $X^2$, $X^3$, $Y^1$ and $Y^2$ are defined as above,
d is 0, or 1,
$Ar^4$ stand for $C_6$-$C_{30}$aryl or a $C_2$-$C_{26}$heteroaryl, which can optionally be substituted, and
$Y^3$ and $Y^{3'}$ are independently of each other $C_6$-$C_{30}$aryl or a $C_2$-$C_{26}$heteroaryl, which can optionally be substituted.

The groups

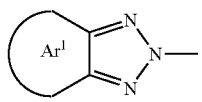 and 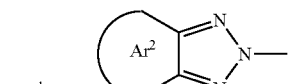

in formula II or III are independently of each other a group of formula

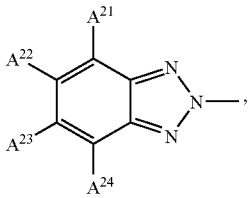

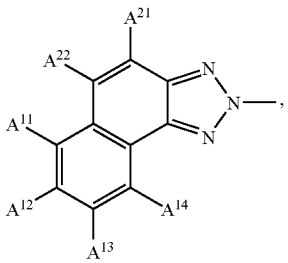

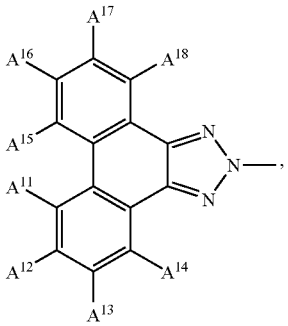 , or

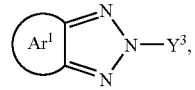 (II)

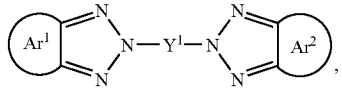 (III)

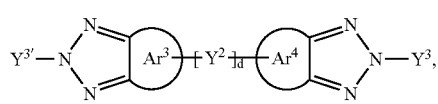 (IV)

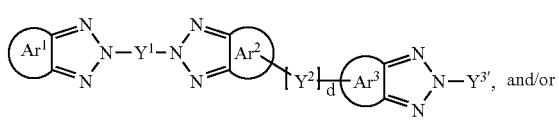 (V)

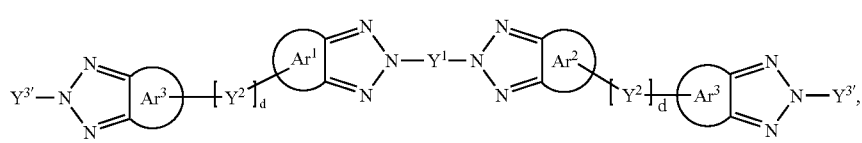 , and/or (VI)

-continued

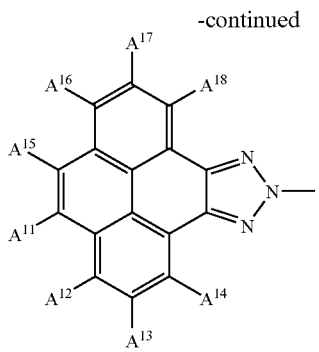

wherein
$A^{21}, A^{22}, A^{23}, A^{24}, A^{11}, A^{12}, A^{13}, A^{14}, A^{15}, A^{17}$ and $A^{18}$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_5$-$C_{12}$cycloalky, $C_5$-$C_{12}$cycloalkyl which is substituted by E and/or interrupted by S—, —O—, or —NR$^{25}$—, —NR$^{25}$R$^{26}$, $C_1$-$C_{24}$alkylthio, —PR$^{32}$R$^{32}$, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by E, $C_7$-$C_{25}$aralkoxy, $C_7$-$C_{25}$aralkoxy which is substituted by E, or —CO—R$^{28}$, or $A^{22}$ and $A^{23}$ or $A^{11}$ and $A^{23}$ are a group

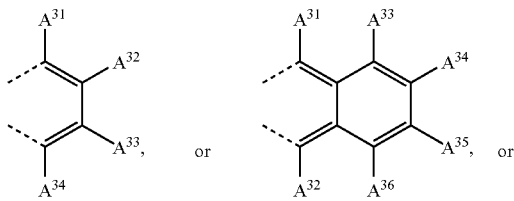

two groups $A^{11}, A^{12}, A^{13}, A^{14}, A^{15}, A^{16}, A^{17}$ and $A^{18}$, which are neighbouring to each other, are a group

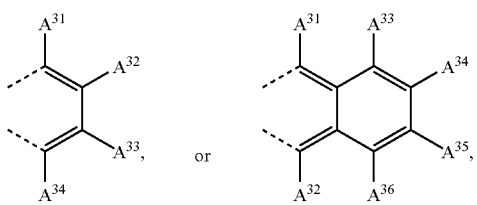

wherein $A^{31}, A^{32}, A^{33}, A^{34}, A^{35}, A^{36}$ and $A^{37}$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_5$-$C_{12}$cycloalkyl, $C_5$-$C_{12}$cycloalkyl which is substituted by E and/or interrupted by S—, —O—, or —NR$^{25}$, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by E, $C_7$-$C_{25}$aralkoxy, $C_7$-$C_{25}$aralkoxy which is substituted by E, or —CO—R$^{26}$, D is —CO—; —COO—; —S—; —SO—; —SO$_2$—; —O—; —NR$^{25}$—; —SiR$^{30}$R$^{31}$—; —POR$^{32}$—; —CR$^{23}$=CR$^{24}$—; or —C≡C—; and E is —OR$^{29}$; —SR$^{29}$; —NR$^{25}$R$^{26}$; —COR$^{26}$; —COOR$^{27}$; —CONR$^{25}$R$^{26}$; —CN; —OCOOR$^{27}$; or halogen; wherein $R^{23}, R^{24}, R^{25}$ and $R^{28}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—; or $R^{25}$ and $R^{26}$ together form a five or six membered ring, in particular

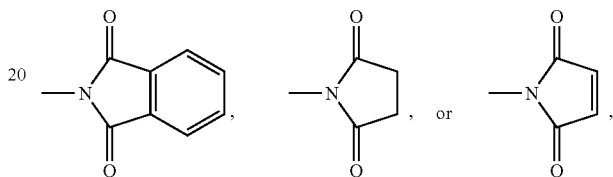

$R^{27}$ and $R^{28}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—, $R^{29}$ is H; $C_6$-$C_{18}$aryl; $C_6$-$C_{18}$aryl, which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—, $R^{30}$ and $R^{31}$ are independently of each other $C_1$-$C_{24}$alkyl, $C_6$-$C_{18}$aryl, or $C_6$-$C_{18}$aryl, which is substituted by $C_1$-$C_{24}$alkyl, and $R^{32}$ is $C_1$-$C_{24}$alkyl, $C_6$-$C_{18}$aryl, or $C_6$-$C_{18}$aryl, which is substituted by $C_1$-$C_{24}$alkyl.

Preferably, the groups

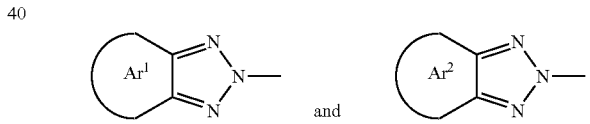

are independently of each other a group of formula

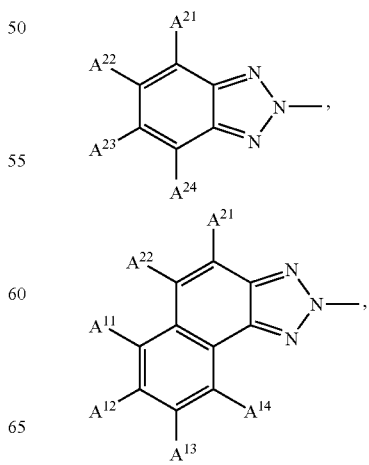

-continued

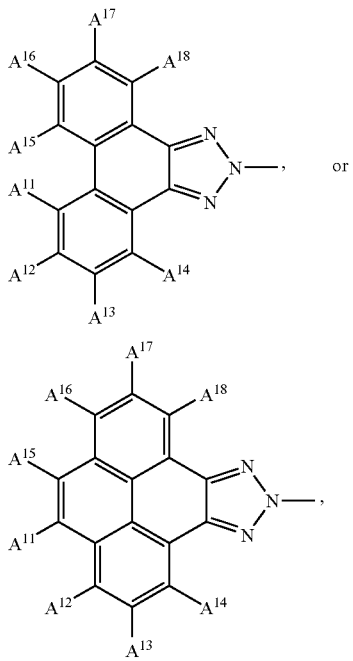

or

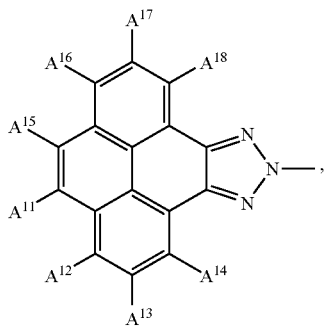

$A^{21}$, $A^{22}$, $A^{23}$ and $A^{24}$ are independently of each other hydrogen, halogen, $C_1$-$C_{24}$alkyl, $C_1$-$C_{24}$perfluoroalkyl, $C_6$-$C_{18}$aryl, —$NR^{25}R^{26}$, —$CONR^{25}R^{26}$, or —$COOR^{27}$, or $C_2$-$C_{10}$heteroaryl, especially a group of formula

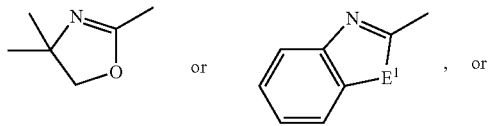

$A^{22}$ and $A^{23}$ are a group of formula

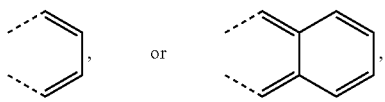

$A^{11}$, $A^{12}$, $A^{13}$, $A^{14}$, $A^{15}$, $A^{16}$, $A^{17}$, and $A^{18}$ are independently of each other H, CN, $C_1$-$C_{24}$alkyl, $C_1$-$C_{24}$alkoxy, $C_1$-$C_{24}$alkylthio, $C_6$-$C_{18}$aryl, —$NR^{25}R^{26}$, —$CONR^{25}R^{26}$, or —$COOR^{27}$, or $C_2$-$C_{10}$heteroaryl, wherein $E^1$ is O, S, or $NR^{25}$, $R^{25}$ and $R^{26}$ are independently of each other H, $C_6$-$C_{18}$aryl, $C_7$-$C_{18}$aralkyl, or $C_1$-$C_{24}$alkyl, $R^{27}$ is $C_1$-$C_{24}$alkyl.

The groups

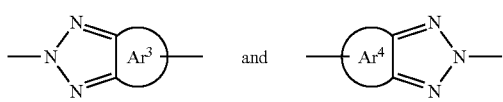

in formula IV are independently of each other a group of formula

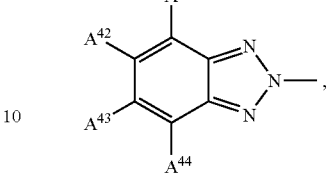

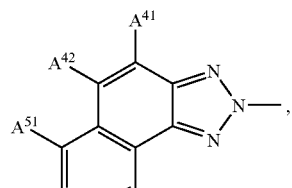

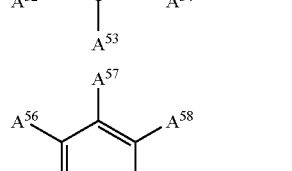

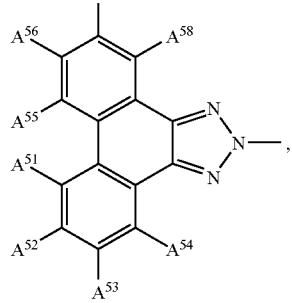

or

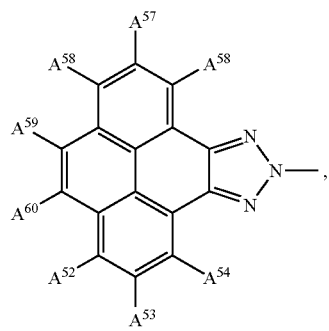

wherein $A^{41}$, $A^{42}$, $A^{43}$, $A^{44}$, $A^{51}$, $A^{52}$, $A^{53}$, $A^{54}$, $A^{55}$, $A^{56}$, $A^{57}$, $A^{58}$, $A^{59}$ and $A^{60}$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_5$-$C_{12}$cycloalkyl, $C_5$-$C_{12}$cycloalkyl which is substituted by E and/or interrupted by S—, —O—, or —$NR^{25}$—, $NR^{25}R^{26}$, $C_1$-$C_{24}$alkylthio, —$PR^{32}R^{32}$, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by E, $C_7$-$C_{25}$aralkoxy, $C_7$-$C_{25}$aralkoxy which is substituted by E, or —CO—$R^{28}$, or $A^{42}$ and $A^{43}$ or $A^{42}$ and $A^{51}$ are a group

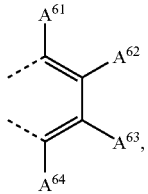 or 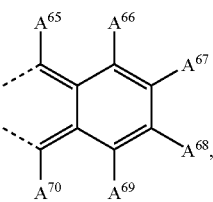

two groups $A^{51}, A^{52}, A^{53}, A^{54}, A^{55}, A^{56}, A^{57}, A^{58}, A^{59}$ and $A^{60}$, which are neighbouring to each other, are a group

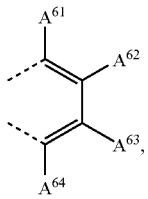 or 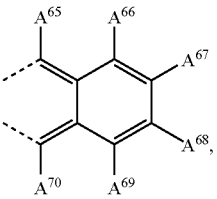

wherein $A^{61}, A^{62}, A^{63}, A^{64}, A^{65}, A^{66}, A^{67}, A^{68}, A^{69}$ and $A^{70}$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_5$-$C_{12}$cycloalkyl, $C_5$-$C_{12}$cycloalkyl which is substituted by E and/or interrupted by S—, —O—, or —$NR^{25}$—, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by E, $C_7$-$C_{25}$aralkoxy, $C_7$-$C_{25}$aralkoxy which is substituted by E, or —CO—$R^{26}$, wherein E, D, $R^{25}$ and $R^{26}$ are defined as above and one of the substituents $A^{41}, A^{42}, A^{43}, A^{44}, A^{51}, A^{52}, A^{53}, A^{54}, A^{55}, A^{56}, A^{57}, A^{58}, A^{59}, A^{60}, A^{61}, A^{62}, A^{63}, A^{64}, A^{65}, A^{66}, Ar^{67}, A^{68}, A^{69}$ and $A^{70}$ represents a single bond, i.e. the linkage to $Y^2$.

Preferably, $A^{43}$ and $A^{43}$ are not a group —$NR^{25}R^{26}$ at the same time.

$Y^3$ and $Y^{3'}$ in formula II, IV and V are independently of each other a group of formula

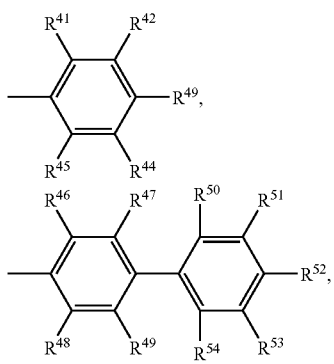

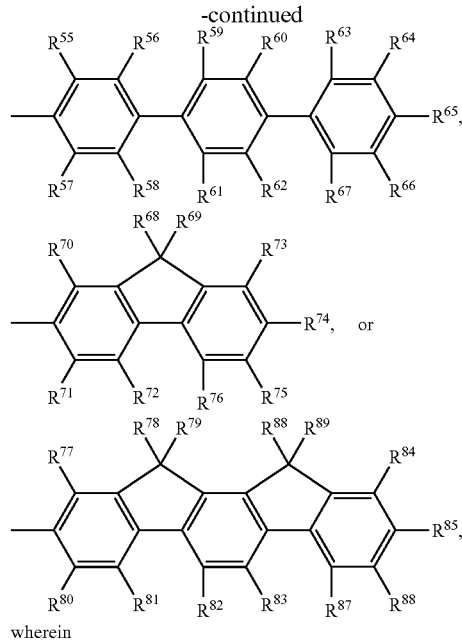

wherein $R^{41}, R^{42}, R^{43}, R^{44}, R^{45}, R^{46}, R^{47}, R^{48}, R^{49}, R^{50}, R^{51}, R^{52}, R^{53}, R^{54}, R^{55}, R^{56}, R^{57}, R^{58}, R^{59}, R^{60}, R^{61}, R^{62}, R^{63}, R^{64}, R^{65}, R^{66}, R^{67}, R^{70}, R^{71}, R^{72}, R^{73}, R^{74}, R^{75}, R^{76}, R^{77}, R^{80}, R^{81}, R^{82}, R^{83}, R^{84}, R^{85}, R^{86}$, and $R^{87}$ are independently of each other H, $C_1$-$C_{24}$alkyl, which is optionally substituted by E and/or interrupted by D, $C_1$-$C_{24}$alkenyl, which is optionally substituted by E, $C_5$-$C_{12}$cycloalkyl, which is optionally substituted by E, $C_5$-$C_{12}$cycloalkoxy, which is optionally substituted by E, $C_6$-$C_{18}$aryl, which is optionally substituted by E, $C_1$-$C_{24}$alkoxy, which is optionally substituted by E and/or interrupted by D, $C_6$-$C_{18}$aryloxy, which is optionally substituted by E, $C_7$-$C_{18}$arylalkoxy, which is optionally substituted by E, $C_1$-$C_{24}$alkylthio, which is optionally substituted by E and/or interrupted by D, $C_1$-$C_{24}$alkylselenium, which is optionally substituted by E and/or Interrupted by D, $C_1$-$C_{24}$alkyltellurium, which is optionally substituted by E and/or interrupted by D, $C_2$-$C_{20}$heteroaryl which is substituted by E, or $C_6$-$C_{18}$aralkyl, which is optionally substituted by E, or two groups $R^{41}, R^{42}, R^{43}, R^{44}, R^{45}, R^{46}, R^{47}, R^{48}, R^{49}, R^{50}, R^{51}, R^{52}, R^{53}, R^{54}, R^{55}, R^{56}, R^{57}, R^{58}, R^{59}, R^{60}, R^{61}, R^{62}, R^{63}, R^{64}, R^{65}, R^{66}, R^{67}, R^{70}, R^{71}, R^{72}, R^{73}, R^{74}, R^{75}, R^{76}, R^{77}, R^{80}, R^{81}, R^{82}, R^{83}, R^{84}, R^{85}, R^{86}$, and $R^{87}$, which are neighbouring to each other, are a group

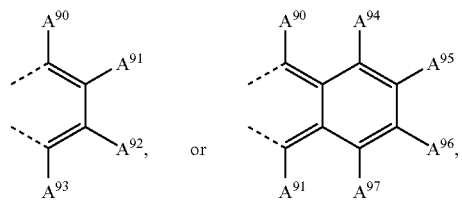

wherein $A^{90}, A^{91}, A^{92}, A^{93}, A^{94}, A^{95}, A^{96}$ and $A^{97}$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_5$-$C_{12}$cycloalkyl, $C_5$-$C_{12}$cycloalkyl which is substituted by E and/or interrupted by S—, —O—, or —NR$^{25}$—, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by E, $C_7$-$C_{25}$aralkoxy, $C_7$-$C_{25}$aralkoxy which is substituted by E, or —CO—R$^{28}$, $R^{68}$, $R^{69}$, $R^{78}$, $R^{79}$, $R^{88}$ and $R^{89}$ are independently of each other $C_1$-$C_{18}$ alkyl, $C_1$-$C_{24}$alkyl which is substituted by E and/or interrupted by D, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, or $C_7$-$C_{25}$aralkyl, or $R^{68}$ and $R^{69}$, $R^{78}$ and $R^{79}$, and/or $R^{88}$ and $R^{89}$ form a ring, especially a five- or six-membered ring, or $R^{68}$ and $R^{70}$, $R^{69}$ and $R^{73}$, $R^{77}$ and $R^{78}$ and/or $R^{84}$ and $R^{89}$ are a group

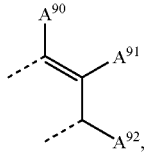

wherein D, E, R$^{25}$ and R$^{28}$ are defined as above.

Preferably, $Y^3$ and $Y^{3'}$ are independently of each other a group of formula

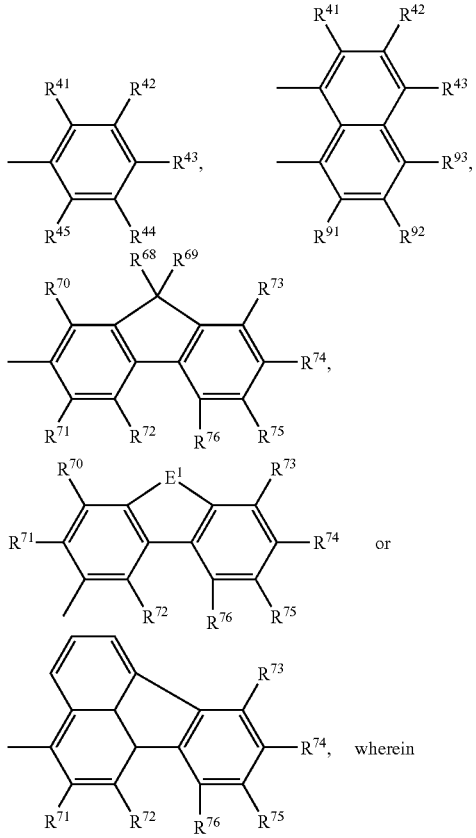

$R^{41}$ is hydrogen, $C_1$-$C_{24}$alkoxy, or O$C_7$-$C_{18}$aralkyl,
$R^{42}$ is hydrogen, or $C_1$-$C_{24}$alkyl,
$R^{43}$ is hydrogen, halogen, —CONR$^{25}$R$^{26}$, —COOR$^{27}$,

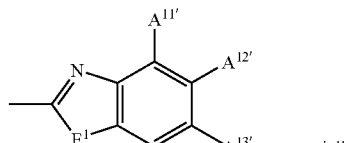

, especially

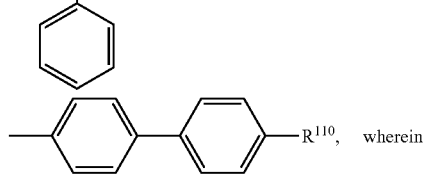

, or

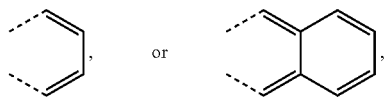

, wherein $E^1$ is —S—, —O—, or —NR$^{25'}$—, wherein R$^{25'}$ is $C_1$-$C_{24}$alkyl, or $C_6$-$C_{10}$aryl, $R^{110}$ is $C_1$-$C_{24}$alkyl, or $R^{42}$ and $R^{43}$ are a group of formula

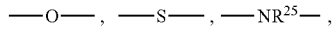

, or

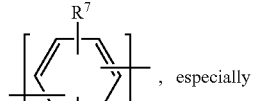

, $R^{44}$ is hydrogen, or $C_1$-$C_{24}$alkyl,
$R^{45}$ is hydrogen, or $C_1$-$C_{24}$alkyl,
$A^{11'}$, $A^{12'}$, $A^{13'}$, and $A^{14'}$ are independently of each other H, CN, $C_1$-$C_{24}$alkyl, $C_1$-$C_{24}$alkoxy, $C_1$-$C_{24}$alkylthio, —NR$^{25}$R$^{26}$, —CONR$^{25}$R$^{26}$, or —COOR$^{27}$, $R^{68}$ and $R^{69}$ are independently of each other $C_1$-$C_{24}$alkyl, especially $C_4$-$C_{12}$alkyl, especially hexyl, heptyl, 2-ethylhexyl, and octyl, which can be Interrupted by one or two oxygen atoms, $R^{71}$, $R^{72}$, $R^{73}$, $R^{74}$, $R^{75}$, $R^{76}$, $R^{90}$, $R^{91}$, $R^{92}$, and $R^{93}$ are independently of each other H, CN, $C_1$-$C_{24}$alkyl, $C_6$-$C_{10}$aryl, $C_1$-$C_{24}$alkoxy, $C_1$-$C_{24}$alkylthio, —NR$^{25}$R$^{26}$, —CONR$^{25}$R$^{26}$, or —COOR$^{27}$, R$^{25}$ and R$^{26}$ are independently of each other H, $C_6$-$C_{18}$aryl, $C_7$-$C_{18}$aralkyl, or $C_1$-$C_{24}$alkyl, and R$^{27}$ is $C_1$-$C_{24}$alkyl.

Examples of the divalent linking groups $Y^1$ and $Y^2$ in formula III, IV and VI are a single bond,

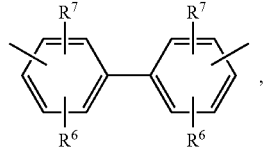

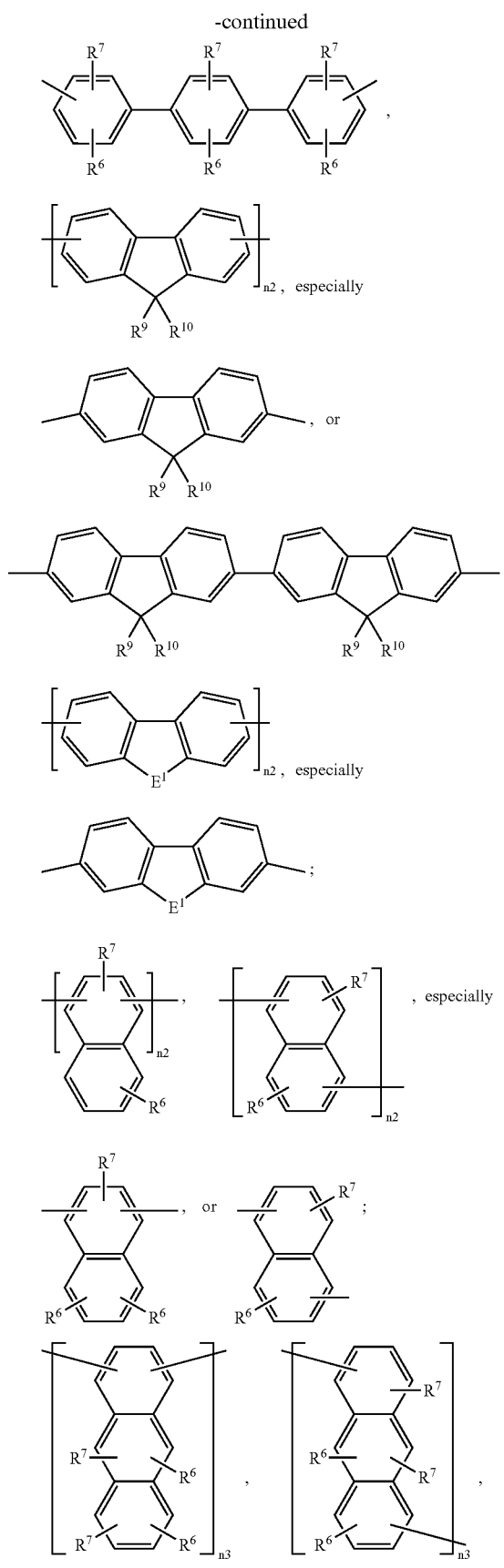
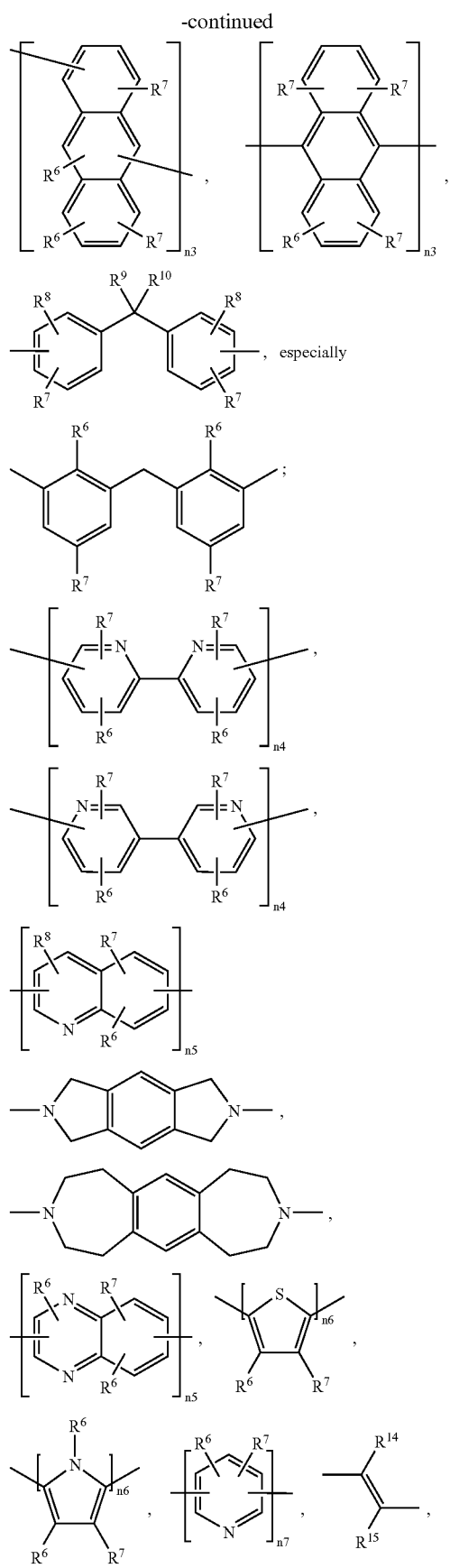

-continued

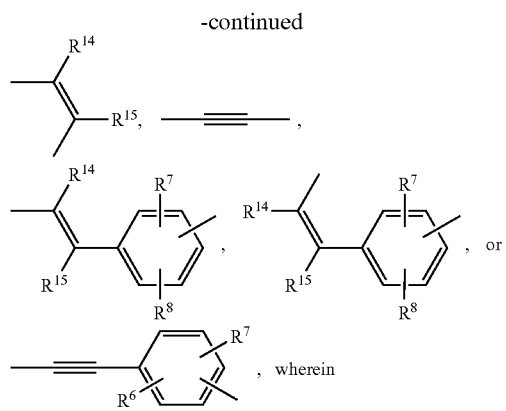
, wherein n1, n2, n3, n4, n5, n6 and n7 are 1, 2, or 3, in particular 1, $E^1$ is —S—, —O—, or —NR$^{25'}$—, wherein R$^{25'}$ is $C_1$-$C_{24}$alkyl, or $C_6$-$C_{10}$aryl, R$^6$ and R$^7$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_6$-$C_{12}$cycloalkyl, $C_5$-$C_{12}$cycloalkyl which is substituted by E and/or interrupted by S—, —O—, or —NR$^{25}$—, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by E, $C_7$-$C_{25}$aralkoxy, $C_7$-$C_{25}$aralkoxy which is substituted by E, or —CO—R$^{28}$, R$^8$ is $C_1$-$C_{24}$alkyl, $C_1$-$C_{24}$alkyl which is substituted by E and/or interrupted by D, $C_6$-$C_{24}$ aryl, or $C_7$-$C_{25}$aralkyl, R$^9$ and R$^{10}$ are independently of each other $C_1$-$C_{24}$alkyl, $C_1$-$C_{24}$alkyl which is substituted by E and/or interrupted by D, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, or $C_7$-$C_{25}$aralkyl, or R$^9$ and R$^{10}$ form a ring, especially a five- or six-membered ring, R$^{14}$ and R$^{15}$ are independently of each other H. $C_1$-$C_{24}$alkyl, $C_1$-$C_{24}$alkyl which is substituted by E and/or interrupted by D, $C_6$-$C_{24}$aryl, $C_6$-$C_{24}$aryl which is substituted by E, $C_2$-$C_{20}$heteroaryl, or $C_2$-$C_{20}$heteroaryl which is substituted by E, wherein D, E, R$^{25}$ and R$^{26}$ are defined as above.

Preferably, Y$^1$ is selected from

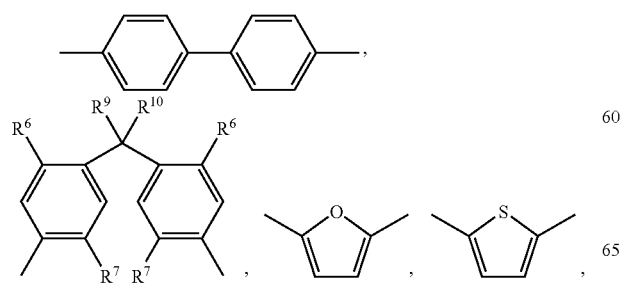

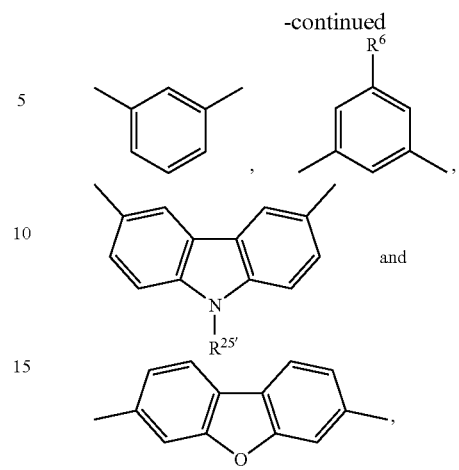

wherein R$^6$ is $C_1$-$C_{24}$alkoxy, or —O—$C_7$-$C_{25}$aralkyl, R$^7$ is H, or $C_1$-$C_{24}$alkyl, R$^9$ and R$^{10}$ are independently of each other $C_1$-$C_{24}$alkyl, especially $C_4$-$C_{12}$alkyl, which can be interrupted by one or two oxygen atoms, and R$^{25'}$ is $C_1$-$C_{24}$alkyl, or $C_6$-$C_{10}$aryl.

Y$^2$ is preferably a single bond, —O—, —S—, —NR$^{25}$, a group of formula

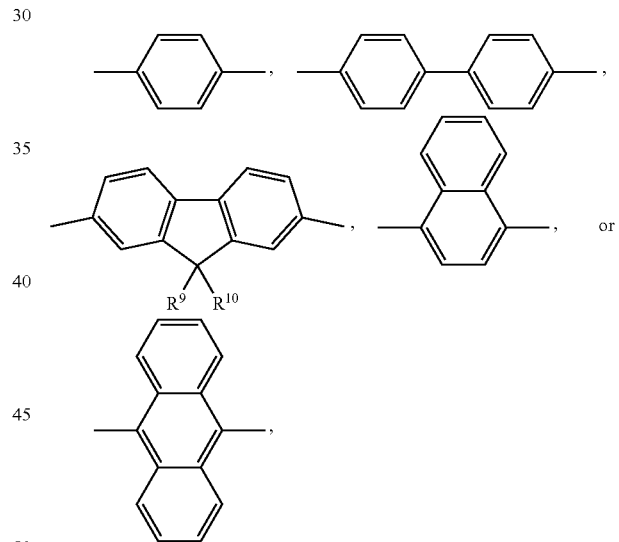

wherein R$^{25}$, R$^9$ and R$^{10}$ are defined as above.

In a first aspect, the present invention relates to an electroluminescent device, wherein the 2H-benzotriazole compound is a compound of formula II, especially of formula (IIa)

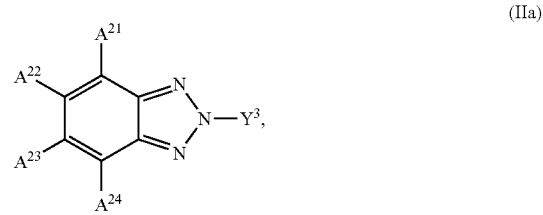

-continued

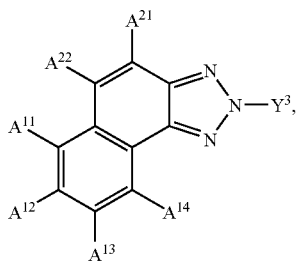
(IIb)

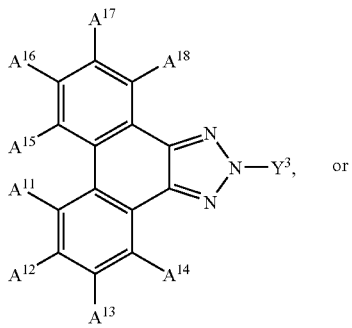
(IIc)

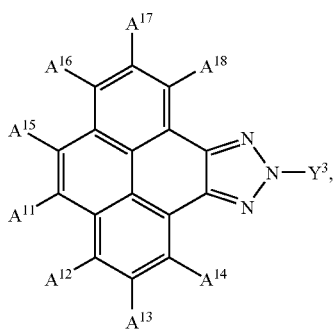
(IId)

$A^{21}$, $A^{22}$, $A^{23}$ and $A^{24}$ are independently of each other hydrogen, halogen, $C_1$-$C_{24}$alkyl, $C_1$-$C_{24}$perfluoroalkyl, $C_6$-$C_{18}$aryl, —$NR^{25}R^{26}$, —CO $NR^{25}R^{26}$, or —$COOR^{27}$, or $C_2$-$C_{10}$heteroaryl, especially a group of formula

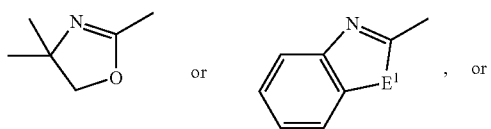

$A^{22}$ and $A^{23}$ or $A^{11}$ and $A^{23}$ are a group of formula

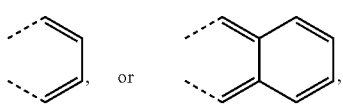

$A^{11}$, $A^{12}$, $A^{13}$, $A^{14}$, $A^{15}$, $A^{16}$, $A^{17}$, and $A^{18}$ are independently of each other H, CN, $C_1$-$C_{24}$alkyl, $C_1$-$C_{24}$alkoxy, $C_1$-$C_{24}$alkylthio, $C_6$-$C_{18}$aryl, —$NR^{25}R^{26}$, —$CONR^{25}R^{26}$, or —$COOR^{27}$, or $C_2$-$C_{10}$heteroaryl, wherein
$R^{25}$ and $R^{26}$ are independently of each other H, $C_6$-$C_{18}$aryl, $C_6$-$C_{18}$aralkyl, or $C_1$-$C_{24}$alkyl, $R^{27}$ is $C_1$-$C_{24}$alkyl, and $Y^3$ is a group of formula

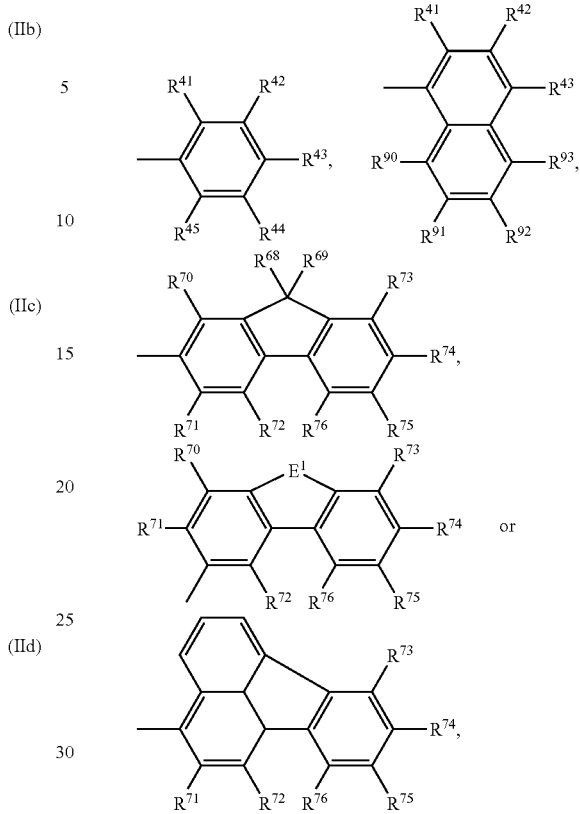

$R^{41}$ is hydrogen, $C_1$-$C_{24}$alkoxy, or $OC_7$-$C_{18}$aralkyl,
$R^{42}$ is hydrogen, or $C_1$-$C_{24}$alkyl,
$R^{43}$ is hydrogen, halogen, —$CONR^{25}R^{26}$, —$COOR^{27}$

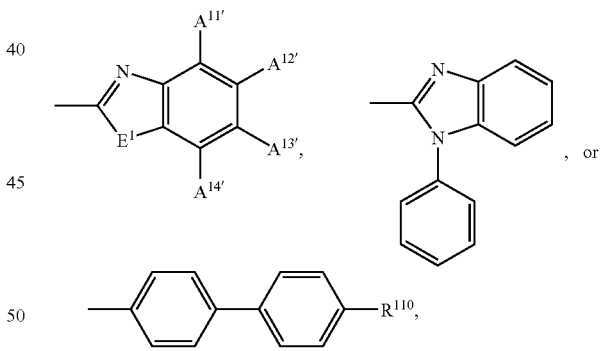

wherein
$E^1$ is —S—, —O—, or —$NR^{25'}$—, wherein $R^{25'}$ is $C_1$-$C_{24}$alkyl, or $C_6$-$C_{10}$aryl,
$R^{110}$ is H, CN, $C_1$-$C_{24}$alkyl, $C_1$-$C_{24}$alkoxy, $C_1$-$C_{24}$alkylthio, —$NR^{25}R^{26}$, —$CONR^{25}R^{26}$, or —$COOR^7$, or
$R^{42}$ and $R^{43}$ are a group of formula

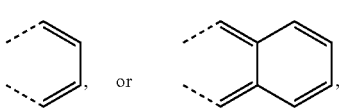

$R^{44}$ is hydrogen, or $C_1$-$C_{24}$alkyl, $R^{45}$ is hydrogen, or $C_1$-$C_{24}$alkyl, $A^{11'}$, $A^{12'}$, $A^{13'}$, and $A^{14'}$ are independently of each other H, CN, $C_1$-$C_{24}$alkyl, $C_1$-$C_{24}$alkoxy, $C_1$-$C_{24}$alkylthio, —$NR^{25}R^{26}$, —$CONR^{25}R^{26}$, or —$COOR^{27}$, $R^{68}$ and $R^{69}$ are independently of each other $C_1$-$C_{24}$alkyl, especially $C_4$-$C_{12}$alkyl, especially hexyl, heptyl, 2-ethylhexyl, and octyl, which can be interrupted by one or two oxygen atoms, $R^{70}$, $R^{71}$, $R^{72}$, $R^{73}$, $R^{74}$, $R^{75}$, $R^{76}$, $R^{90}$, $R^{91}$, $R^{92}$, and $R^{93}$ are independently of each other H, CN, $C_1$-$C_{24}$alkyl, $C_1$-$C_{24}$aryl, $C_1$-$C_{24}$alkoxy, $C_1$-$C_{24}$alkylthio, —$NR^{25}R^{26}$, —$CONR^{25}R^{26}$, or —$COOR^{27}$, $R^{25}$ and $R^{26}$ are independently of each other H, $C_6$-$C_{18}$aryl, $C_7$-$C_{18}$aralkyl, or $C_1$-$C_{24}$alkyl, and $R^{27}$ is $C_1$-$C_{24}$alkyl.

Among the compounds of formula IIa the following derivatives are preferred

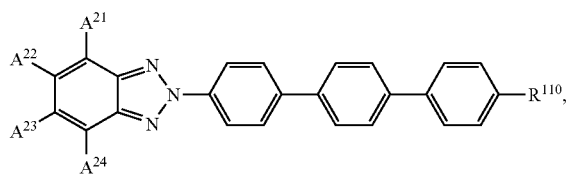

wherein $A^{23}$ is halogen, or $C_1$-$C_{24}$perfluoroalkyl, and $R^{43}$ and $Y^3$ is defined as above, wherein the compounds of formula IIb, IIc and IId are more preferred.

In a further embodiment, those compounds of formula II, especially of formula IIa are preferred, wherein $R^{41}$ is different from a hydroxy group.

In this aspect, the compounds listed below are most preferred:

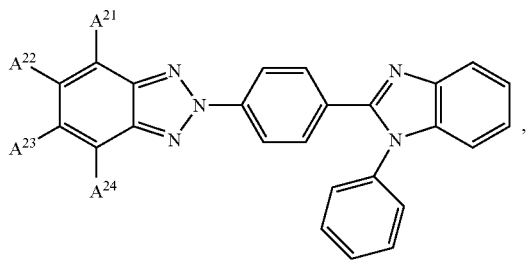

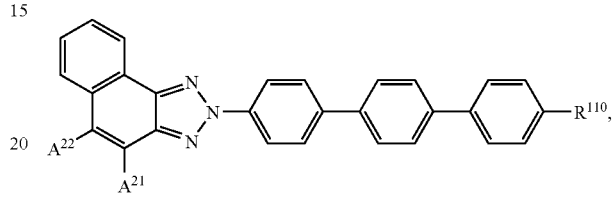

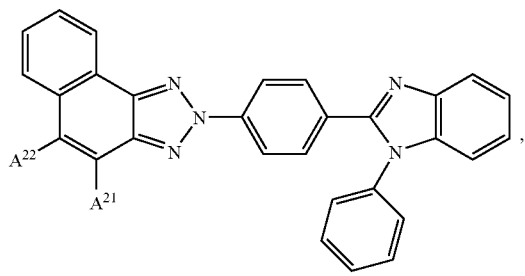

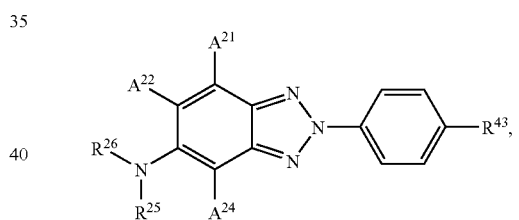

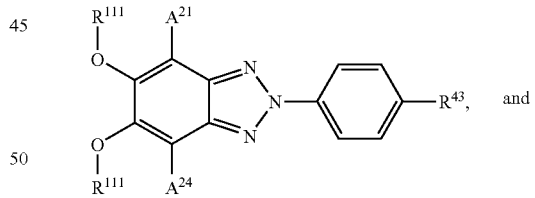

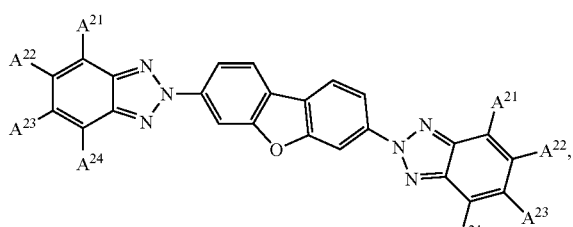

wherein $R^{111}$ is hydrogen, $C_1$-$C_{24}$alkyl, $C_1$-$C_{24}$perfluoroalkyl, or $C_6$-$C_{18}$aryl, and $A^{21}$, $A^{22}$, $A^{23}$, $A^{24}$, $R^{25}$, $R^{26}$, $R^{43}$, and $R^{110}$ are defined as above.

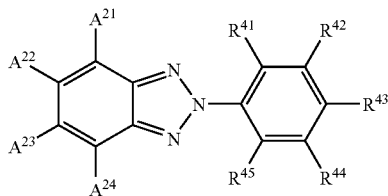

| Cpd. | $A^{21}$ | $A^{22}$ | $A^{23}$ | $A^{24}$ | $R^{41}$ | $R^{42}$ | $R^{43}$ | $R^{44}$ | $R^{45}$ |
|---|---|---|---|---|---|---|---|---|---|
| A1 | H | H | H | H | —OCH$_2$Ph | H | H | —CH$_3$ | H |
| A2 | H | H | H | H | OCH$_2$R | H | H | —CH$_3$ | H |
| A3 | H | H | —CO$_2$CH$_3$ | H | —OCH$_3$ | -tBu | H | -tBu | H |
| A4 | H | H | Cl | H | —OCH$_3$ | -tBu | H | -tBu | H |
| A5 | H | H | Ph | H | —OCH$_3$ | -tBu | H | -tBu | H |
| A6 | H | H | —N(CH$_2$Ph)$_2$ | H | H | H | H | H | H |
| A7 | H | H | Br | H | —OH | H | H | 1) | 1) |
| A8 | H | H | Br | H | —OCH$_3$ | H | H | 1) | 1) |
| A9 | H | H | —N(CH$_2$Ph)$_2$ | H | —OCH$_3$ | H | H | 1) | 1) |
| A10 | H | H | —CF$_3$ | H | —OCH$_2$Ph | H | H | —CH$_3$ | H |
| A11 | H | H | —CF$_3$ | H | H | H | —NHPh | H | H |
| A12 | H | H | —CF$_3$ | H | H | H | —OPh | H | H |
| A13 | H | H | F | H | H | H | —OPh | H | H |
| A14 | H | H | Cl | H | H | H | —NPh$_2$ | H | H |
| A15 | H | H | H | H | H | H | —N(CH$_3$)CH$_2$Ph | 1) | 1) |
| A16 | H | H | H | H | 1) | 1) | 2) | 1) | 1) |
| A17 | Ph | H | H | H | H | H | —N(Et)Ph | H | H |
| A18 | Ph | H | H | Ph | H | H | —N(CH$_3$)Ph | H | H |
| A19 | H | H | Ph | H | H | H | —NPh$_2$ | H | H |

$R^{44}$ and $R^{45}$ are a group of formula

| Cpd. | $A^{21}$ | $A^{22}$ | $R^{41}$ | $R^{42}$ | $R^{43}$ | $R^{44}$ | $R^{45}$ |
|---|---|---|---|---|---|---|---|
| B1 | H | H | H | H | —CO$_2$Et | H | H |
| B2 | H | H | H | H | —CO$_2$Na | H | H |
| B3 | H | H | H | H | -R' | H | H |
| B4 | H | H | H | H | Br | H | H |
| B5 | H | H | H | H | -R'' | H | H |
| B6 | H | H | H | H | —NCH$_3$Ph | H | H |

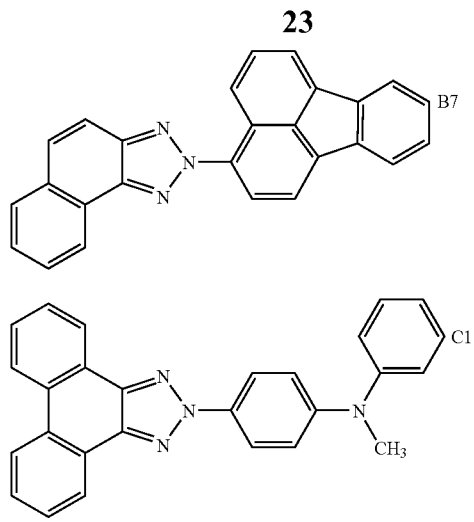

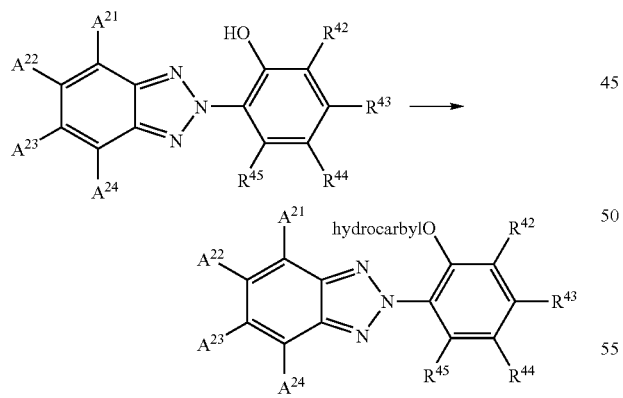

The present 2H-benzotriazole compounds of formula IIa are for instance derivatives of known hydroxyphenyl-2H-benzotriazole compounds. Known 2H-hydroxyphenyl-2H-benzotriazole compounds are commercially useful as ultraviolet light absorbers (UVA's). 2H-Benzotriazole ultraviolet light absorbers are characterized by having an ortho hydroxyphenyl-2H-benzotriazole moiety, for example as disclosed in U.S. Pat. Nos. 3,004,896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905; 4,853,471; 5,268,450; 5,278,314; 5,280,124; 5,319,091; 5,410,071; 5,436,349; 5,516,914; 5,554,760; 5,563,242; 5,574,166; 5,607,987, 5,977,219 and 6,166,218, the relevant parts of which are hereby incorporated by reference.

The present 2H-benzotriazoles may be obtained by simply capping the ortho hydroxy (the phenol) of known 2H-benzotriazole UV absorbers. This is achieved for example by alkylating the phenol to obtain an ortho-hydrocarbyloxyphenyl-2H-benzotriazole, for example:

The known 2H-benzotriazole UV absorbers are prepared as disclosed in the above-mentioned U.S. Patents. The benzotriazoles of this invention may have substitution patterns as disclosed in the above-mentioned U.S. Patents. The term "alkylating" above refers to "capping" the hydroxy with any suitable hydrocarbyl group. That is, the ortho hydroxy is replaced with an ortho hydrocarbyloxy group.

The term "hydrocarbyl group" broadly refers to a monovalent hydrocarbon group in which the valency is derived by abstraction of a hydrogen from a carbon atom. Hydrocarbyl includes for example aliphatics (straight and branched chain), cycloaliphatics, aromatics and mixed groups such as $C_7$-$C_{25}$aralkyl, $C_7$-$C_{25}$alkylaryl, $C_2$-$C_{24}$alkynyl, $C_5$-$C_{12}$cycloalkynyl. Hydrocarbyl includes such groups as alkyl, $C_5$-$C_{12}$cycloalkyl, $C_6$-$C_{30}$aryl, $C_7$-$C_{25}$aralkyl, $C_7$-$C_{25}$alkylaryl, $C_2$-$C_{24}$alkenyl, and $C_5$-$C_{12}$cycloalkenyl. A hydrocarbyl may optionally be interrupted by carbonyl, carboxyl, amino, amido, thio, sulfoxide, sulfonyl and ether groups and/or may optionally be substituted by hydroxy, amino, amido, carboxyl and thio groups.

In a second aspect, the present invention relates to an EL device, comprising a 2H-benzotriazole compound of formula III, especially of formula

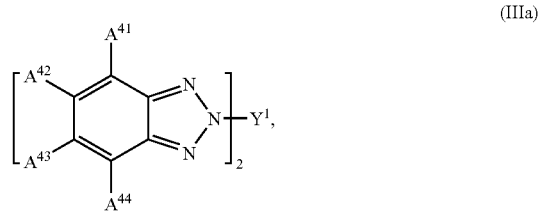

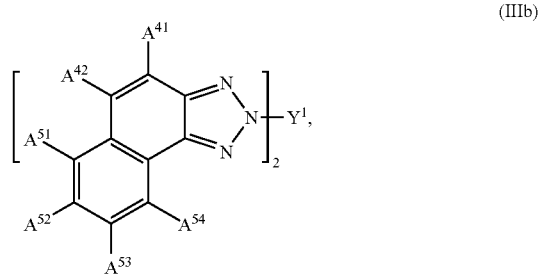

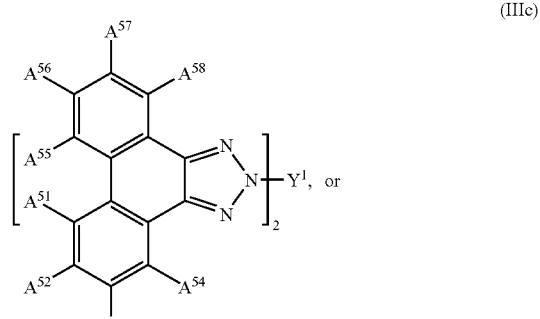

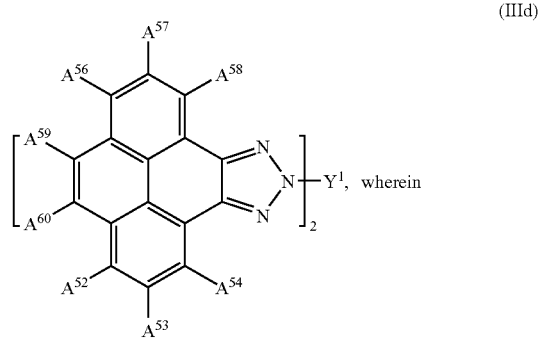

$A^{41}$, $A^{42}$, $A^{43}$ and $A^{44}$ are independently of each other hydrogen, halogen, $C_1$-$C_{24}$alkyl, $C_1$-$C_{24}$perfluoroalkyl, $C_6$-$C_{18}$aryl, —$NR^{25}R^{26}$, —CO $NR^{25}R^{26}$, or —$COOR^{27}$, or $C_2$-$C_{10}$heteroaryl, especially a group of formula

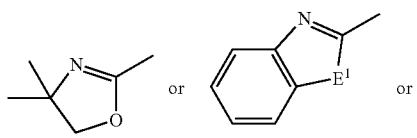

$A^{42}$ and $A^{43}$ are a group of formula

$A^{51}$, $A^{52}$, $A^{53}$, $A^{54}$, $A^{55}$, $A^{56}$, $A^{57}$, $A^{58}$, $A^{59}$ and $A^{60}$ are independently of each other H, CN, $C_1$-$C_{24}$alkyl, $C_1$-$C_{24}$alkoxy, $C_1$-$C_{24}$alkylthio, $C_6$-$C_{18}$aryl, —$NR^{25}R^{26}$, —$CONR^{25}R^{26}$, or —$COOR^{27}$, or $C_2$-$C_{10}$heteroaryl, wherein
$E^1$ is O, S, or $NR^{25}$,
$R^{25}$ and $R^{26}$ are independently of each other H, $C_6$-$C_{18}$aryl, $C_7$-$C_{18}$aralkyl, or $C_1$-$C_{24}$alkyl, $R^{27}$ is $C_1$-$C_{24}$alkyl, and
$Y^1$ is a group of formula

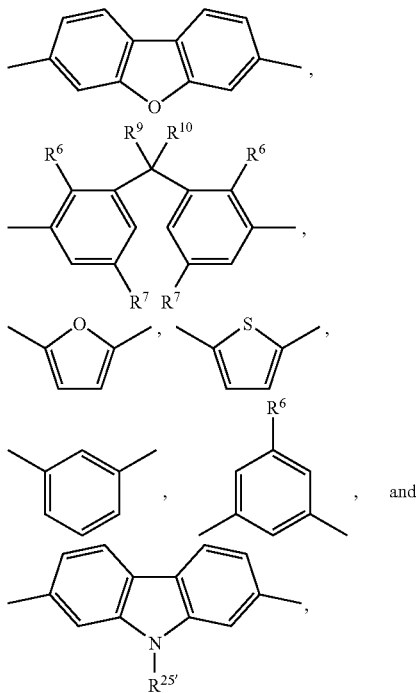

wherein $R^8$ is $C_1$-$C_{24}$alkoxy, or —O—$C_7$-$C_{25}$aralkyl,
$R^7$ is H, or $C_1$-$C_{24}$alkyl,
$R^9$ and $R^{10}$ are independently of each other $C_1$-$C_{24}$alkyl, especially $C_4$-$C_{12}$alkyl, which can be Interrupted by one or two oxygen atoms, and
$R^{25'}$ is $C_1$-$C_{24}$alkyl, or $C_6$-$C_{10}$aryl.

In this aspect the compounds listed below are most preferred:

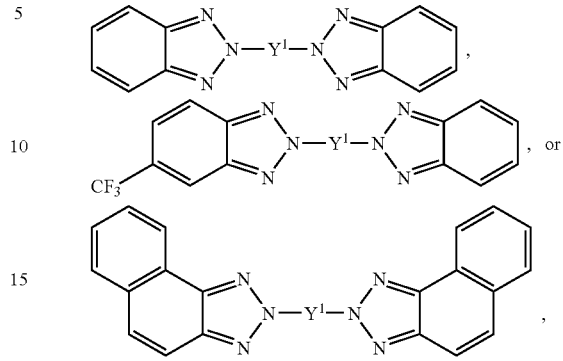

wherein $Y^1$ is selected from

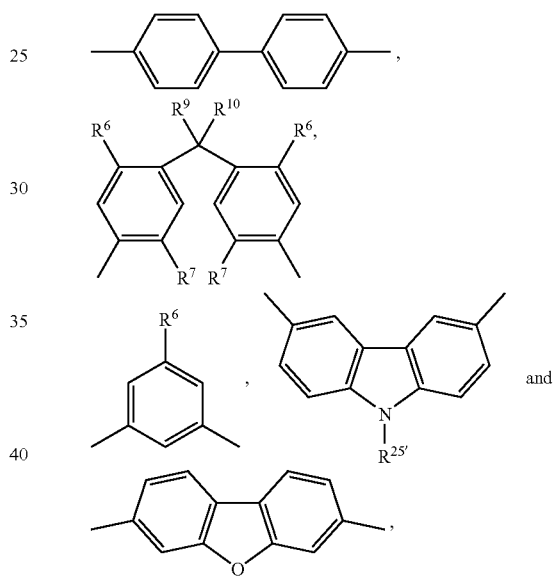

wherein $R^6$ is $C_1$-$C_{24}$alkoxy, or —O—$C_7$-$C_{26}$aralkyl, $R^7$ is H, or $C_1$-$C_{24}$alkyl, $R^9$ and $R^{10}$ are independently of each other $C_1$-$C_{24}$alkyl, especially $C_4$-$C_{12}$alkyl, which can be interrupted by one or two oxygen atoms, and $R^{25'}$ is $C_1$-$C_{24}$alkyl, wherein $R^6$ is $C_1$-$C_{24}$alkoxy, or —O—$C_7$-$C_{25}$aralkyl, $R^7$ is H, or $C_1$-$C_{24}$alkyl, $R^9$ and $R^{10}$ are independently of each other $C_1$-$C_{24}$alkyl, especially $C_4$-$C_{12}$alkyl, which can be interrupted by one or two oxygen atoms;

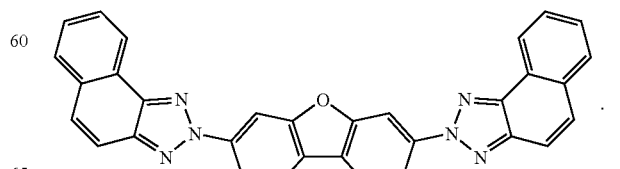

D2

In a third aspect, the present Invention relates to an EL device, comprising a 2H-benzotriazole compound of formula IV, especially of formula

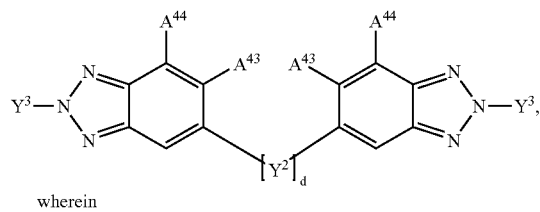

(VIa)

wherein d is 0, or 1,
$A^{43}$ and $A^{44}$ are defined as above,
$Y^2$ is a group of formula —O—, —S—, —$NR^{25}$—, a group of formula

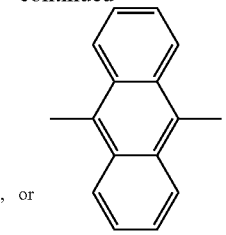

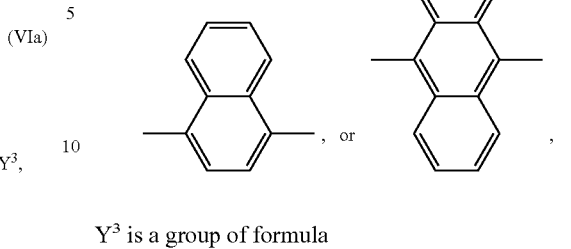

$Y^3$ is a group of formula wherein $R^9$ and $R^{10}$ are independently of each other $C_1$-$C_{24}$alkyl, especially $C_4$-$C_{12}$alkyl, which can be interrupted by one or two oxygen atoms,
$R^{41}$ is $C_1$-$C_{24}$alkoxy, or $C_7$-$C_{15}$phenylalkoxy and
$R^{44}$ is is H, $C_6$-$C_{10}$aryl, or $C_1$-$C_{24}$alkyl.

In this aspect, the following compounds are most preferred:

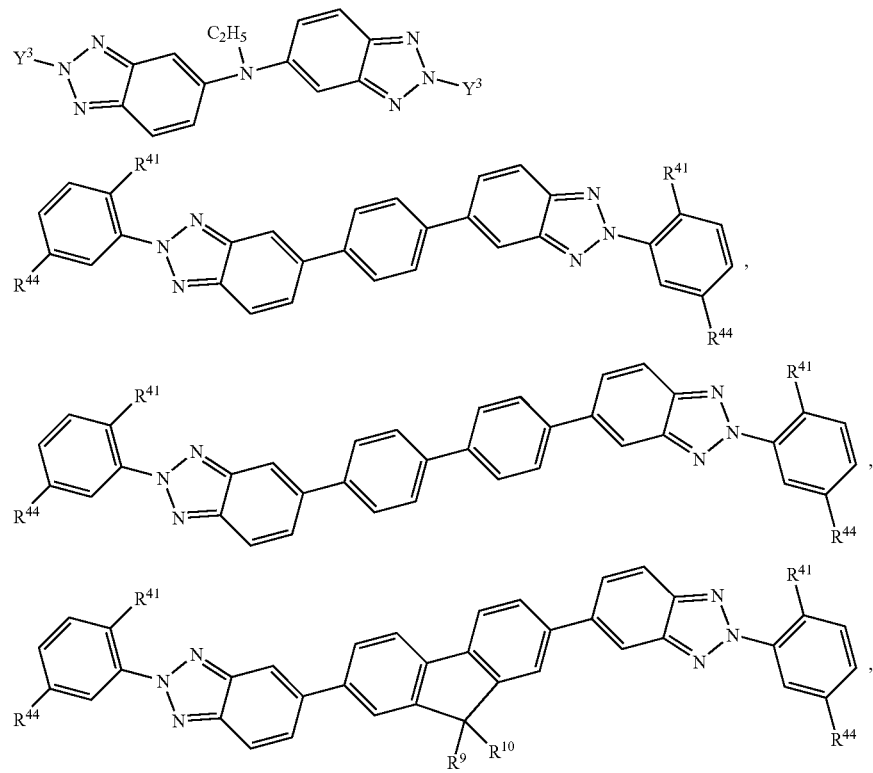

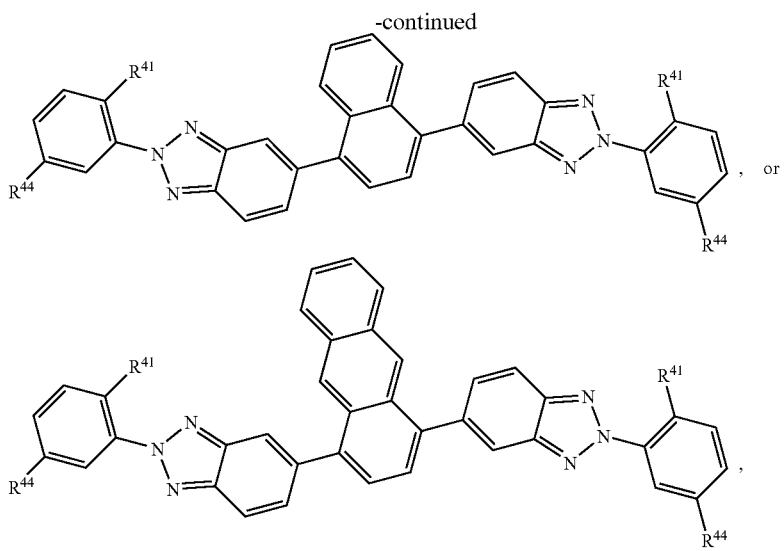

wherein $Y^3$, $R^9$, $R^{10}$, $R^{41}$ and $R^{44}$ are defined as above; and

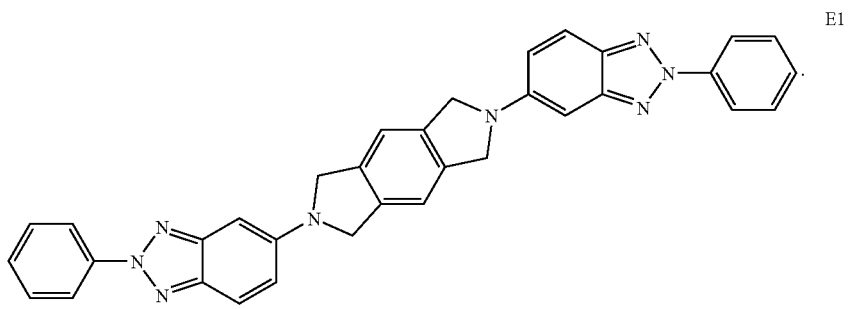

In a fourth aspect, the present invention relates to an EL device, comprising a 2H-benzotriazole compound of formula V, wherein $Ar^1$, $Ar^2$, $Y^1$, $Y^2$, and $Y^{3'}$ are defined as above.

In a fifth aspect, the present Invention relates to an EL device, comprising a 2H-benzotriazole compound of formula (VI), wherein $Ar^1$, $Ar^2$, $Ar^3$, $Y^1$, $Y^2$, and $Y^{3'}$ are defined as above.

The 2H-benzotriazoles of formulas (IV), (V) and (VI) may be prepared by any suitable process, for example, by the amination reaction as described in Hartwig et al., Journal Organic Chemistry 1999 (64), 5575, but can also be prepared by the process described below. The condensation reaction of an aromatic boronate and a bromide, commonly referred to as the "Suzuki reaction", is tolerant of the presence of a variety of organic functional groups and as reported by N. Miyaua and A. Suzuki in Chemical Reviews, Vol. 95, pp. 457-2483 (1995).

To prepare 2H-benzotriazoles corresponding to formula (IV) 2 equivalents of a bromide of formula

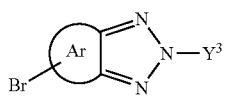

are reacted with one equivalent diboronic acid or diboronate corresponding to formula

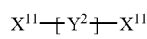

or a mixture thereof, wherein $X^{11}$ is independently in each occurrence a $—B(OH)_2$, $—B(OY^{11})_2$ or

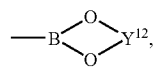

wherein $Y^{11}$ is independently in each occurrence a $C_1$-$C_{10}$alkyl group and $Y^{12}$ is Independently in each occurrence a $C_2$-$C_{10}$alkylene group, such as $—CY^{13}Y^{14}—CY^5Y^6—$, or $—CY^7Y^8—CY^9Y^{10}—CY^{15}Y^{16}—$, wherein $Y^5$, $Y^6$, $Y^7$, $Y^8$, $Y^9$, $Y^{10}$, $Y^{13}$, $Y^{14}$, $Y^{15}$ and $Y^{16}$ are independently of each other hydrogen, or a $C_1$-$C_{10}$alkyl group, especially $—C(CH_3)_2C(CH_3)_2—$, or $—C(CH_3)_2CH_2C(CH_3)_2—$, under the catalytic action of Pd and triphenylphosphine. The reaction is typically conducted at about 70° C. to 120° C. in an aromatic hydrocarbon solvent such as toluene. Other solvents such as dimethylformamide and tetrahydrofuran can also be used alone, or in mixtures with an aromatic hydrocarbon. An aqueous base, preferably sodium carbonate or bicarbonate, is used as the HBr scavenger. Depending on the reactivities of the reactants, a polymerization reaction may take 2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed., 2003, 42, 1407 and references cited therein). Other variations of reaction conditions are given by T. I. Wallow and B. M. Novak in Journal of Organic Chemistry, Vol. 59, pp. 5034-5037 (1994); and M. Remmers, M. Schulze, and G. Wegner in Macromolecular Rapid Communications, Vol. 17, pp. 239-252 (1996). The 2H-benzotriazoles of formulas (IV), (V) and (VI) can be prepared accordingly.

Halogen is fluorine, chlorine, bromine and iodine.

$C_1$-$C_{24}$alkyl is a branched or unbranched radical such as for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl or docosyl.

$C_1$-$C_{24}$perfluoroalkyl is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

$C_1$-$C_{24}$alkoxy radicals are straight-chain or branched alkoxy radicals, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

$C_2$-$C_{24}$alkenyl radicals are straight-chain or branched alkenyl radicals, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-24}$alkynyl is straight-chain or branched and preferably $C_{2-8}$alkynyl, which may be unsubstituted or substituted, such as, for example, ethynyl, 1-propyn-3-yl, 1-butyn-4yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_4$-$C_{18}$cycloalkyl, especially $C_5$-$C_{12}$cycloalkyl, is preferably $C_5$-$C_{12}$cycloalkyl or said cycloalkyl substituted by one to three $C_1$-$C_4$alkyl groups, such as, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl, cyclononyl, cyclodecyl, cyclododecyl. Cyclohexyl and cyclopentyl are most preferred.

Examples of $C_4$-$C_{18}$cycloalkyl, which is interrupted by S, O, or $NR^{25}$, are piperidyl, piperazinyl and morpholinyl.

$C_2$-$C_{24}$alkenyl is for example vinyl, allyl, butenyl, pentenyl, hexenyl, heptenyl, or octenyl.

Aryl is usually $C_6$-$C_{30}$aryl, preferably $C_6$-$C_{24}$aryl, which optionally can be substituted, such as, for example, phenyl, 4-methylphenyl, 4-methoxyphenyl, naphthyl, biphenylyl, 2-fluorenyl, phenanthryl, anthryl, tetracyl, pentacyl, hexacyl, terphenylyl or quadphenylyl; or phenyl substituted by one to three $C_1$-$C_4$alkyl groups, for example o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

$C_7$-$C_{24}$aralkyl radicals are preferably $C_7$-$C_{15}$aralkyl radicals, which may be substituted, such as, for example, benzyl, 2-benzyl-2-propyl, β-phenethyl, α-methylbenzyl, α,α-dimethylbenzyl, ω-phenyl-butyl, ω-phenyl-octyl, ω-phenyldodecyl; or phenyl-$C_1$-$C_4$alkyl substituted on the phenyl ring by one to three $C_1$-$C_4$alkyl groups, such as, for example, 2-methylbenzyl, 3-methylbenzyl, 4-methylbenzyl, 2,4-dimethylbenzyl, 2,6-dimethylbenzyl or 4-tert-butylbenzyl or 3-methyl-5-(1',1',3',3'-tetramethyl-butyl)-benzyl.

Heteroaryl is typically $C_2$-$C_{26}$heteroaryl, i.e. a ring with five to seven ring atoms or a condensed rig system, wherein nitrogen, oxygen or sulfur are the possible hetero atoms, and is typically an unsaturated heterocyclic radical with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, which can be unsubstituted or substituted.

$C_5$-$C_{18}$cycloalkoxy is, for example, cyclopentyloxy, cyclohexyloxy, cycloheptyloxy or cyclooctyloxy, or said cycloalkoxy substituted by one to three $C_1$-$C_4$alkyl, for example, methylcyclopentyloxy, dimethylcyclopentyloxy, methylcyclohexyloxy, dimethylcyclohexyloxy, trimethylcyclohexyloxy, or tert-butylcyclohexyloxy.

$C_8$-$C_{24}$aryloxy is typically phenoxy or phenoxy substituted by one to three $C_1$-$C_4$alkyl groups, such as, for example o-, m- or p-methylphenoxy, 2,3-dimethylphenoxy, 2,4dimethylphenoxy, 2,5-dimethylphenoxy, 2,6-dimethylphenoxy, 3,4dimethylphenoxy, 3,5-dimethylphenoxy, 2-methyl-6-ethylphenoxy, 4-tert-butylphenoxy, 2-ethylphenoxy or 2,6-diethylphenoxy.

$C_6$-$C_{24}$aralkoxy is typically phenyl-$C_1$-$C_9$alkoxy, such as, for example, benzyloxy, α-methylbenzyloxy, α,α-dimethylbenzyloxy or 2-phenylethoxy.

$C_1$-$C_{24}$alkylthio radicals are straight-chain or branched alkylthio radicals, such as e.g. methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio.

$C_1$-$C_{24}$alkylselenium and $C_1$-$C_{24}$alkyltellurium are $C_1$-$C_{24}$alkylSe— and $C_1$-$C_{24}$alkylTe—, respectively.

Examples of a five or six membered ring formed by $R^9$ and $R^{10}$ and $R^{25}$ and $R^{26}$, respectively are heterocycloalkanes or heterocycloalkenes having from 3 to 5 carbon atoms which can have one additional hetero atom selected from nitrogen, oxygen and sulfur, for example

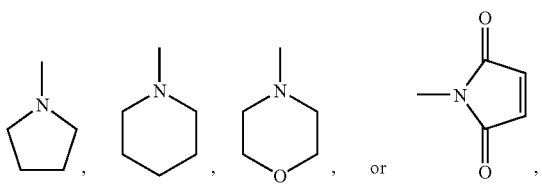

which can be part of a bicyclic system, for example

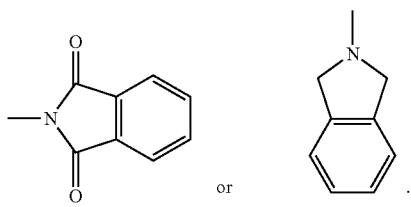

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group.

The term "haloalkyl" means groups given by partially or wholly substituting the above-mentioned alkyl group with halogen, such as trifluoromethyl etc. The "aldehyde group, ketone group, ester group, carbamoyl group and amino group" include those substituted by an $C_1$-$C_{24}$alkyl group, a $C_4$-$C_{18}$cycloalkyl group, an $C_6$-$C_{30}$aryl group, an $C_7$-$C_{24}$aralkyl group or a heterocyclic group, wherein the alkyl group, the cycloalkyl group, the aryl group, the aralkyl group and the heterocyclic group may be unsubstituted or substituted. The term "silyl group" means a group of formula —Si$R^{105}R^{106}R^{107}$, wherein $R^{105}$, $R^{106}$ and $R^{107}$ are independently of each other a $C_1$-$C_8$alkyl group, in particular a $C_1$-$C_4$ alkyl group, a $C_6$-$C_{24}$aryl group or a $C_7$-$C_{12}$aralkyl group, such as a trimethylsilyl group.

If a substituent, such as, for example $R^6$ and $R^7$, occurs more than one time in a group, it can be different in each occurrence.

As described above, the aforementioned radicals may be substituted by E and/or, if desired, interrupted by D. Interruptions are of course possible only in the case of radicals containing at least 2 carbon atoms connected to one another by single bonds; $C_6$-$C_{18}$aryl is not interrupted; interrupted arylalkyl or alkylaryl contains the unit D in the alkyl moiety. $C_1$-$C_{24}$alkyl substituted by one or more E and/or interrupted by one or more units D is, for example, $(CH_2CH_2O)_n$—$R^x$, where n is a number from the range 1-9 and $R^x$ is H or $C_1$-$C_{10}$alkyl or $C_2$-$C_{10}$alkanoyl (e.g. CO—CH($C_2H_5$)$C_4H_9$), $CH_2$—CH(O$R^{y'}$)—$CH_2$—O—$R^y$, where $R^y$ is $C_1$-$C_{24}$alkyl, $C_5$-$C_{12}$cycloalkyl, phenyl, $C_7$-$C_{15}$phenylalkyl, and $R^{y'}$ embraces the same definitions as $R^y$ or is H; $C_1$-$C_8$alkylene-COO—$R^z$, e.g. $CH_2COOR^z$, $CH(CH_3)COOR^z$, $C(CH_3)_2$CO-O$R^z$, where $R^z$ is H, $C_1$-$C_{24}$alkyl, $(CH_2CH_2O)_{1-9}$—$R^x$, and $R^x$ embraces the definitions indicated above; $CH_2CH_2$—O—CO—CH=$CH_2$; $CH_2CH(OH)CH_2$—O—CO—C($CH_3$)=$CH_2$.

The blue-emitting 2H-benzotriazoles of this invention emit light below about 520 nm, for example between about 380 nm and about 520 nm. For example, the blue-emitting 2H-benzotriazoles of this invention have a NTSC coordinate of about (0.14, 0.08), where the first coordinate is between about 0.12 and about 0.16, and the second coordinate is between about 0.05 and about 0.10.

The present compounds of formula I, Including those of formulae II, III, IV, V and VI, as well as the ortho-hydrocarbyloxyphenyl-2H-benzotriazoles, may also function as other than a blue-emitting organic compound, for example they may also function as a hole-injecting, hole-transporting, and electron-injecting or an electron-transporting material.

The organic EL device of the present Invention has significant industrial values since it can be adapted for a flat panel display of an on-wall television set, a flat light-emitting device, a light source for a copying machine or a printer, a light source for a liquid crystal display or counter, a display signboard and a signal light.

The material of the present invention can be used in the fields of an organic EL device, an electrophotographic photoreceptor, a photoelectric converter, a solar cell, and an Image sensor.

To obtain organic layers of this invention with the proper $T_g$, or glass transition temperature, it is advantageous that the present 2H-benzotriazoles have a melting point greater than about 150° C., for example greater than about 200° C., for example greater than about 250° C., for instance greater than about 300° C.

The electroluminescent devices of the present invention are otherwise designed as is known in the art, for example as described in U.S. Pat. Nos. 5,518,824, 6,280,859, 5,629,389, 5,486,406, 5,104,740 and 5,116,708, the relevant disclosures of which are hereby incorporated by reference.

The present invention relates to an electroluminescent device having the 2H-benzotriazoles of of formula I between an anode and a cathode and emitting light by the action of electrical energy.

Typical constitutions of latest organic electroluminescent devices are:
(i) an anode/a hole transporting layer/an electron transporting layer/a cathode, in which 2H-benzotriazoles of of formula I are used either as positive-hole transport compound, which is exploited to form the light emitting and hole transporting layers, or as electron transport compound, which can be exploited to form the light-emitting and electron transporting layers,
(ii) an anode/a hole transporting layer/a light-emitting layer/ an electron transporting layer/a cathode, in which the 2H-benzotriazoles of of formula I form the light-emitting layer regardless of whether they exhibit positive-hole or electron transport properties in this constitution,
(iii) an anode/a hole injection layer/a hole transporting layer/a light-emitting layer/an electron transporting layer/a cathode,
(iv) an anode/a hole transporting layer/a light-emitting layer/a positive hole inhibiting layer/an electron transporting layer/a cathode,
(v) an anode/a hole injection layer/a hole transporting layer/a light-emitting layer/a positive hole inhibiting layer/an electron transporting layer/a cathode,
(vi) an anode/a light-emitting layer/an electron transporting layer/a cathode,
(vii) an anode/a light-emitting layer/a positive hole inhibiting layer/an electron transporting layer/a cathode,
(viii) a mono-layer containing a light emitting material alone or a combination of a light emitting material and any of the materials of the hole transporting layer, the hole-blocking layer and/or the electron transporting layer, and
(ix) a multi-layered structure described in (ii) to (vii), wherein a light emitting layer is the mono-layer defined in (viii).

The 2H-benzotriazoles of of formula I can, in principal be used for any organic layer, such as, for example, hole transporting layer, light emitting layer, or electron transporting layer, but are preferably used as the light emitting material in the light emitting layer, optionally as a host or guest component.

The light emitting compounds of this invention exhibit intense fluorescence in the solid state and have excellent electric-field-applied light emission characteristics. Further, the light emitting compounds of this invention are excellent in the injection of holes from a metal electrode and the transportation of holes; as well as being excellent in the injection of electrons from a metal electrode and the transportation of electrons. They are effectively used as light emitting materials and may be used in combination with other hole transporting materials, other electron transporting materials or other dopants.

The 2H-benzotriazoles of the present invention form uniform thin films. The light emitting layers may therefore be formed of the present 2H-benzotriazoles alone.

Alternatively, the light-emitting layer may contain a known light-emitting material, a known dopant, a known hole-injecting material or a known electron-injecting material as required. In the organic EL device, a decrease in the brightness and life caused by quenching can be prevented by forming it as a multi-layered structure. The light-emitting material, a dopant, a hole-injecting material and an electron-injecting material may be used in combination as required. Further, a dopant can improve the light emission brightness and the light emission efficiency, and can attain red, green or blue light emission. Further, each of the hole-injecting zone, the light-emitting layer and the electron-injecting zone may have the layer structure of at least two layers. In the hole-injecting zone In this case, a layer to which holes are injected from an electrode is called "hole-injecting layer", and a layer which receives holes from the hole-injecting layer and transport the holes to a light-emitting layer is called "hole-transporting layer". In the electron-injecting zone, a layer to which electrons are injected from an electrode is called "electron-injecting layer", and a layer which receives electrons from the electron-injecting layer and transports the electrons to a light-emitting layer is called "electron-transporting layer". These layers are selected and used depending upon factors such as the energy level and heat resistance of materials and adhesion to an organic layer or metal electrode.

The light-emitting material or the dopant which may be used in the light-emitting layer together with the 2H-benzotriazoles of the present invention includes for example anthracene, naphthalene, phenanthrene, pyrene, tetracene, coronene, chrysene, fluorescein, perylene, phthaloperylene, naphthaloperylene, perinone, phthaoperinone, naphthaloperinone, diphenylbutadiene, tetraphenylbutadiene, coumarine, oxadiazole, aldazine, bisbenzoxazoline, bisstyryl, pyrazine, cyclopentadiene, quinoline metal complex, aminoquinoline metal complex, benzoquinoline metal complex, imine, diphenylethylene, vinyl anthracene, diaminocarbazole, pyran, thiopyran, polymethine, merocyanine, an imidazole-chelated oxynoid compound, quinacridone, rubrene, and fluorescent dyestuffs for a dyestuff laser or for brightening.

The 2H-benzotriazoles of the present invention and the above compound or compounds that can be used in a light-emitting layer may be used in any mixing ratio for forming a light-emitting layer. That is, 2H-benzotriazoles of the present invention may provide a main component for forming a light-emitting layer, or they may be a doping material in another main material, depending upon a combination of the above compounds with the present 2H-benzotriazoles of the present invention. Good results are, for example, achieved, when DPVBi (4,4'-bis-(2,2-diphenyl-1-vinyl)biphenyl) is used as host and Compound B7 is used as guest.

Thin film type electroluminescent devices usually consist essentially of a pair of electrodes and at least one charge transporting layer in between. Usually two charge transporting layers, a hole transporting layer (next to the anode) and an electron transporting layer (next to the cathode) are present. Either one of them contains—depending on its properties as hole-transporting or electron-transporting material—an inorganic or organic fluorescence substance as light-emitting material. It is also common, that a light-emitting material is used as an additional layer between the hole-transporting and the electron-transporting layer. In the above mentioned device structure, a hole injection layer can be constructed between an anode and a hole transporting layer and/or a positive hole inhibiting layer can be constructed between a light emitting layer and an electron transporting layer to maximise hole and electron population in the light emitting layer, reaching large efficiency in charge recombination and intensive light emission.

The devices can be prepared in several ways. Usually, vacuum evaporation is used for the preparation. Preferably, the organic layers are laminated In the above order on a commercially available indium-fin-oxide ("ITO") glass substrate held at room temperature, which works as the anode in the above constitutions. The membrane thickness is preferably in the range of 1 to 10,000 nm, more preferably 1 to 5,000 nm, more preferably 1 to 1,000 nm, more preferably 1 to 500 nm. The cathode metal, such as a Mg/Ag alloy, a binary Li—Al or LiF—Al system with an thickness in the range of 50-200 nm is laminated on the top of the organic layers. The vacuum during the deposition is preferably less than 0.1333 Pa ($1\times10^{-3}$ Torr), more preferably less than $1.333\times10^{-3}$ Pa ($1\times10^{-5}$ Torr), more preferably less than $1.333\times10^{-4}$ Pa ($1\times10^{-6}$ Torr).

As anode usual anode materials which possess high work function such as metals like gold, silver, copper, aluminum, indium, iron, zinc, tin, chromium, titanium, vanadium, cobalt, nickel, lead, manganese, tungsten and the like, metallic alloys such as magnesium/copper, magnesium/silver, magnesium/aluminum, aluminum/indium and the like, semiconductors such as Si, Ge, GaAs and the like, metallic oxides such as indium-tin-oxide ("ITO"), ZnO and the like, metallic compounds such as CuI and the like, and furthermore, electroconducting polymers, such as polyacetylene, polyaniline, polythiophene, polypyrrole, polyparaphenylene and the like, preferably ITO, most preferably ITO on glass as substrate can be used.

Of these electrode materials, metals, metallic alloys, metallic oxides and metallic compounds can be transformed into electrodes, for example, by means of the sputtering method. In the case of using a metal or a metallic alloy as a material for an electrode, the electrode can be formed also by the vacuum deposition method. In the case of using a metal or a metallic alloy as a material forming an electrode, the electrode can be formed, furthermore, by the chemical plating method (see for example, Handbook of Electrochemistry, pp 383-387, Mazuren, 1985). In the case of using an electroconducting polymer, an electrode can be made by forming it into a film by means of anodic oxidation polymerization method onto a substrate which is previously provided with an electroconducting coating. The thickness of an electrode to be formed on a substrate is not limited to a particular value, but, when the substrate is used as a light emitting plane, the thickness of the electrode is preferably within the range of from 1 nm to 300 nm, more preferably, within the range of from 5 to 200 nm so as to ensure transparency.

In a preferred embodiment ITO is used on a substrate having an ITO film thickness in the range of from 10 nm (100 Å) to 1µ (10000 Å), preferably from 20 nm (200 Å) to 500 nm (5000 Å). Generally, the sheet resistance of the ITO film is chosen in the range of not more than 100 $\Omega/cm^2$, preferably not more than 50 $\Omega/cm^2$.

Such anodes are commercially available from Japanese manufacturers, such as Geomatech Co. Ltd., Sanyo Vacuum Co. Ltd., Nippon Sheet Glass Co. Ltd.

As substrate either an electronconducting or electrically insulating material can be used. In case of using an electroconducting substrate, a light emitting layer or a positive hole transporting layer is directly formed thereupon, while in case of using an electrically insulating substrate, an electrode is firstly formed thereupon and then a light emitting layer or a positive hole transporting layer is superposed.

The substrate may be either transparent, semi-transparent or opaque. However, in case of using a substrate as an indicating plane, the substrate must be transparent or semi-transparent.

Transparent electrically insulating substrates are, for example, inorganic compounds such as glass, quartz and the like, organic polymeric compounds such as polyethylene, polypropylene, polymethylmethacrylate, polyacrylonitrile, polyester, polycarbonate, polyvinylchloride, polyvinylalcohol, polyvinylacetate and the like. Each of these substrates can be transformed into a transparent electroconducting substrate by providing it with an electrode according to one of the methods described above.

Examples of semi-transparent electrically insulating substrates are inorganic compounds such as alumina, YSZ (yttrium stabilized zirconia) and the like, organic polymeric compounds such as polyethylene, polypropylene, polystyrene, epoxy resins and the like. Each of these substrates can be transformed into a semi-transparent electroconducting substrate by providing it with an electrode according to one of the abovementioned methods.

Examples of opaque electroconducting substrates are metals such as aluminum, indium, iron, nickel, zinc, tin, chromium, titanium, copper, silver, gold, platinum and the like, various electroplated metals, metallic alloys such as bronze, stainless steel and the like, semiconductors such as Si, Ge, GaAs, and the like, electroconducting polymers such as polyaniline, polythiophene, polypyrrole, polyacetylene, polyparaphenylene and the like.

A substrate can be obtained by forming one of the above listed substrate materials to a desired dimension. It is preferred that the substrate has a smooth surface. Even, if it has a rough surface, It will not cause any problem for practical use, provided that it has round unevenness having a curvature of not less than 20 µm. As for the thickness of the substrate, there is no restriction as far as it ensures sufficient mechanical strength.

As cathode usual cathode materials which possess low work function such as alkali metals, earth alkaline metals, group 13 elements, silver, and copper as well as alloys or mixtures thereof such as sodium, lithium, potassium, calcium, lithium fluoride (UF), sodium-potassium alloy, magnesium, magnesium-silver alloy, magnesium-copper alloy, magnesium-aluminum alloy, magnesium-indium alloy, aluminum, aluminum-aluminum oxide alloy, aluminum-lithium alloy, indium, calcium, and materials exemplified in EP-A 499,011 such as electroconducting polymers e.g. polypyrrole, polythiophene, polyaniline, polyacetylene etc., preferably Mg/Ag alloys, LiF—Al or Li—Al compositions can be used.

In a preferred embodiment a magnesium-silver alloy or a mixture of magnesium and silver, or a lithium-aluminum alloy, lithium fluoride-aluminum alloy or a mixture of lithium and aluminum can be used In a film thickness in the range of from 10 nm (100 Å) to 1 µm (10000 Å), preferably from 20 nm (200 Å) to 500 nm (5000 Å).

Such cathodes can be deposited on the foregoing electron transporting layer by known vacuum deposition techniques described above.

In a preferred embodiment of this invention a light-emitting layer can be used between the hole transporting layer and the electron transporting layer. Usually the light-emitting layer is prepared by forming a thin film on the hole transporting layer.

As methods for forming said thin film, there are, for example, the vacuum deposition method, the spin-coating method, the casting method, the Langmuir-Blodgett ("LB") method and the like. Among these methods, the vacuum deposition method, the spin-coating method and the casting method are particularly preferred in view of ease of operation and cost.

In case of forming a thin film using a composition by means of the vacuum deposition method, the conditions under which the vacuum deposition is carried out are usually strongly dependent on the properties, shape and crystalline state of the compound(s). However, optimum conditions are usually as follows: temperature of the heating boat: 100 to 400° C.; substrate temperature: −100 to 350° C.; pressure: $1.33 \times 10^4$ Pa ($1 \times 10^2$ Torr) to $1.33 \times 10^{-4}$ Pa ($1 \times 10^{-6}$ Torr) and deposition rate: 1 pm to 6 nm/sec.

In an organic EL element, the thickness of the light emitting layer is one of the factors determining its light emission properties. For example, if a light emitting layer is not sufficiently thick, a short circuit can occur quite easily between two electrodes sandwiching said light emitting layer, and therefor, no EL emission is obtained. On the other hand, if the light emitting layer is excessively thick, a large potential drop occurs inside the light emitting layer because of its high electrical resistance, so that the threshold voltage for EL emission increases. Accordingly, the thickness of the organic light emitting layer is limited to the range of from 5 nm to 5 µm, preferably to the range of from 10 nm to 500 nm.

In the case of forming a light emitting layer by using the spin-coating method and the casting method, ink jet printing method, the coating can be carried out using a solution prepared by dissolving the composition in a concentration of from 0.0001 to 90% by weight in an appropriate organic solvent such as benzene, toluene, xylene, tetrahydrofurane, methyltetrahydrofurane, N,N-dimethylformamide, dichloromethane, dimethylsulfoxide and the like. If the concentration exceeds 90% by weight, the solution usually is so viscous that it no longer permits forming a smooth and homogenous film. On the other hand, if the concentration is less than 0.0001% by weight, the efficiency of forming a film is too low to be economical. Accordingly, a preferred concentration of the composition is within the range of from 0.01 to 80% by weight.

In the case of using the above spin-coating or casting method, it is possible to further improve the homogeneity and mechanical strength of the resulting layer by adding a polymer binder to the solution for forming the light emitting layer. In principle, any polymer binder may be used, provided that it is soluble in the solvent in which the composition is dissolved.

Examples of such polymer binders are polycarbonate, polyvinylalcohol, polymethacrylate, polymethylmethacrylate, polyester, polyvinylacetate, epoxy resin and the like. However, if the solid content composed of the polymer binder and the composition exceeds 99% by weight, the fluidity of the solution is usually so low that it is impossible to form a light emitting layer excellent in homogeneity. On the other hand, if the content of the composition is substantially smaller than that of the polymer binder, the electrical resistance of said layer is very large, so that it does not emit light unless a high voltage is applied thereto. Accordingly, the preferred ratio of the polymer binder to the composition is chosen within the range of from 10:1 to 1:50 by weight, and the solid content composed of both components in the solution is preferably within the range of from 0.01 to 80% by weight, and more preferably, within the range of 0.1 to 60% by weight.

As hole-transporting layers known organic hole transporting compounds such as polyvinyl carbazole

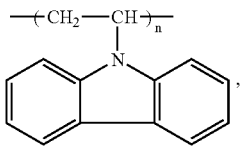

a TPD compound disclosed in J. Amer. Chem. Soc. 90 (1968) 3925:

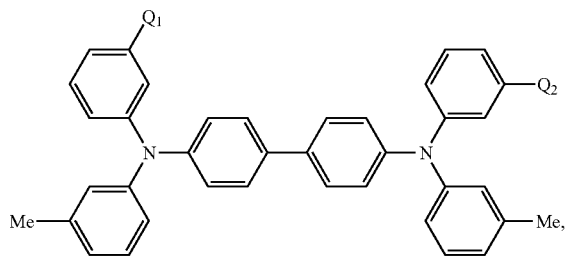

wherein $Q_1$ and $Q_2$ each represent a hydrogen atom or a methyl group;

a compound disclosed in J. Appl. Phys. 65(9) (1989) 3610:

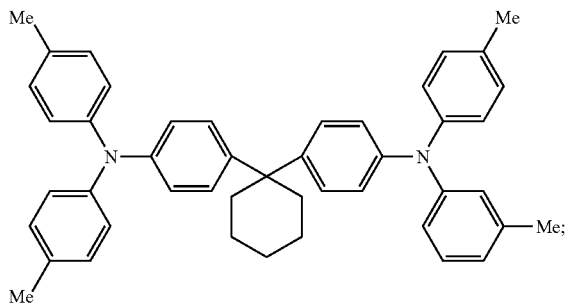

a stilbene based compound

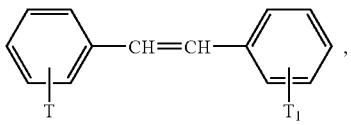

wherein T and $T_1$ stand for an organic radical;

a hydrazone based compound

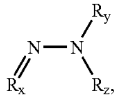

wherein Rx, Ry and Rz stand for an organic radical, and the like can be used.

Compounds to be used as a positive hole transporting material are not restricted to the above listed compounds. Any compound having a property of transporting positive holes can be used as a positive hole transporting material such as triazole derivatives, oxadiazole derivatives, imidazole derivatives, polyarylalkane derivatives, pyrazoline derivative, pyrazolone derivatives, phenylene diamine derivatives, arylamine derivatives, amino substituted chalcone derivatives, oxazole derivatives, stilbenylanthracene derivatives, fluorenone derivatives, hydrazone derivatives, stilbene derivatives, copolymers of aniline derivatives, PEDOT (poly(3,4-ethylenedioxy-thiophene)) and the derivatives thereof, electroconductive oligomers, particularly thiophene oligomers, porphyrin compounds, aromatic tertiary amine compounds, stilbenyl amine compounds etc.

Particularly, aromatic tertiary amine compounds such as N,N,N',N'-tetraphenyl-4,4'-diaminobiphenyl, N,N'-diphenyl-N,N'-bis(3-methylphenyl)-4,4'-diaminobiphenyl (TPD), 2,2'-bis(di-p-torylaminophenyl)propane, 1,1'-bis(4-di-torylaminophenyl)-4-phenylcyclohexane, bis(4-dimethylamino-2-methylphenyl)phenylmethane, bis(4-di-p-tolylaminophenyl)phenyl-methane, N,N'-diphenyl-N,N'-di(4-methoxyphenyl)-4,4'-diaminobiphenyl, N,N,N',N'-tetraphenyl-4,4'-diaminodiphenylether, 4,4'-bis (diphenylamino)quaterphenyl, N,N,N-tri(p-tolyl)amine, 4-(di-p-tolylamino)-4'-[4-(di-p-tolylamino)stilyl]stilbene, 4-N,N-diphenylamino-(2diphenylvinyl)benzene, 3-methoxy-4'-N,N-diphenylaminostilbene, N-phenylcarbazole etc. are used.

Furthermore, 4,4'-bis[N-(1-naphtyl)-N-phenylamino]biphenyl disclosed in U.S. Pat. No. 5,061,569 and the compounds disclosed in EP-A 508,562, in which three triphenylamine units are bound to a nitrogen atom, such as 4,4',4'''-tris [N-(3-methylphenyl)-N-phenylamino]triphenylamine, can be used.

A positive hole transporting layer can be formed by preparing an organic film containing at least one positive hole transporting material on the anode. The positive hole transporting layer can be formed by the vacuum deposition method, the spin-coating method, the casting method, the ink jet printing method, the LB method and the like. Of these methods, the vacuum deposition method, the spin-coating method and the casting method are particularly preferred in view of ease and cost.

In the case of using the vacuum deposition method, the conditions for deposition may be chosen in the same manner as described for the formation of a light emitting layer (see above). If it is desired to form a positive hole transporting layer comprising more than one positive hole transporting material, the coevaporation method can be employed using the desired compounds.

In the case of forming a positive hole transporting layer by the spin-coating method or the casting method, the layer can be formed under the conditions described for the formation of the light emitting layer (see above).

As in the case of forming the light emitting layer a smoother and more homogeneous positive hole transporting layer can be formed by using a solution containing a binder and at least one positive hole transporting material. The coating using such a solution can be performed in the same manner as described for the light emitting layer. Any polymer binder may be used, provided that it is soluble in the solvent in which the at least one positive hole transporting material is dissolved. Examples of appropriate polymer binders and of appropriate and preferred concentrations are given above when describing the formation of a light emitting layer.

The thickness of the positive hole transporting layer is preferably chosen In the range of from 0.5 to 1000 nm, preferably from 1 to 100 nm, more preferably from 2 to 50 nm.

As hole injection materials known organic hole transporting compounds such as metal-free phthalocyanine ($H_2Pc$), copper-phthalocyanine (Cu—Pc) and their derivatives as described, for example, in JP64-7635 can be used. Furthermore, some of the aromatic amines defined as hole transporting materials above, which have a lower ionisation potential than the hole transporting layer, can be used.

A hole injection layer can be formed by preparing an organic film containing at least one hole injection material between the anode layer and the hole transporting layer. The hole injection layer can be formed by the vacuum deposition method, the spin-coating method, the casting method, the LB method and the like. The thickness of the layer is preferably from 5 nm to 5 μm, and more preferably from 10 nm to 100 nm.

The electron transporting materials, which is for example a metal complex compound or a nitrogen-containing five-membered derivative, should have a high electron injection efficiency (from the cathode) and a high electron mobility. The following materials can be exemplified for electron transporting materials: lithium 8-hydroxyquinolinate, zinc bis(8-hydroxyquinolinate), copper bis(8-hydroxyquinolinate), manganese bis(8-hydroxyquinolinate), gallium tris(8-hydroxyquinolinate), tris(8-hydroxyquinolinato)-aluminum (III) and its derivatives, such as, for example, aluminum tris (2-methyl-8-hydroxyquinolinate), bis(10-hydroxybenzo[h]quinolinolato)beryllium(II) and its derivatives, zinc bis(10-hydroxybenzo[h]quinolinate), chlorogallium bis(2-methyl-8-quinolinate), gallium bis(2-methyl-8-quinolinate)(o-cresolate), aluminum bis(2-methyl-8-quinolinate)(1-naphtholate), gallium bis(2-methyl-8-quinolinate)(2-naphtholate), gallium bis(2-methyl-8-quinolinate)phenolate, zinc bis(o-(2-benzooxazolyl)phenolate), zinc bis(o-(2-benzothiazolyl)phenolate) and zinc bis(o-(2-benzotrizolyl)phenolate); oxadiazole derivatives, such as 2-(4-biphenyl)-5-(4-tert.-butylphenyl)-1,3,4-oxadiazole and 2,5-bis(1-naphthyl)-1,3,4-oxadiazole, and its dimer systems, such as 1,4-bis[2-(5-phenyloxadiazolyl)]benzene, 1,4-bis[2-(5-phenyloxadiazolyl)-4-tert-butylbenzene], 2,5-bis(1-phenyl)-1,3,4-oxadiazole, 2-(4'-tert-butylphenyl)-5-(4"-biphenyl)-1,3,4-oxadiazole, 1,3-bis(4-tert.-butylphenyl-1,3,4)oxadiazolyl)biphenylene and 1,3-bis(4-tert-butylphenyl-1,3,4-oxadiazolyl)phenylene, oxazole derivatives, dioxazole derivatives, thiazole derivatives, thiadiazole derivatives, triazole derivatives, such as 2,5-bis(1-phenyl)-1,3,4-oxazole, 1,4-bis(2-(4-methyl-5-phenyloxazolyl)benzene, 2,5-bis(1-phenyl)-1,3,4-thiazole, 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiazolyl)]benzene, 2-(4'-tert-butylphenyl)-5-(4"-biphenyl)-1,3,4-triazole, or 2,5-bis(1-naphthyl)-1,3,4-triazole and 1,4-bis[2-(5-phenyltriazolyl)]benzene, coumarine derivatives, imidazopyridine derivatives, phenanthroline derivatives or perylene tetracarboxylic acid derivatives disclosed in Appl. Phys. Lett. 48 (2) (1986) 183.

An electron transporting layer can be formed by preparing an organic film containing at least one electron transporting material on the hole transporting layer or on the light-emitting layer.

The electron transporting layer can be formed by the vacuum deposition method, the spin-coating method, the casting method, the LB method and the like.

It is preferred that the positive hole Inhibiting materials for a positive hole Inhibiting layer have high electron injection/transporting efficiency from the electron transporting layer to the light emission layer and also have higher ionisation potential than the light emitting layer to prevent the flowing out of positive holes from the light emitting layer to avoid a drop in luminescence efficiency.

As the positive hole inhibiting material known materials, such as Balq, TAZ and phenanthroline derivatives, e.g. bathocuproine (BCP), can be used:

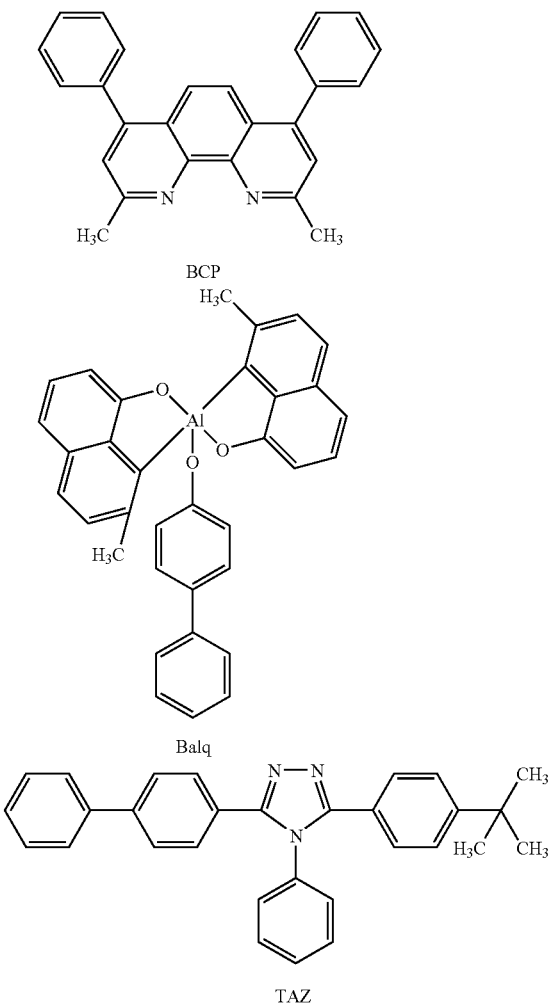

The positive hole inhibiting layer can be formed by preparing an organic film containing at least one positive hole inhibiting material between the electron transporting layer and the light-emitting layer. The positive hole inhibiting layer can be formed by the vacuum deposition method, the spin-coating method, the casting method, ink jet printing method, the LB method and the like. The thickness of the layer preferably is chosen within the range of from 5 nm to 2 μm, and more preferably, within the range of from 10 nm to 100 nm.

As in the case of forming a light emitting layer or a positive hole transporting layer, a smoother and more homogeneous electron transporting layer can be formed by using a solution containing a binder and at least one electron transporting material.

The thickness of an electron transporting layer is preferably chosen in the range of from 0.5 to 1000 nm, preferably from 1 to 100 nm, more preferably from 2 to 50 nm.

The hole-injecting material may be sensitivity-increased by incorporating an electron-accepting material, and the electron-injecting material may be sensitivity-increased by incorporating an electron-donating material.

In the organic EL device of the present invention, the light-emitting layer may contain, in addition to the light-emitting 2H-benzotriazole material of the present invention, at least one of other light-emitting material, other dopant, other hole-injecting material and other electron-injecting material. For improving the organic EL device of the present invention in the stability against temperature, humidity and ambient atmosphere, a protective layer may be formed on the surface of the device, or the device as a whole may be sealed with a silicone oil, or the like.

The electrically conductive material used for the cathode is suitably selected from those having a work function of smaller than 4 eV. The electrically conductive material includes magnesium, calcium, tin, lead, titanium, yttrium, lithium, ruthenium, manganese, aluminum and alloys of these, while the electrically conductive material shall not be limited to these. Examples of the alloys include magnesium/silver, magnesium/indium and lithium/aluminum, while the alloys shall not be limited to these. Each of the anode and the cathode may have a layer structure formed of two layers or more as required.

For the effective light emission of the organic EL device, at least one of the electrodes is desirably sufficiently transparent in the light emission wavelength region of the device. Further, the substrate is desirably transparent as well. The transparent electrode is produced from the above electrically conductive material by a deposition method or a sputtering method such that a predetermined light transmittance is secured. The electrode on the light emission surface side has for instance a light-transmittance of at least 10%. The substrate is not specially limited so long as it has adequate mechanical and thermal strength and has transparency. For example, it is selected from glass substrates and substrates of transparent resins such as a polyethylene substrate, a polyethylene terephthalate substrate, a polyether sulfone substrate and a polypropylene substrate.

In the organic EL device of the present invention, each layer can be formed by any one of dry film forming methods such as a vacuum deposition method, a sputtering method, a plasma method and an ion plating method and wet film forming methods such as a spin coating method, a dipping method and a flow coating method. The thickness of each layer is not specially limited, while each layer is required to have a proper thickness. When the layer thickness is too large, inefficiently, a high voltage is required to achieve predetermined emission of light. When the layer thickness is too small, the layer is liable to have a pinhole, etc., so that sufficient light emission brightness is hard to obtain when an electric field is applied. The thickness of each layer is for example in the range of from about 5 nm to about 10 μm, for Instance about 10 nm to about 0.2 μm.

In the wet film forming method, a material for forming an intended layer is dissolved or dispersed in a proper solvent such as ethanol, chloroform, tetrahydrofuran and dioxane, and a thin film is formed from the solution or dispersion. The solvent shall not be limited to the above solvents. For improving the film formability and preventing the occurrence of pinholes in any layer, the above solution or dispersion for forming the layer may contain a proper resin and a proper additive. The resin that can be used includes insulating resins such as polystyrene, polycarbonate, polyarylate, polyester, polyamide, polyurethane, polysulfone, polymethyl methacrylate, polymethyl acrylate and cellulose, copolymers of these, photoconductive resins such as poly-N-vinylcarbozole and polysilane, and electroconducting polymers such as polythiophene and polypyrrole. The above additive Includes an antioxidant, an ultraviolet absorbent and a plasticizer.

When the light-emitting benzotriazole material of the present invention is used in a light-emitting layer of an organic EL device, an organic EL device can be improved in organic EL device characteristics such as light emission efficiency and maximum light emission brightness. Further, the organic EL device of the present invention is remarkably stable against heat and electric current and gives a usable light emission brightness at a low actuation voltage. The problematic deterioration of conventional devices can be remarkably decreased.

The 2H-benzotriazole compounds of the formula

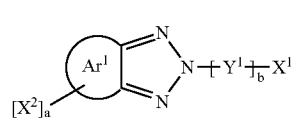

(I)

are new and form a further subject of the present invention, wherein a is 0, or 1, b is 0, or 1, $X^1$ is a group of formula

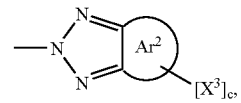

if b is 1, or $Y^3$, if b is 0, wherein c is 0, or 1

$X^2$ and $X^3$ are independently of each other a group of formula

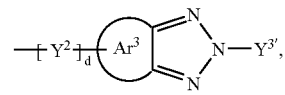

wherein d is 0, or 1, $Ar^1$, $Ar^2$, and $Ar^3$ are independently of each other aryl or heteroaryl, which can optionally be substituted, especially $C_6$-$C_{30}$aryl or a $C_2$-$C_{26}$heteroaryl, which can optionally be substituted, $Y^1$ and $Y^2$ are independently of each other a divalent linking group, and $Y^3$ and $Y^{3'}$ are independently of each other aryl or heteroaryl, which can optionally be substituted, especially $C_6$-$C_{30}$aryl or a $C_2$-$C_{26}$heteroaryl, which can optionally be substituted.

Among the compounds of formula IIa the following derivatives are preferred

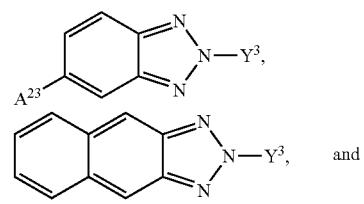

-continued

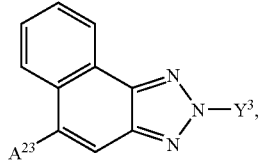

wherein $Y^3$ and $A^{23}$ are defined as above, wherein the compounds of formula IIb, IIc and IId are more preferred.

The following Examples illustrate the invention. In the Examples and throughout this application, the term light emitting material means the present 2H-benzotriazole compounds.

EXAMPLE 1

A1

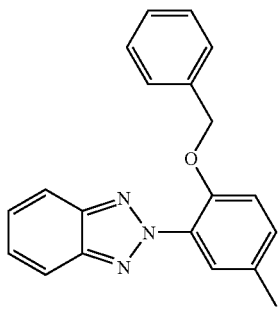

2-(2-Hydroxy-5-methylphenyl)benzotriazole, 10.0 g, 44.4 mmol, potassium carbonate, 12.0 g, 86.8 mmol., acetone, 150 ml and benzyl bromide, 5.3 ml, 7.6 g, 44.6 mmol., are placed in a 500 ml flask with a stir bar. The mixture is heated to 70° C. (reflux) with vigorous stirring for a total of 8 hours. The mixture is cooled to room temperature and filtered. Removal of volatiles in vacuo give a colorless oil. The product is crystallized from 5:1 hexanes:acetone (55 ml) to give a colorless solid. Yield: 12.86 g, 40.8 mmol, 92%. $T_m$=68° C. $^1$H NMR (ppm, CDCl$_3$): 7.97 (m, 2H), 7.53 (d, 1H), 7.42 (m, 2H), 7.24 (m, 6H), 7.04 (m, 1H), 5.14 (s, 2H), 2.35 (s, 3H). The material has a $\lambda_{max}$ emission of 407 nm, CIE (0.159, 0.037) in solution.

EXAMPLE 2

A2

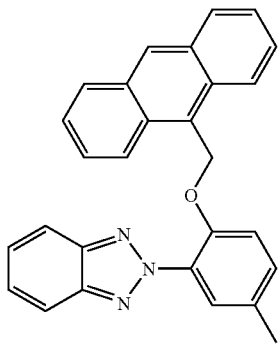

2-(2-Hydroxy-5-methylphenyl)benzotriazole, 2.64 g, 11.7 mmol., potassium carbonate, 2.0 g, 14 mmol, acetone, 60 ml and 9-chloromethylanthracene, 2.66 g, 11.7 mmol., are placed in a 250 ml flask with a stir bar. The mixture is heated to 70° C. (reflux) with vigorous stirring for a total of 32 hours. The mixture is cooled to room temperature and filtered. Removal of volatiles in vacuo give a slightly yellow solid, 4.83 g, 11.6 mmol, 99%. The product is triturated in hexanes: ethyl acetate, 5:2 overnight. Filtration and removal of volatiles in vacuo give a pale yellow solid. Yield: 3.53 g, 8.50 mmol, 73%. $T_m$=132° C. $^1$H NMR (ppm, CDCl$_3$): 8.41 (s, 1H), 8.26 (d, 2H), 7.94 (dd, 2H), 7.87 (m, 2H), 7.52 (s, 1H), 7.40 (m, 8H), 6.04 (s, 2H), 2.40 (s, 3H).

EXAMPLE 3

D1

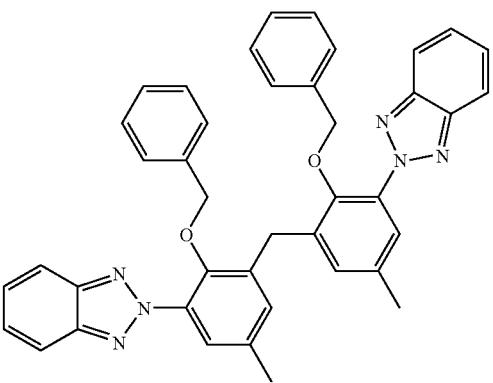

2,2'-Methylene bis-(6-(2H-benzotriazolyl)-4-methylphenol) (cf. U.S. Pat. No. 4,937,348), 3.00 g, 6.49 mmol, is slurried in DMF, 30 ml. The mixture is heated to 40° C. and NaOMe, 5.4 M in CH$_3$OH, 2.40 ml, 13 mmol, is added via syringe, forming an orange, homogeneous mixture. The temperature of the mixture is brought to 70° C. and benzyl bromide, 1.70 ml, 2.44 g, 14.3 mmol, is added via syringe. After 4 hours at 100° C., volatiles are removed in vacuo to give a semi-solid. The product is obtained using column chromatography, 19:1 hexanes:ethyl acetate. Yield: 3.32 g, 5.17 mmol, 80%. $T_m$=150° C. $^1$H NMR (ppm, CDCl$_3$): 7.90 (m, 4H), 7.42 (d, 2H), 7.38 (m, 4H), 7.08 (m, 6H), 6.97 (m, 4H), 6.90 (d, 2H), 4.34 (s, 4H), 2.26 (s, 6H).

EXAMPLE 4

A3

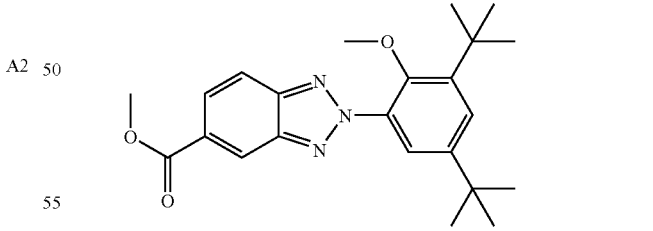

2-(5-carboxy-2H-benzotriazolyl)-4,6-di-tert-butylphenol, 5.00 g, 13.6 mmol., potassium carbonate, 5.64 g, 40.8 mmol, acetone, 80 ml, and DMF, 40 ml are placed in a 250 ml flask with a stir bar. Iodomethane, 4.2 ml, 9.6 g, 68 mmol, is added via syringe. The mixture is heated to 45° C. for 17 hours. Volatiles are removed in vacuo and the product is extracted with toluene. Filtration and removal of toluene in vacuo give a colorless solid in quantitative yield. 4.0 g of this material is chromatographed on silica using hexanes:ethyl acetate, 19:1, to give 3.8 g, 9.6 mmol, 95% (purification step) of product.

$T_m$=112° C. $^1$H NMR (ppm, CDCl$_3$): 8.82 (s, 1H), 8.09 (m, 2H), 7.56 (d, 1H), 7.51 (d, 1H), 4.02 (s, 3H), 3.10 (s, 3H), 1.48 (s, 9H), 1.37 (s, 9H). The material has a $\lambda_{max}$ emission of 445 nm, CIE (0.157, 0.132) in solution.

EXAMPLE 5

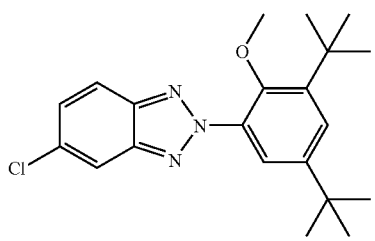

A4

2-(5-chloro-2H-benzotriazolyl)-4,6-di-tert-butylphenol, 30.06 g, 83.99 mmol, potassium carbonate, 23.3 g, 0.169 mol, acetone, 200 ml, and iodomethane, 26 ml, 59 g, 0.42 mol (added in portions), are heated to 45° C. for 3 days. The mixture is cooled and removed of volatiles in vacuo. The product is dissolved with toluene, filtered and removed of volatiles in vacuo to give a colorless solid. Yield, 31.18 g, 83.84 mmol., 99.8%. $T_m$=224° C. $^1$H NMR (ppm, CDCl$_3$): 8.16 (d, 1H), 8.12 (d, 1H), 7.69 (d, 1H), 7.63 (d, 1H), 7.57 (dd, 1H), 3.25 (s, 3H), 1.62 (s, 9H), 1.51 (s, 9H).

EXAMPLE 6

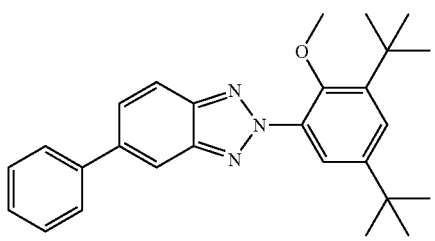

A5

The compound from example 5, 2.00 g, 5.38 mmol, potassium carbonate, 2.23 g, 16.1 mmol., and phenylboronic acid, 0.98 g, 8.04 mmol, are slurried in toluene, 30 ml, and heated to 110° C. under argon. Allyl, tricyclohexylphosphine palladium chloride (cf. WO01/16057), 20 mg, is added, followed by heating at 110° C. for 24 hours. The mixture is cooled to room temperature and filtered through a pad of silica and washed with toluene. Volatiles are removed in vacuo and the crude material is triturated in pentane, 20 ml, for 15 hours to give a clean product. Yield, 1.53 g, 3.70 mmol, 69%. $T_m$=152° C. $^1$H NMR (ppm, CDCl$_3$): 8.28 (s, 1H), 8.18 (d, 1H), 7.82 (m, 3H), 7.62 (m, 4H), 7.37 (m, 1H), 3.23 (s, 3H), 1.58 (s, 9H), 1.46 (s, 9H). The material has a $\lambda_{max}$ emission of 413 nm, CIE (0.157, 0.053) in solution.

EXAMPLE 7

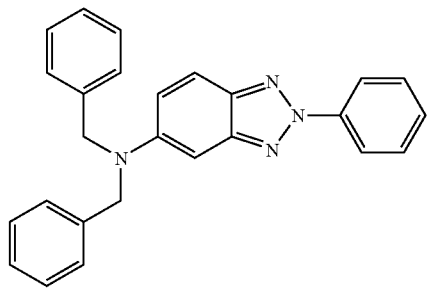

A6

5-Amino-2-phenyl-2H-benzotriazole (Kehrmann, et. al., Chem. Ber. 1892, 25, 899.), 2.10 g, 10.0 mmol, potassium carbonate, 4.15 g, 30.0 mmole, and benzyl bromide, 3.42 g, 20.0 mmol, were placed in a 100 ml flask with DMF, 30 ml, and a stir bar. The mixture is heated to 100° C. for 15 hours. The flask is cooled and ethyl acetate is added. The solution is extracted and washed with water (5×250 ml) to remove DMF. Drying with MgSO$_4$, filtration and removal of volatiles in vacuo give a green-yellow semi-solid. The product is purified by trituration in hexanes:ethyl acetate, 4:1, 30 ml, followed by crystallization from toluene, 20 ml. Yield, 2.12 g, 5.43 mmol., 54%. $T_m$=158° C. $^1$H NMR (ppm, CDCl$_3$): 8.24 (d, 2H), 7.73 (d, 1H), 7.49 (t, 2H), 7.29 (m, 1H), 7.17 (dd, 1H), 6.91 (d, 1H), 4.75 (s, 4H). The material has a $\lambda_{max}$ emission of 455 nm and 497 nm in solution.

EXAMPLE 8

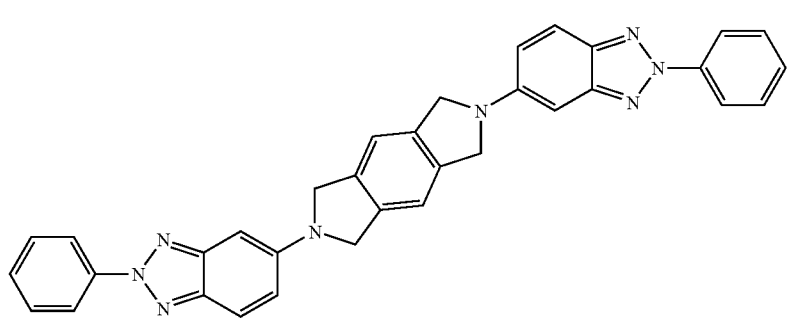

E1

5-Amino-2-phenyl-2H-benzotriazole (Kehrmann, et. al., *Chem. Ber.* 1892, 25, 899.), 2.00 g, 9.51 mmol, potassium carbonate, 3.47 g, 25.1 mmol, and 1,2,4,5-tetrakisbromomethylbenzene, 2.14 g, 4.76 mmol, are placed in a 100 ml flask with a stir bar. DMF, 40 ml, is added and the mixture is heated to 100° C. After 4 hours, a thick yellow precipitate is found and TLC showed only one component with a very low $R_f$ (1:1 hexanes:ethyl acetate). The flask is cooled and water, 30 ml, is added. The product is filtered and washed several times with water, then with methanol. Remaining volatiles are removed in vacuo to give a yellow solid. Yield, 2.49 g, 4.56 mmol, 96%. $T_m$=364° C.; $T_g$=167° C. MS (EI): 546 (M$^+$).

EXAMPLE 9

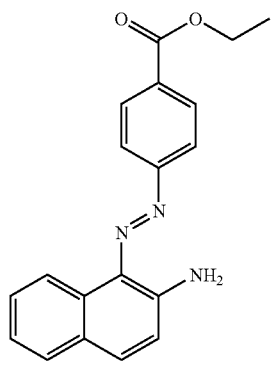

a) Benzocaine, 23.00 g, 139.2 mmol, is slurried in water, 400 ml, and concentrated HCl, 29 ml, 0.35 mol, is added, forming a homogeneous solution. The mixture is cooled to 0° C. and sodium nitrite, 10.09 g, 146.2 mmol., in water, 50 ml, is added dropwise. After 40 minutes, sulfamic acid, 3.0 g, 31 mmol, in water, 20 ml, is slowly added to destroy excess nitrite. The diazonium salt is cannulated into a 2.5 l reactor containing 1-naphthylamine-2-sulfonic acid, 31.08 g, 139.2 mmol, sodium carbonate, 29.5 g, 0.278 mol, in water, 800 ml at 0° C. After 2 hours at 0 to 5° C., the product is filtered and washed with water (2×300 ml) to form a red solid. TLC shows one major spot and a minor impurity. All was used for b).

B1

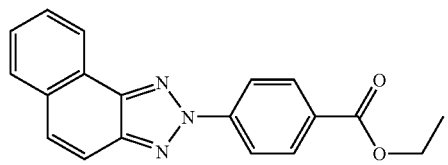

b) The product from a) and copper(II) acetate, 0.25 g, 1.38 mmol, are slurried in tert-amyl alcohol. Upon heating to 80° C., the mixture become homogeneous and tert-butyl hydroperoxide, 100 ml, 70 g, 0.78 mol, is added over 2 days. The mixture is cooled and filtered to remove the product. Washing with tert-amyl alcohol and removal of volatiles in vacuo give a pink solid. Yield, 27.46 g, 86.53 mmol, 62%. $T_m$=161° C. $^1$H NMR (ppm, CDCl$_3$): 8.42 (d, 1H), 8.23 (d, 2H), 8.01 (d, 2H), 7.66 (d, 1H), 7.55 (m, 2H), 7.45 (m, 2H), 4.21 (q, 2H), 1.22 (t, 3H).

EXAMPLE 10

B2

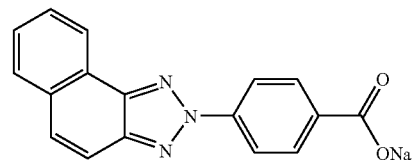

The product from example 9 is slurried in ethanol:water, 1:1, 700 ml, and sodium hydroxide, 6.94 g, 0.174 mol, is added. The mixture is heated to reflux (105° C. external) for 4 hours. The flask is cooled to 70° C. and filtered to give a light brown solution of the product. Upon cooling to room temperature overnight, crystals form. The product is filtered, washed with ethanol:water, 1:1, 50 ml, and dried using high vacuum. This material is used for example 11 without purification. Yield: 21.22 g, 68.17 mmol., 79%.

EXAMPLE 11

B3

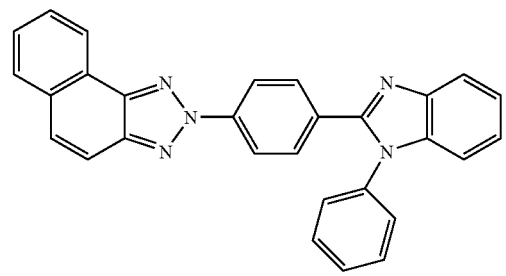

The product from example 10, 3.00 g, 9.64 mmol, is slurried at room temperature in dichloromethane, 40 ml, containing a few drops of DMF. Thionyl chloride, 2.4 ml, 3.9 g, 33 mmol, is added via syringe, causing a precipitate to form along with an exotherm. The flask is heated to an external temperature of 53° C. for 5 hours, followed by cooling to room temperature. Volatiles are removed In vacuo to give a pale brown solid. A solution of N-phenyl-1,2-phenylenediamine, 1.78 g, 9.66 mol., in N-methylpyrrolidinone, 20 ml, is added dropwise to the solid under argon. After 30 minutes at room temperature, the mixture is heated to 60° C. for 2 hours. The product is isolated by pouring into water, filtration and washing with water as well as methanol, 25 ml. High vacuum is used to isolate the material. The material is heated to 260° C. under vacuum (100 mbar) for 3 hours to form a melt of the product. After cooling to room temperature, the product is extracted with dichloromethane and filtered through a silica pad. Solvent is removed in vacuo to give a near colorless solid that is one spot by TLC (hexanes:ethyl acetate, 1:1). Yield, 3.03 g, 6.93 mmol, 72%. The material is purified by trituration in MeOH, 25 ml, overnight. Filtration and removal of volatiles in vacuo give a colorless solid. Yield, 2.48 g, 5.67 mmol, 59%. $T_m$=208° C., $T_g$=75° C. MS (EI): 437 (M$^+$). $^1$H NMR (ppm, CDCl$_3$): 8.54 (d, 1H), 8.27 (d, 2H), 7.84 (m, 2H), 7.71 (m, 2H), 7.67 (d, 1H), 7.58 (m, 3H), 7.46 (m, 3H), 7.32 (m, 3H), 7.23 (m, 2H).

EXAMPLE 12

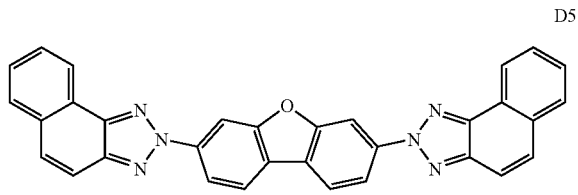

D5

3,7-Diaminodibenzofuran (Nimura, S., et. al. *J. Phys. Chem. A* 1997, 101, 2083.), 10.0 g, 50.4 mmol., water, 150 ml, and concentrated HCl, 25 ml, 0.30 mol., are placed in a 500 ml reactor. Sodium nitrite, 7.00 g, 0.101 mol. in water, 28 ml, is added dropwise at 0° C. DMF, 45 ml, is added slow enough to not let the temperature above 5IC. After 10 minutes, the diazonium salt is added dropwise to a solution of 2-naphthylamine, 14.4 g, 0.101 mol. in water, 100 ml, DMF, 50 ml, and HCl, 10 ml, 0.12 mol, to give a dark mixture. Sodium acetate trihydrate, 40 g, 0.29 mol., is added to the reaction at 0° C., followed by stirring for 2 hours at room temperature. The bis-azo intermediate is filtered and washed with water.

The product is placed in a 1 l reactor with pyridine, 225 ml, and copper(II) acetate monohydrate, 50 g, 0.25 mol. The mixture is heated to reflux for 6 hours and then cooled to room temperature. The beige product is filtered and washed with water, 7×150 ml, and methanol, 2×50 ml. Volatiles are removed in vacuo. The compound is purified by dissolving in hot trichlorobenzene, filtering through activated carbon (while hot) and cooling to room temperature to give yellow crystals. Yield, 13.15 g, 26.2 mmol., 52%. T$_m$=348° C. MS (EI): 502 (M$^+$).

EXAMPLE 13

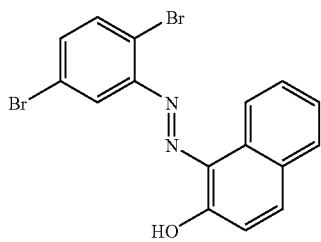

a) 2,5-dibromoaniline, 19.71 g, 78.5 mmol, is dissolved in EtOH, 130 ml, at room temperature. While stirring, H$_2$SO$_4$, 4.2 ml, 7.7 g, 79 mmol, is added via syringe, causing a precipitate to form. Volatiles are removed in vacuo to give a beige powder.

The anilinium sulfate salt above, 26.00 g, 77.0 mmol, is slurried in water, 200 ml, and HCl, 5 ml, 60 mmol, at 0° C. Sodium nitrite, 5.31 g, 77.0 mmol, in water, 30 ml, is added dropwise.

The reaction is stirred for 2 hours at 0° C. The diazonium salt solution is added portion-wise to a solution of 2-naphthol, 11.1 g, 77.0 mmol, in ethanol, 450 ml, also at 0° C. The orange mixture is stirred for 3 hours and warmed to room temperature. The product is filtered and washed with water (3×200 ml) and dried under vacuum. The product is purified by trituration in 19:1 hexanes:ethyl acetate (200 ml), filtered and dried in vacuo to give an orange solid. Yield, 28.13 g, 69.27 mmol, 90%. T$_{dec}$=170° C. $^1$H NMR (ppm, CDCl$_3$): 8.63 (d, 1H), 8.32 (d, 1H), 7.85 (d, 1H), 7.72 (m, 2H), 7.62 (d, 1H), 7.57 (t, 1H), 7.35 (dd, 1H), 6.93 (d, 1H).

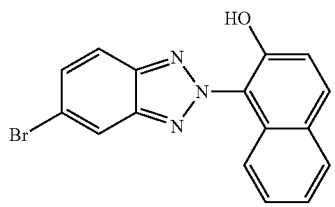

A7 b) The product from a), 28.13 g, 69.27 mmol, sodium azide, 4.50 g, 69.3 mmol, and copper(1) bromide, 0.10 g, 0.69 mmol, are placed in a 500 ml flask with a stir bar and DMF, 200 ml. The mixture is heated to 80° C. for 2 hours and cooled to room temperature. The solution Is poured into water, 500 ml, and washed with water (4×500 ml). Removal of volatiles in vacuo give a brown solid, pure by TLC (1:1 hexanes:ethyl acetate). Yield, 21.1 g, 62.0 mmol, 90%. $^1$H NMR (ppm, CDCl$_3$): 8.62 (d, 1H), 8.22 (s, 1H), 7.90 (m, 3H), 7.60 (m, 2H), 7.41 (m, 2H).

EXAMPLE 14

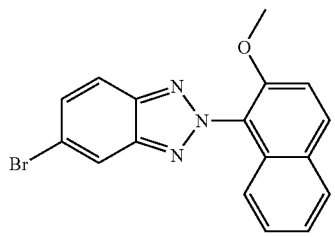

A8

The product from example 13, 20.7 g, 60.9 mmol, and potassium carbonate, 16.9 g, 122 mmol, are placed in a 500 ml flask with a stir bar and DMF, 200 ml. Iodomethane, 7.8 ml, 17.8 g, 122 mmol, is added via syringe. The flask is heated to 50° C. (external) for 3 hours. Volatiles are removed in vacuo and the product is extracted with toluene:water (1:1, 1l). The organic phase is separated and dried. Filtration and removal of volatiles in vacuo give a brown solid, pure by TLC and NMR. Yield, 17.2 g, 48.6 mmol, 80%. T$_m$=116° C. $^1$H NMR (ppm, CDCl$_3$): 8.22 (s, 1H), 8.06 (d, 1H), 7.92 (d, 1H), 7.87 (m, 1H), 7.56 (dd, 1H), 7.41 (m, 3H), 6.92 (m, 1H), 3.88 (s, 3H).

EXAMPLE 15

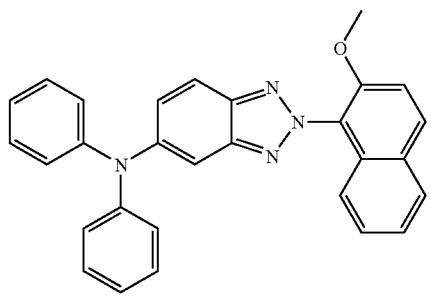

A9

The product from example 14, 5.00 g, 14.1 mmol, diphenylamine, 2.39 g, 14.1 mmol, sodium tert-butoxide, 2.71 g, 28.2 mmol, tris-(dibenzylidineacetone) dipalladium(0), 129 mg, 0.141 mmol, and bis-(diphenylphosphino) ferrocene, 156 mg, 0.281 mmol, are placed in a 250 ml flask with a stir bar. Toluene, 100 ml, is added and the mixture is heated to 100° C. for 24 hours. The product is adsorbed onto alumina and chromatographed using hexanes:ethyl acetate (15:1). The product is further purified via sublimation. $T_m$=214° C., $T_g$=78° C. MS (EI): 442 (M+). $^1$H NMR (ppm, CDCl$_3$): 8.14 (d, 1H), 7.94 (d, 2H), 7.51 (m, 4H), 7.38 (m, 5H), 7.28 (m, 4H), 7.16 (m, 3H), 4.00 (s, 3H). The material has a $\lambda_{max}$ emission of 478 nm in solution.

EXAMPLE 16

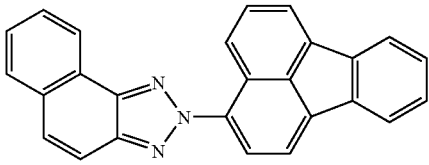

B7

3-Aminofluoranthene, 10.85 g, 49.94 mmol, is suspended in water, 50 ml, and HCl, 12 M, 10 ml, 0.12 mol, at 0° C. Sodium nitrite, 3.50 g, 50.7 mmol, In water, 10 ml, is added dropwise over 15 minutes. After 30 minutes at 0° C., the red-brown solution is filtered. Tobias acid (2-naphthylamine-1-sulfonic acid), 11.15 g, 49.96 mmol, is dissolved in pyridine, 50 ml, and cooled to 0° C. The diazonium salt solution is then added dropwise over 30 minutes at 0° C. After 2 hours, the suspension is filtered, washed with water and dried in vacuo to give a purple-red solid.

The material, 15.6 g, 42.0 mmol, is heated in pyridine, 250 ml, to 60° C. in a 1 l reactor. Copper(II) sulfate pentahydrate, 26.4 g, 0.105 mol, in water, 100 ml, is added dropwise to the azo compound. The temperature is then raised to 90° C. for 4 hours. The mixture is cooled to room temperature and filtered to give a pale brown solid. The compound is purified by crystallization. Yield, 7.9 g, 21.4 mmol, 51%. $T_m$=155° C. MS (APCI): 370.1 (M+1). The material has a $\lambda_{max}$ emission of 478 nm in solution.

EXAMPLE 17

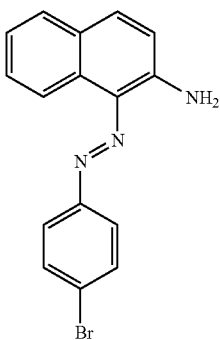

a) 4-Bromoaniline, 23.63 g, 137.4 mmol, is dissolved in water, 250 ml, using HCl, 31 ml, 372 mmol. The mixture i cooled to 0° C. and sodium nitrite, 9.48 g, 137 mmol, in water, 30 ml, is added dropwise over 30 minutes. After 45 minutes, the diazonium salt is added via cannula to a mixture of Tobias acid, 30.66 g, 137.4 mmol, and sodium carbonate, 25.1 g, 234 mmol, in water, 600 ml, at 0° C. After 2 hours, the red precipitate is filtered and washed with water (2×300 ml). The product is dried in vacuo to give a red solid. The compound is triturated in methanol, 175 ml, overnight. Filtration and removal of volatiles in vacuo give a red solid, pure by TLC. The red dye is used directly for the next step. MS (EI): 325 (M+). $^1$H NMR (ppm, CDCl$_3$): 8.74 (d, 1H), 7.68 (d, 2H), 7.59 (d, 2H), 7.53 (m, 2H), 7.47 (t, 1H), 7.27 (t, 1H), 6.77 (d, 1H).

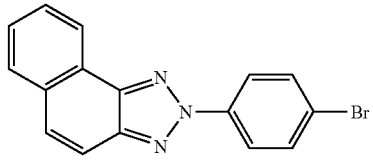

B4 b) The product from a), 10.00 g, 30.66 mmol, and copper (II) acetate, 50 mg, 0.28 mmol, are placed in a 250 ml flask with a stir bar. tert-Amyl alcohol, 100 ml, is added and the mixture is heated to 80° C. tert-Butyl hydroperoxide, 13.7 ml, 100 mmol, is slowly added and the reaction is monitored by TLC. The flask is cooled to room temperature and the product is filtered. Washing with tert-amyl alcohol and removal of volatiles in vacuo give a pale rose solid. Yield, 7.82 g, 24.1 mmol, 79%. MS (EI): 323 (M+). $^1$H NMR (ppm, CDCl$_3$): 8.49 (d, 1H), 8.15 (d, 2H), 7.76 (d, 1H), 7.64 (m, 2H), 7.55 (m, 4H).

EXAMPLE 18

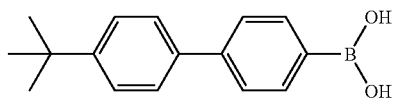

a) Magnesium turnings, 1.67 g, 68.7 mmol, are dry stirred under argon for one hour. Ether, 32 ml, is added, followed by 2 drops of dibromoethane. 4-Bromo-4'-tert-butylbiphenyl (Murphy, S., et. al. *J. Org. Chem.* 1995, 60, 2411.) 10.0 g, 34.6 mmol, in ether, 20 ml, and THF, 25 ml, is added dropwise over 1 hour. The mixture is refluxed for 2 hours at 37° C. In a separate flask, triisopropylborate, 9.4 ml, 7.7 g, 41 mmol, and THF, 30 ml, are cooled to −78° C. under argon. The above Grignard reagent is added via cannula and the reaction is allowed to stir at −78° C. for 1 hour. The flask is warmed to room temperature and stirred for an additional hour. The mixture is poured into a flask containing HCl, water and is stirred for 2 hours. The beige product is filtered and washed with water. Removal of volatiles in vacuo give an off-white solid. Yield, 5.67 g, 22.3 mmol, 64%. $T_m$=192° C. $^1$H NMR (ppm, (CD$_3$)$_2$SO): 7.80 (d, 2H), 7.55 (two overlapping doublets, 4H), 7.41 (d, 2H), 1.25 (s, 9H).

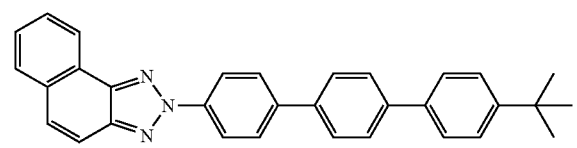

B5 b) The product from a), 2.00 g, 6.13 mmol, the product from example 19, 2.54 g, 9.99 mmol, potassium carbonate, 2.36 g, 17.1 mmol, and toluene, 50 ml, are stirred under argon for 30 minutes. Allyl, tricyclohexylphosphinyl palladium chloride (WO01116057), 40 mg, is added, followed by heating at 110° C. for 24 hours. The mixture is cooled to room temperature and adsorbed onto silica gel. The product is purified by column chromatography using hexanes:ethyl acetate, 9:1, to give a tan solid, 0.90 g, 1.98 mmol, 32%. $T_m$=245° C. The product has a $\lambda_{max}$ emission of 414 nm in solution, with a quantum efficiency of 70%.

APPLICATION EXAMPLE 1

Device

The following device structure is prepared:
ITO (anode, ITO is indium tin oxide)
CuPC (copper phthalocyanine; hole Injection material)
NPD (4,4'-bis-(1-naphthyl-phenylamino)biphenyl; hole transporting material)
DPVBi (4,4'-bis-(2,2-diphenyl-1-vinyl)biphenyl) (host)/ Compound of example 16 (2.6%, guest)
Alq3 (tris-8-quinolinato aluminum; electron transporting material)
LiF/Al (cathode).

Using this device structure, a maximum brightness of 816 cd/m² was observed at 9V (0.89 cd/A) with an emission $\lambda_{max}$ at 489 nm, similar to the guest material in solution.

APPLICATION EXAMPLE 2

Device

The following device structure is prepared:
ITO (anode, ITO is indium tin oxide)
CuPC (copper phthalocyanine; hole Injection material)
NPD (4,4'-bis-(1-naphthyl-phenylamino)biphenyl; hole transporting material)
DPVBi (4,4'-bis-(2,2-diphenyl-1-vinyl)biphenyl) (host)/ Compound of example 15 (2.2%, guest)
Alq3 (tris-8-quinolinato aluminum; electron transporting material)
LiF/Al (cathode).

Using this device structure, a maximum brightness of 3120 cd/m² was observed at 11V (1.8 cd/A) with an emission 4 at 493 nm, similar to the guest material in solution.

APPLICATION EXAMPLE 3

Device

The following device structure is prepared:
ITO (anode, ITO is indium tin oxide)
CuPC (copper phthalocyanine; hole injection material)
NPD (4,4'-bis-(1-naphthyl-phenylamino)biphenyl; hole transporting material)
Compound of example 12
Alq3 (tris-8-quinolinato aluminum; electron transporting material)
LiF/Al (cathode).

Using this device structure, a maximum brightness of 1230 cd/m² was observed at 15V (1.1 cd/A) with an emission $\lambda_{max}$ at 471 nm.

APPLICATION EXAMPLE 4

Device

The following device structure is prepared:
ITO (anode, ITO is Indium tin oxide)
CuPC (copper phthalocyanine; hole injection material)
NPD (4,4'-bis-(1-naphthyl-phenylamino)biphenyl; hole transporting material)
Compound of example 11
Alq3 (tris-8-quinolinato aluminum; electron transporting material)
LiF/Al (cathode).

Using this device structure, a maximum brightness of 720 cd/m² was observed at 10V (0.71 cd/A) with an emission $\lambda_{max}$ at 432 nm.

APPLICATION EXAMPLE 5

Device

The following device structure is prepared:
ITO (anode, ITO is indium fin oxide)
CuPC (copper phthalocyanine; hole injection material)
NPD (4,4'-bis-(1-naphthyl-phenylamino)biphenyl; hole transporting material)
DPVBi (4,4'-bis-(2,2-diphenyl-1-vinyl)biphenyl) (host)/ Compound of example 7 (3.1%, guest)
Alq3 (tris-8-quinolinato aluminum; electron transporting material)
LiF/Al (cathode).

Using this device structure, a maximum brightness of 4130 cd/m² was observed at 14V (2.1 cd/A) with an emission $\lambda_{max}$ at 461 nm, similar to the guest material in solution.

The organic EL device obtained in the Example of the present invention show an excellent light emission brightness and achieved a high light emission efficiency. When the organic EL devices obtained in the above Examples are allowed to continuously emit light at 3 (mA/cm²), all the organic EL devices remain stable. Since the light-emitting materials of the present invention have a very high fluorescence quantum efficiency, the organic EL devices using the light-emitting materials achieved light emission with a high brightness in a low electric current applied region, and when the light-emitting layer additionally uses a doping material, the organic EL devices are improved in maximum light emission brightness and maximum light emission efficiency. Further, by adding a doping material having a different fluorescent color to the light-emitting material of the present invention, there are obtained light-emitting devices having a different light emission color.

The organic EL devices of the present invention accomplish improvements in light emission efficiency and light emission brightness and a longer device life, and does not impose any limitations on a light-emitting material, a dopant, a hole-injecting material, an electron-injecting material, a sensitizer, a resin and an electrode material used in combination and the method of producing the device.

The organic EL device using the material of the present invention as a light-emitting material achieves light emission having a high brightness with a high light emission efficiency and a longer life as compared with conventional devices. According to the light-emitting material of the present invention and the organic EL device of the present invention, there can be achieved an organic EL device having a high brightness, a high light emission efficiency and a long life.

The invention claimed is:

1. An electroluminescent device, comprising a 2H-benzotriazole compound of the formula

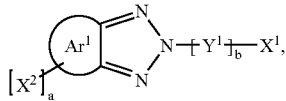
(I)

where
a is 0, or 1,
b is 0, or 1,
with the proviso that if b is 1, then a is 1,
$X^1$ is a group of formula

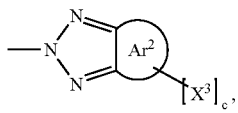

if b is 1,
or $Y^3$, if b is 0,
wherein
c is 0, or 1
$X^2$ and $X^3$ are independently of each other a group of formula

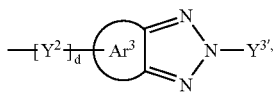

wherein d is 0, or 1,
$Ar^1$, $Ar^2$, and $Ar^3$ are independently of each other $C_6$-$C_{30}$aryl or a $C_2$-$C_{26}$heteroaryl, which can optionally be substituted,
$Y^1$ and $Y^2$ are independently of each other a divalent linking group selected from the group consisting of

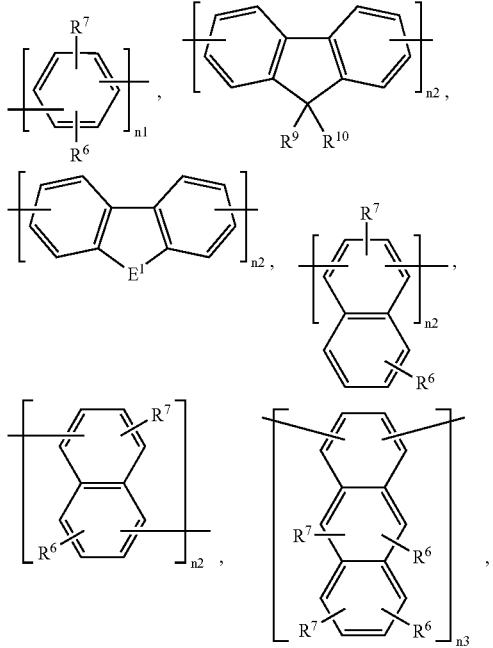

-continued

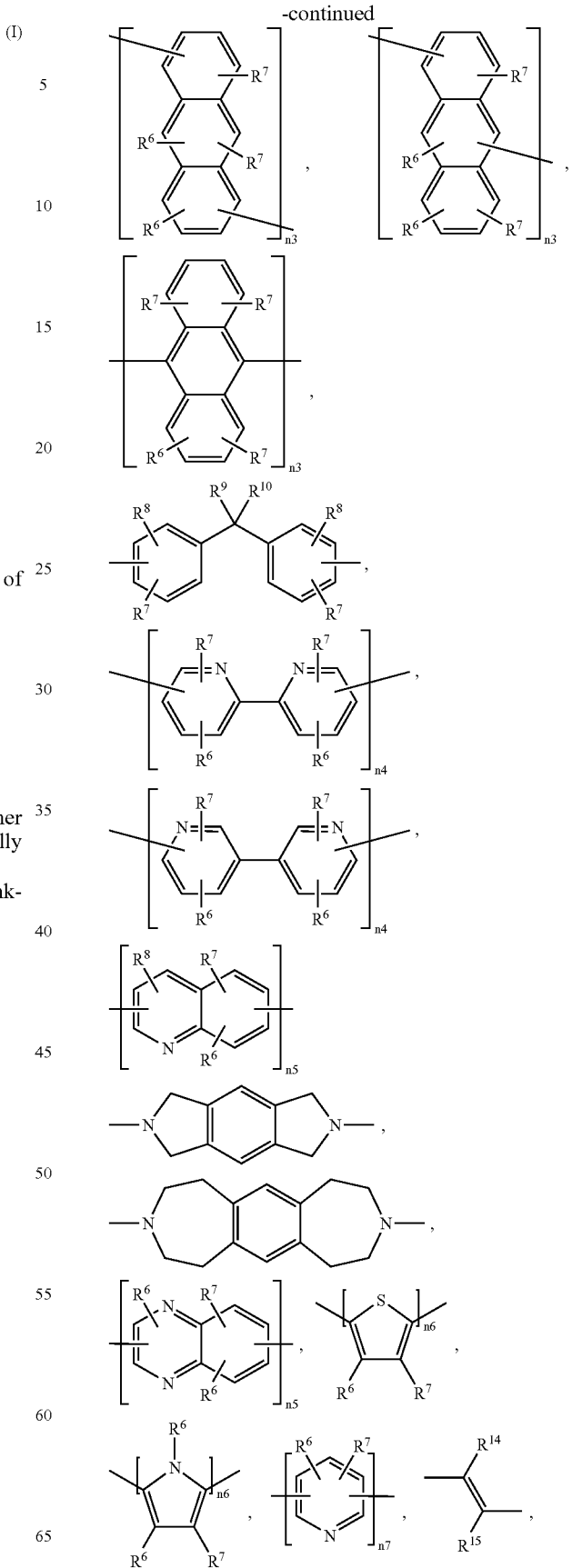

-continued

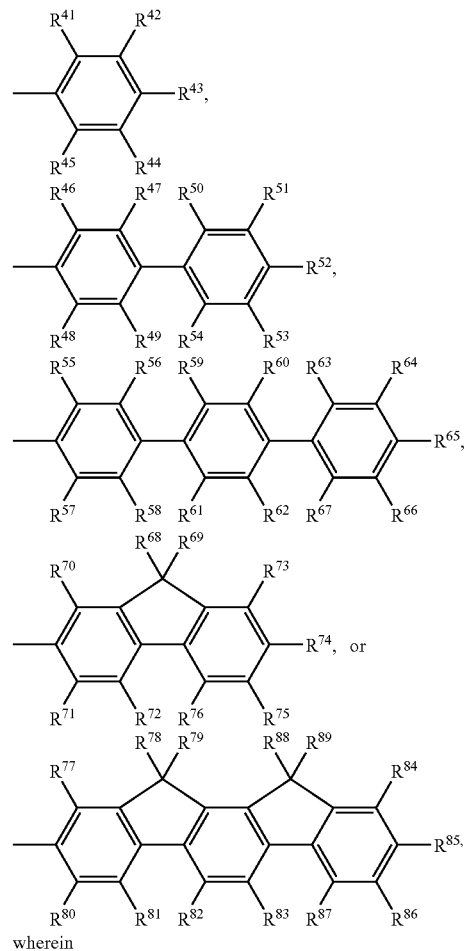

n1, n2, n3, n4, n5, n6 and n7 are 1, 2, or 3, $E^1$ is —S—, —O—, or —NR$^{25'}$—, wherein R$^{25'}$ is $C_1$-$C_{24}$alkyl, or $C_6$-$C_{10}$aryl, $R^6$ and $R^7$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_5$-$C_{12}$cycloalkyl, $C_5$-$C_{12}$cycloalkyl which is substituted by E and/or interrupted by S—, —O—, or —NR$^{25}$—, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7C_{25}$aralkyl, which is substituted by E, $C_7$-$C_{25}$aralkoxy, $C_7$-$C_{25}$aralkoxy which is substituted by E, or —CO—R$^{28}$, $R^8$ is $C_1$-$C_{24}$alkyl, $C_1$-$C_{24}$alkyl which is substituted by E and/or interrupted by D, $C_6$-$C_{24}$ aryl, or $C_7$-$C_{25}$aralkyl, $R^9$ and $R^{10}$ are independently of each other $C_1$-$C_{24}$alkyl, $C_1$-$C_{24}$alkyl which is substituted by E and/or interrupted by D, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, or $C_7$-$C_{25}$aralkyl, or $R^9$ and $R^{10}$ form a five- or six-membered ring, $R^{14}$ and $R^{15}$ are independently of each other H, $C_1$-$C_{24}$alkyl, $C_1$-$C_{24}$alkyl which is substituted by E and/or interrupted by D, $C_6$-$C_{24}$aryl, $C_6$-$C_{24}$aryl which is substituted by E, $C_2$-$C_{20}$heteroaryl, or $C_2$-$C_{20}$heteroaryl which is substituted by E, D is —CO—, —COO—, —S—, —SO—, —SO$_2$—, —O—, —NR$^{25}$—, —SiR$^{30}$R$^{31}$—, —POR$^{32}$—, —CR$^{23}$=CR$^{24}$—, or —C≡C—, and E is —OR$^{29}$, —SR$^{29}$, —NR$^{25}$R$^{26}$, —COR$^{28}$, —COOR$^{27}$, —CONR$^{25}$R$^{26}$, —CN, —OCOOR$^{27}$, or halogen, wherein $R^{23}$, $R^{24}$, $R^{25}$ and $R^{26}$ are independently of each other H, $C_6$-$C_{18}$aryl, $C_6$-$C_{18}$aryl which is substituted by $C_1$-$C_{24}$alkyl, $C_1$-$C_{24}$alkoxy, $C_1$-$C_{24}$alkyl, or $C_1$-$C_{24}$alkyl which is interrupted by —O—, or $R^{25}$ and $R^{26}$ together form a five or six membered ring, $R^{27}$ and $R^{28}$ are independently of each other H, $C_6$-$C_{18}$aryl, $C_6$-$C_{18}$aryl which is substituted by $C_1$-$C_{24}$alkyl, or $C_1$-$C_{24}$alkoxy, $C_1$-$C_{24}$alkyl, or $C_1$-$C_{24}$alkyl which is interrupted by —O—, $R^{29}$ is H, $C_6$-$C_{18}$aryl, $C_6$-$C_{18}$aryl, which is substituted by $C_1$-$C_{24}$alkyl, $C_1$-$C_{24}$alkoxy, $C_1$-$C_{24}$alkyl, or $C_1$-$C_{24}$alkyl which is interrupted by —O—, $R^{30}$ and $R^{31}$ are independently of each other $C_1$-$C_{24}$alkyl, $C_6$-$C_{18}$aryl, or $C_6$-$C_{18}$aryl, which is substituted by $C_1$-$C_{24}$alkyl, and $R^{32}$ is $C_1$-$C_{24}$alkyl, $C_6$-$C_{18}$aryl, or $C_8$-$C_{18}$aryl, which is substituted by $C_1$-$C_{24}$alkyl, and $Y^3$ and $Y^{3'}$ are independently of each other a group of formula wherein $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{70}$, $R^{71}$, $R^{72}$, $R^{73}$, $R^{74}$, $R^{75}$, $R^{76}$, $R^{77}$, $R^{80}$, $R^{81}$, $R^{82}$, $R^{83}$, $R^{84}$, $R^{85}$, $R^{86}$, and $R^{87}$ are independently of each other H, $C_1$-$C_{24}$alkyl, which is optionally substituted by E and/or interrupted by D, $C_1$-$C_{24}$alkenyl, which is optionally substituted by E, $C_5$-$C_{12}$cycloalkyl, which is optionally substituted by E, $C_5$-$C_{12}$cycloalkoxy, which is optionally substituted by E, $C_6$-$C_{18}$aryl, which is optionally substituted by E, $C_1$-$C_{24}$alkoxy, which is optionally substituted by E and/or interrupted by D, $C_6$-$C_{18}$aryloxy, which is optionally substituted by E, $C_7$-$C_{18}$arylalkoxy, which is optionally substituted by E, $C_1$-$C_{24}$alkylthio, which is optionally substituted by E and/or interrupted by D, $C_1$-$C_{24}$alkylselenium, which is optionally substituted by E and/or interrupted by D, $C_1$-$C_{24}$alkyltellurium, which is optionally substituted by E and/or interrupted by D, $C_2$-$C_{20}$heteroaryl which is substituted by E, or $C_6$-$C_{18}$aralkyl, which is optionally substituted by E, or two groups $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{70}$, $R^{71}$, $R^{72}$, $R^{73}$, $R^{74}$, $R^{75}$, $R^{76}$, $R^{77}$, $R^{80}$, $R^{81}$, $R^{82}$, $R^{83}$, $R^{84}$, $R^{85}$, $R^{86}$, and $R^{87}$, which are neighbouring to each other, are a group

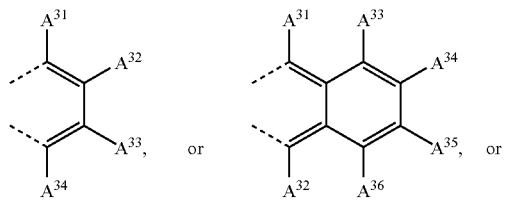

wherein $A^{90}$, $A^{91}$, $A^{92}$, $A^{93}$, $A^{94}$, $A^{95}$, $A^{96}$ and $A^{97}$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_5$-$C_{12}$cycloalkyl, $C_5$-$C_{12}$cycloalkyl which is substituted by E and/or interrupted by S—, —O—, or —NR$^{25}$—, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by E, $C_7$-$C_{25}$aralkoxy, $C_7$-$C_{25}$aralkoxy which is substituted by E, or —CO—$R^{28}$, $R^{68}$, $R^{69}$, $R^{78}$, $R^{79}$, $R^{88}$ and $R^{89}$ are independently of each other $C_1$-$C_{18}$ alkyl, $C_1$-$C_{24}$alkyl which is substituted by $C_1$-$C_{24}$alkoxy which is substituted by E and/or interrupted by D, or $C_7$-$C_{25}$aralkyl, or $R^{68}$ and $R^{69}$, $R^{78}$ and $R^{79}$, and/or $R^{88}$ and $R^{89}$ form a five- or six-membered ring, or $R^{68}$ and $R^{70}$, $R^{69}$ and $R^{73}$, $R^{77}$ and $R^{78}$ and/or $R^{84}$ and $R^{89}$ are a group

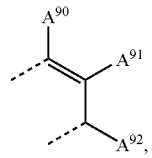

D is —CO—; —COO—; —S—; —SO—; —SO$_2$—; —O—; —NR$^{25}$—; —SiR$^{30}$R$^{31}$—; —POR$^{32}$—; —CR$^{23}$=CR$^{24}$—; or —C≡C—; and E is —OR$^{29}$; —SR$^{29}$; —NR$^{25}$R$^{26}$; —COR$^{28}$; —COOR$^{27}$; —CONR$^{25}$R$^{26}$; —CN; —OCOOR$^{27}$; or halogen; wherein $R^{23}$, $R^{24}$, $R^{25}$ and $R^{26}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—; or $R^{25}$ and $R^{26}$ together form a five or six membered ring, $R^{27}$ and $R^{28}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—, $R^{29}$ is H; $C_6$-$C_{18}$aryl; $C_6$-$C_{18}$aryl, which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—, $R^{30}$ and $R^{31}$ are independently of each other $C_1$-$C_{24}$alkyl, $C_6$-$C_{18}$aryl, or $C_6$-$C_{18}$aryl, which is substituted by $C_1$-$C_{24}$alkyl, and $R^{32}$ is $C_1$-$C_{24}$alkyl, $C_6$-$C_{18}$aryl, or $C_6$-$C_{18}$aryl, which is substituted by $C_1$-$C_{24}$alkyl.

2. An electroluminescent device according to claim 1, comprising a 2H-benzotriazole compound of the formula

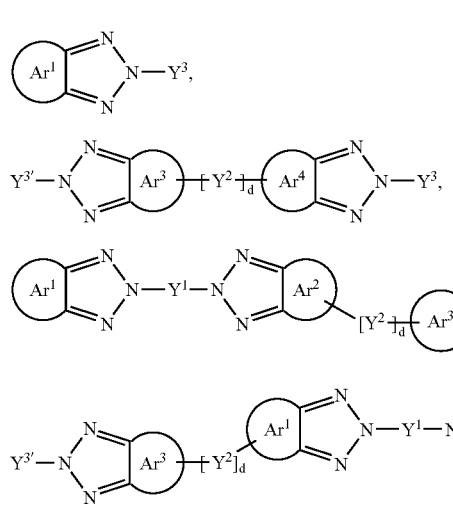

E and/or interrupted by D, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, d, $Ar^1$, $Ar^2$, $Ar^3$, $Y^3$, $Y^{3'}$, $Y^1$ and $Y^2$ are defined as in claim 1 and $Ar^4$ stand for $C_6$-$C_{30}$aryl or a $C_2$-$C_{26}$heteroaryl, which can optionally be substituted.

3. An electroluminescent device according to claim 2, wherein

 and in formula II are independently of each other a group of formula

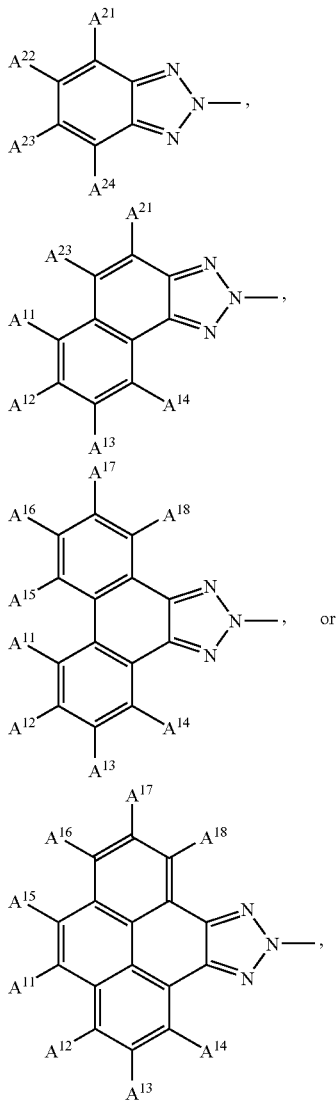

wherein
$A^{21}, A^{22}, A^{23}, A^{24}, A^{11}, A^{12}, A^{13}, A^{14}, A^{15}, A^{16}, A^{17}$ and $A^{18}$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_5$-$C_{12}$cycloalkyl, $C_5$-$C_{12}$cycloalkyl which is substituted by E and/or interrupted by S—, —O—, or —NR$^{25}$—, —NR$^{25}$R$^{26}$, $C_1$-$C_{24}$alkylthio, —PR$^{32}$, R$^{32}$, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by E, $C_7$-$C_{25}$aralkoxy, $C_7$-$C_{25}$aralkoxy which is substituted by E, or —CO—R$^{28}$, or $A^{22}$ and $A^{23}$ or $A^{11}$ and $A^{23}$ are a group

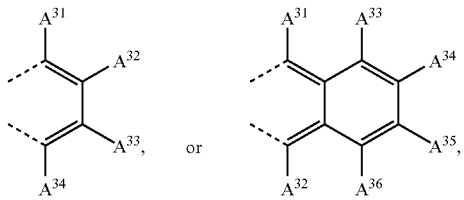

two groups $A^{11}, A^{12}, A^{13}, A^{14}, A^{15}, A^{16}, A^{17}$ and $A^{18}$, which are neighbouring to each other, are a group

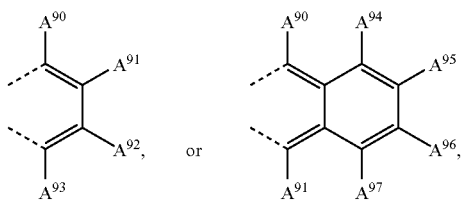

wherein $A^{31}, A^{32}, A^{33}, A^{34}, A^{35}, A^{36}$ and $A^{37}$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_5$-$C_{12}$cycloalkyl, $C_5$-$C_{12}$cycloalkyl which is substituted by E and/or interrupted by S—, —O—, or —NR$^{25}$—, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by E, $C_7$-$C_{25}$aralkoxy, $C_7$-$C_{25}$aralkoxy which is substituted by E, or —CO—R$^{28}$, D is —CO—; —COO—; —S—; —SO—; —SO$_2$—; —O—; —NR$^{25}$—; —SiR$^{30}$R$^{31}$—; —POR$^{32}$—; —CR$^{23}$=CR$^{24}$—; or —C≡C—; and
E is —OR$^{29}$; —SR$^{29}$; —NR$^{25}$R$^{26}$; —COR$^{28}$; —COOR$^{27}$; —CONR$^{25}$R$^{26}$; —CN; —OCOOR$^{27}$; or halogen;
wherein
R$^{23}$, R$^{24}$, R$^{25}$ and R$^{26}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—; or
R$^{25}$ and R$^{26}$ together form a five or six membered ring,
R$^{27}$ and R$^{28}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—,
R$^{29}$ is H; $C_6$-$C_{18}$aryl; $C_6$-$C_{18}$aryl, which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—,
R$^{30}$ and R$^{31}$ are independently of each other $C_1$-$C_{24}$alkyl, $C_6$-$C_{18}$aryl, or $C_6$-$C_{18}$aryl, which is substituted by $C_1$-$C_{24}$alkyl, and
R$^{32}$ is $C_1$-$C_{24}$alkyl, $C_6$-$C_{18}$aryl, or $C_6$-$C_{18}$aryl, which is substituted by $C_1$-$C_{24}$alkyl.

4. An electroluminescent device according to claim 2, wherein

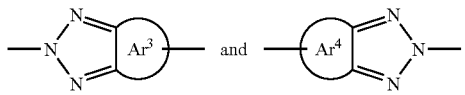

in formula IV are independently of each other a group of formula

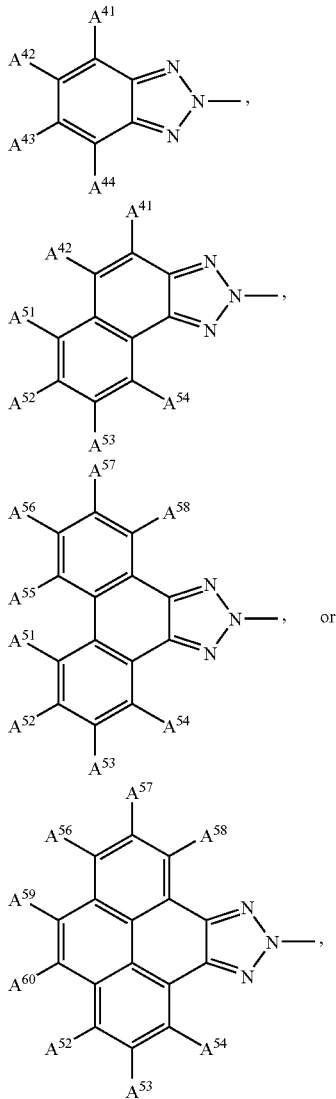

wherein $A^{41}, A^{42}, A^{43}, A^{44}, A^{51}, A^{52}, A^{53}, A^{54}, A^{55}, A^{56}, A^{57}, A^{58}, A^{59}$ and $A^{60}$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_5$-$C_{12}$cycloalkyl, $C_5$-$C_{12}$cycloalkyl which is substituted by E and/or interrupted by S—, —O—, or —NR$^{25}$—, NR$^{25}$R$^{26}$, $C_1$-$C_{24}$alkylthio, —PR$^{32}$R$^{32}$, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by E, $C_7$-$C_{25}$aralkoxy, $C_7$-$C_{25}$aralkoxy which is substituted by E, or —CO—R$^{28}$, or $A^{42}$ and $A^{43}$ or $A^{42}$ and $A^{51}$ are a group

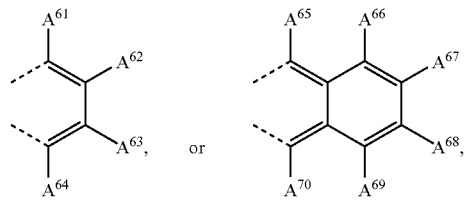

two groups $A^{51}, A^{52}, A^{53}, A^{54}, A^{55}, A^{56}, A^{57}, A^{58}, A^{59}$ and $A^{60}$, which are neighbouring to each other, are a group

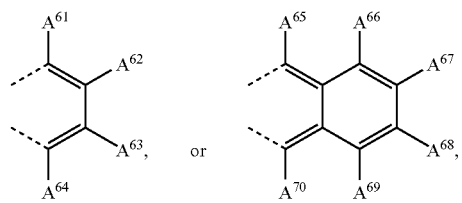

wherein $A^{61}, A^{62}, A^{63}, A^{64}, A^{65}, A^{66}, A^{67}, A^{68}, A^{69}$ and $A^{70}$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_5$-$C_{12}$cycloalkyl, $C_5$-$C_{12}$cycloalkyl which is substituted by E and/or interrupted by S—, —O—, or —NR$^{25}$—, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by E, $C_7$-$C_{25}$aralkoxy, $C_7$-$C_{25}$aralkoxy which is substituted by E, or —CO—R$^{28}$, D is —CO—; —COO—; —S—; —SO—; —SO$_2$—; —O—; —NR$^{25}$—; —SiR$^{30}$R$^{31}$—; —POR$^{32}$—; —CR$^{23}$=CR$^{24}$—; or —C≡C—; and E is —OR$^{29}$; —SR$^{29}$; —NR$^{25}$R$^{26}$; —COR$^{28}$; —COOR$^{27}$; —CONR$^{25}$R$^{26}$; —CN; —OCOOR$^{27}$; or halogen;

wherein $R^{23}, R^{24}, R^{25}$ and $R^{26}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—; or $R^{25}$ and $R^{26}$ together form a five or six membered ring, $R^{27}$ and $R^{28}$ are independently of each other H; $C_6$-$C_{18}$aryl; $C_6$-$C_{18}$aryl which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—, $R^{29}$ is H; $C_6$-$C_{18}$aryl; $C_6$-$C_{18}$aryl, which is substituted by $C_1$-$C_{24}$alkyl, or $C_1$-$C_{24}$alkoxy; $C_1$-$C_{24}$alkyl; or $C_1$-$C_{24}$alkyl which is interrupted by —O—, $R^{30}$ and $R^{31}$ are independently of each other $C_1$-$C_{24}$alkyl, $C_6$-$C_{18}$aryl, or $C_6$-$C_{18}$aryl, which is substituted by $C_1$-$C_{24}$alkyl, and $R^{32}$ is $C_1$-$C_{24}$alkyl, $C_6$-$C_{18}$aryl, or $C_6$-$C_{18}$aryl, which is substituted by $C_1$-$C_{24}$alkyl, wherein one of the substituents $A^{41}, A^{42}, A^{43}, A^{44}, A^{51}, A^{52}, A^{53}, A^{54}, A^{55}, A^{56}, A^{57}, A^{58}, A^{59}, A^{60}, A^{61}, A^{62}, A^{63}, A^{64}, A^{65}, A^{66}, A^{67}, A^{68}, A^{69}$ and $A^{70}$ represents a single bond.

5. An electroluminescent device according to claim 2, wherein the 2H-benzotriazole compound is a compound of formula

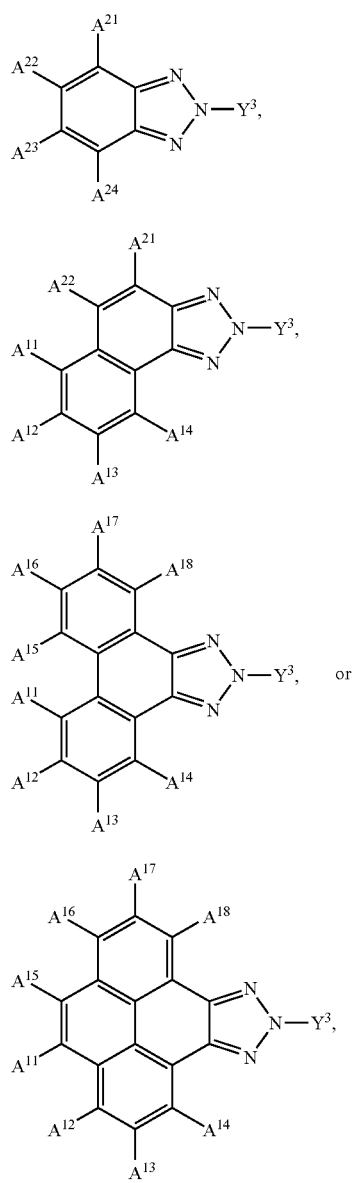

(IIa)

(IIb)

(IIc)

(IId)

$A^{21}, A^{22}, A^{23}$ and $A^{24}$ are independently of each other hydrogen, halogen, $C_1$-$C_{24}$alkyl, $C_1$-$C_{24}$perfluoroalkyl, $C_6$-$C_{18}$aryl, —NR$^{25}$R$^{26}$, —CONR$^{25}$R$^{26}$, or —COOR$^{27}$, or $C_2$-$C_{10}$heteroaryl, or $A^{22}$ and $A^{23}$ or $A^{11}$ and $A^{23}$ are a group of formula

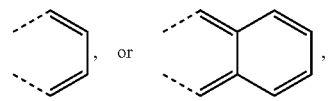

$A^{11}, A^{12}, A^{13}, A^{14}, A^{15}, A^{16}, A^{17}$, and $A^{18}$ are independently of each other H, CN, $C_1$-$C_{24}$alkyl, $C_1$-$C_{24}$alkoxy, $C_1$-$C_{24}$alkylthio, $C_6$-$C_{18}$aryl, —NR$^{25}$R$^{26}$, —CONR$^{25}$R$^{26}$, or —COOR$^{27}$, or $C_2$-$C_{10}$heteroaryl, wherein $R^{25}$ and $R^{26}$ are independently of each other H, $C_6$-$C_{18}$aryl, $C_7$-$C_{18}$aralkyl, or $C_1$-$C_{24}$alkyl, $R^{27}$ is $C_1$-$C_{24}$alkyl, and $Y^3$ is a group of formula

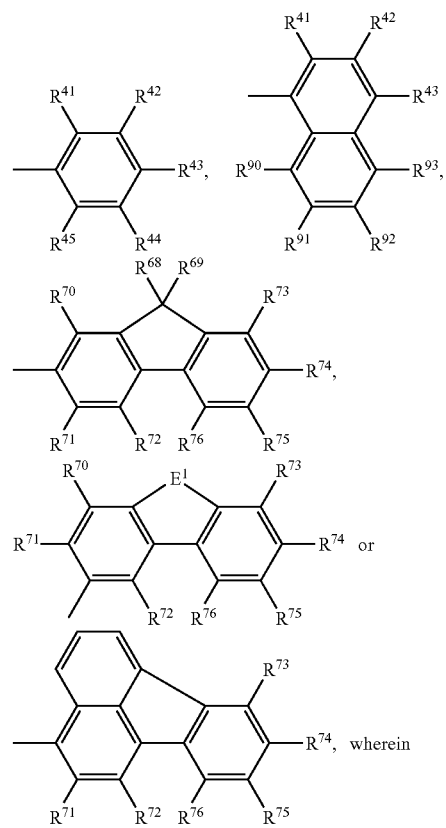

wherein $R^{41}$ is hydrogen, $C_1$-$C_{24}$alkoxy, or OC$_7$-$C_{18}$aralkyl, $R^{42}$ is hydrogen, or $C_1$-$C_{24}$alkyl, $R^{43}$ is hydrogen, halogen, —CONR$^{25}$R$^{26}$, —COOR$^{27}$,

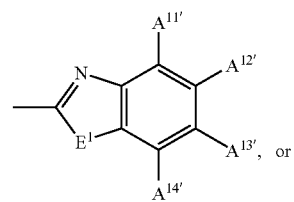

, or

-continued

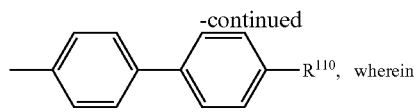, wherein $E^1$ is —S—, —O—, or —NR$^{25'}$—, wherein R$^{25'}$ is $C_1$-$C_{24}$alkyl, or $C_6$-$C_{10}$aryl, R$^{110}$ is H, CN, $C_1$-$C_{24}$alkyl, $C_1$-$C_{24}$alkoxy, $C_1$-$C_{24}$alkylthio, —NR$^{25}$R$^{26}$, —CONR$^{25}$R$^{26}$, or —COOR$^{27}$, or R$^{42}$ and R$^{43}$ are a group of formula

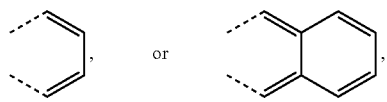

R$^{44}$ is hydrogen, or $C_1$-$C_{24}$alkyl,
R$^{45}$ is hydrogen, or $C_1$-$C_{24}$alkyl,
A$^{11'}$, A$^{12'}$, A$^{13'}$, and A$^{14'}$ are independently of each other H, CN, $C_1$-$C_{24}$alkyl, $C_1$-$C_{24}$alkoxy, $C_1$-$C_{24}$alkylthio, —NR$^{25}$R$^{26}$, —CONR$^{25}$R$^{26}$, or —COOR$^{27}$,
R$^{68}$ and R$^{69}$ are independently of each other $C_1$-$C_{24}$alkyl, which can be interrupted by one or two oxygen atoms,
R$^{70}$, R$^{71}$, R$^{72}$, R$^{73}$, R$^{74}$, R$^{75}$, R$^{76}$, R$^{90}$, R$^{91}$, R$^{92}$, and R$^{93}$ are independently of each other H, CN, $C_1$-$C_{24}$alkyl, $C_6$-$C_{10}$aryl, $C_1$-$C_{24}$alkoxy, $C_1$-$C_{24}$alkylthio, —NR$^{25}$R$^{26}$, —CONR$^{25}$R$^{26}$, or —COOR$^{27}$,
R$^{25}$ and R$^{26}$ are independently of each other H, $C_6$-$C_{18}$aryl, $C_7$-$C_{18}$aralkyl, or $C_1$-$C_{24}$alkyl, and R$^{27}$ is $C_1$-$C_{24}$alkyl.

6. An electroluminescent device according to claim 2, wherein the 2H-benzotriazole compound is a compound of formula

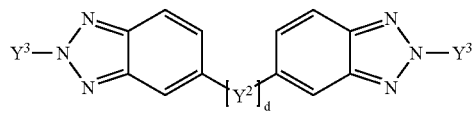

(VIa), wherein d is 0, or 1,
Y$^2$ is a group of formula —O—, —S—, —NR$^{25}$—,

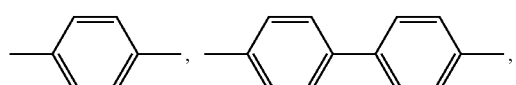

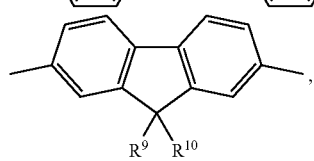

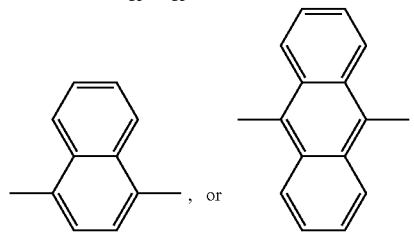

Y$^3$ is a group of formula

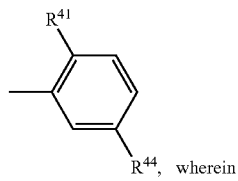, wherein

R$^9$ and R$^{10}$ are independently of each other $C_1$-$C_{24}$alkyl, which can be interrupted by one or two oxygen atoms,
R$^{25}$ is H, $C_6$-$C_{18}$aryl, $C_7$-$C_{18}$aralkyl, or $C_1$-$C_{24}$alkyl,
R$^{41}$ is $C_1$-$C_{24}$alkoxy, or $C_7$-$C_{15}$phenylalkoxy, and
R$^{44}$ is is H, or $C_1$-$C_{24}$alkyl.

7. A 2H-benzotriazole compound of the formula

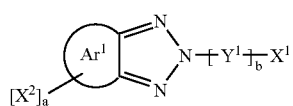 (I)

a is 0, or 1,
b is 0, or 1,
with the proviso that if b is 1, then a is 1.
X$^1$ is a group of formula

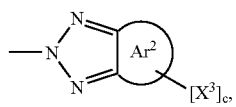

or Y$^3$, if b is 0,
wherein
c is 0, or 1
X$^2$ and X$^3$ are independently of each other a group of formula

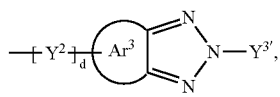, wherein d is 0, or 1,
Ar$^1$, Ar$^2$, and Ar$^3$ are independently of each other $C_6$-$C_{30}$aryl or a $C_2$-$C_{26}$heteroaryl, which can optionally be substituted,
Y$^1$ and Y$^2$ are independently of each other a divalent linking group selected from the group consisting of

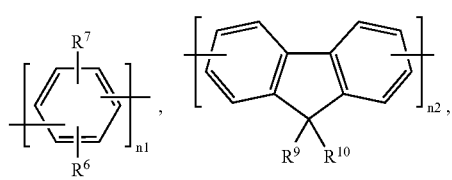

-continued

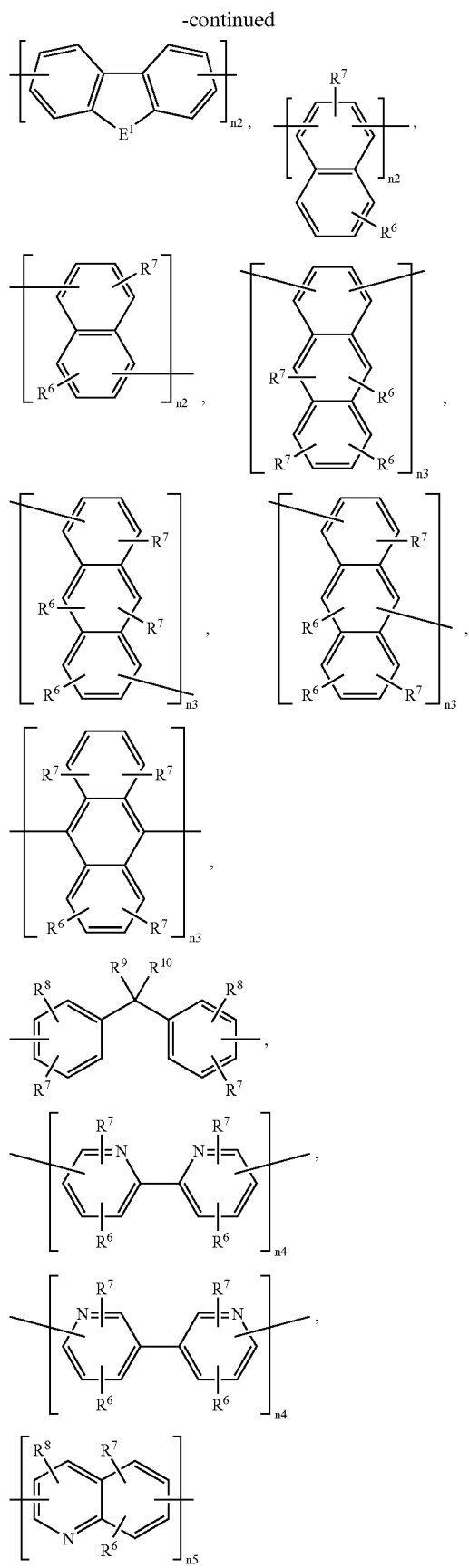

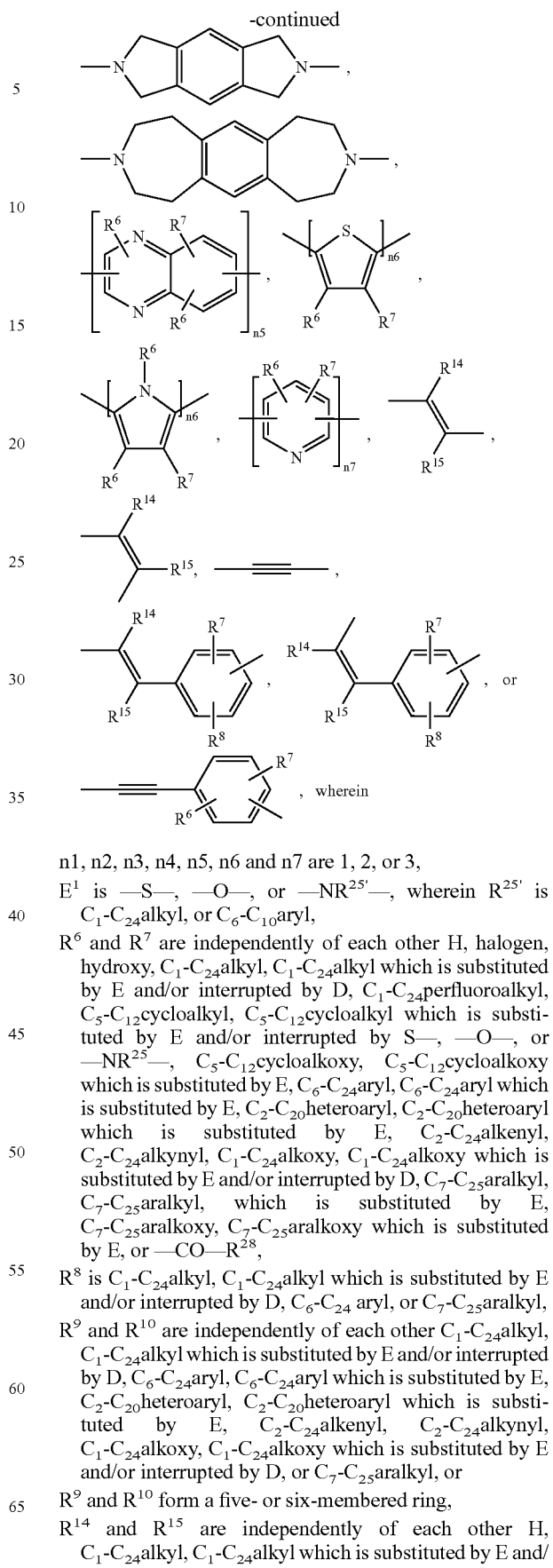

, wherein n1, n2, n3, n4, n5, n6 and n7 are 1, 2, or 3, $E^1$ is —S—, —O—, or —NR$^{25'}$—, wherein R$^{25'}$ is $C_1$-$C_{24}$alkyl, or $C_6$-$C_{10}$aryl, $R^6$ and $R^7$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_5$-$C_{12}$cycloalkyl, $C_5$-$C_{12}$cycloalkyl which is substituted by E and/or interrupted by S—, —O—, or —NR$^{25}$—, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by E, $C_7$-$C_{25}$aralkoxy, $C_7$-$C_{25}$aralkoxy which is substituted by E, or —CO—R$^{28}$, $R^8$ is $C_1$-$C_{24}$alkyl, $C_1$-$C_{24}$alkyl which is substituted by E and/or interrupted by D, $C_6$-$C_{24}$ aryl, or $C_7$-$C_{25}$aralkyl, $R^9$ and $R^{10}$ are independently of each other $C_1$-$C_{24}$alkyl, $C_1$-$C_{24}$alkyl which is substituted by E and/or interrupted by D, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, or $C_7$-$C_{25}$aralkyl, or $R^9$ and $R^{10}$ form a five- or six-membered ring, $R^{14}$ and $R^{15}$ are independently of each other H, $C_1$-$C_{24}$alkyl, $C_1$-$C_{24}$alkyl which is substituted by E and/ or interrupted by D, $C_6$-$C_{24}$aryl, $C_6$-$C_{24}$aryl which is substituted by E, $C_2$-$C_{20}$heteroaryl, or $C_2$-$C_{20}$heteroaryl which is substituted by E, D is —CO—, —COO—, —S—, —SO—, —SO$_2$—, —O—, —NR$^{25}$—, —SiR$^{30}$R$^{31}$—, —POR$^{32}$—, —CR$^{23}$=CR$^{24}$—, or —C≡C—, and E is —OR$^{29}$, —SR$^{29}$, —NR$^{25}$R$^{26}$, —COR$^{28}$, —COOR$^{27}$, —CONR$^{25}$R$^{26}$, —CN, —OCOOR$^{27}$, or halogen, wherein $R^{23}$, $R^{24}$, $R^{25}$ and $R^{26}$ are independently of each other H, $C_6$-$C_{18}$aryl, $C_6$-$C_{18}$aryl which is substituted by $C_1$-$C_{24}$alkyl, $C_1$-$C_{24}$alkoxy, $C_1$-$C_{24}$alkyl, or $C_1$-$C_{24}$alkyl which is interrupted by —O—, or $R^{25}$ and $R^{26}$ together form a five or six membered ring, $R^{27}$ and $R^{28}$ are independently of each other H, $C_6$-$C_{18}$aryl, $C_6$-$C_{18}$aryl which is substituted by $C_1$-$C_{24}$alkyl, or $C_1$-$C_{24}$alkoxy, $C_1$-$C_{24}$alkyl, or $C_1$-$C_{24}$alkyl which is interrupted by —O—, $R^{29}$ is H, $C_6$-$C_{18}$aryl, $C_6$-$C_{18}$aryl, which is substituted by $C_1$-$C_{24}$alkyl, $C_1$-$C_{24}$alkoxy, $C_1$-$C_{24}$alkyl, or $C_1$-$C_{24}$alkyl which is interrupted by —O—, $R^{30}$ and $R^{31}$ are independently of each other $C_1$-$C_{24}$alkyl, $C_6$-$C_{18}$aryl, or $C_6$-$C_{18}$aryl, which is substituted by $C_1$-$C_{24}$alkyl, and $R^{32}$ is $C_1$-$C_{24}$alkyl, $C_6$-$C_{18}$aryl, or $C_6$-$C_{18}$aryl, which is substituted by $C_1$-$C_{24}$alkyl, and $Y^3$ and $Y^{3'}$ are independently of each other a group of formula

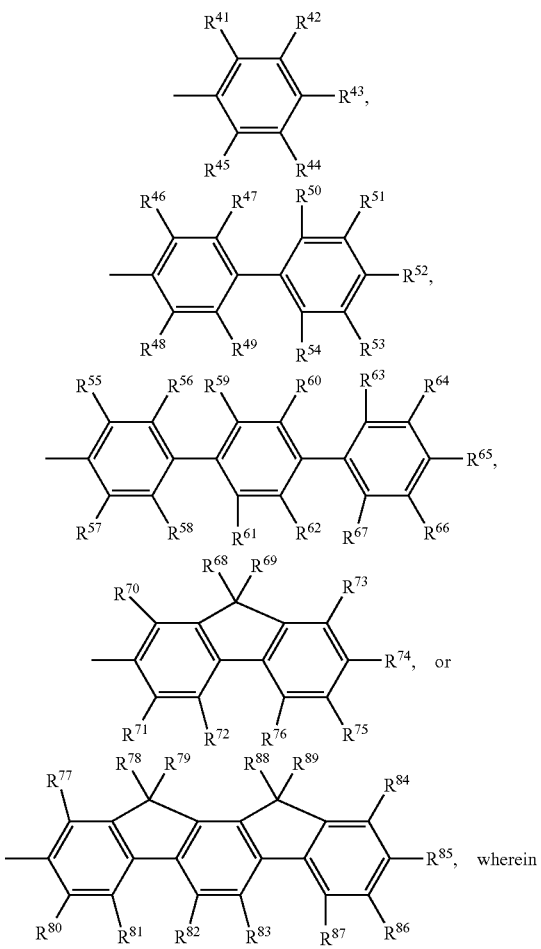

$R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{70}$, $R^{71}$, $R^{72}$, $R^{73}$, $R^{74}$, $R^{75}$, $R^{76}$, $R^{77}$, $R^{80}$, $R^{81}$, $R^{82}$, $R^{83}$, $R^{84}$, $R^{85}$, $R^{86}$, and $R^{87}$ are independently of each other H, $C_1$-$C_{24}$alkyl, which is optionally substituted by E and/or interrupted by D, $C_1$-$C_{24}$alkenyl, which is optionally substituted by E, $C_5$-$C_{12}$cycloalkyl, which is optionally substituted by E, $C_5$-$C_{12}$cycloalkoxy, which is optionally substituted by E, $C_6$-$C_{18}$aryl, which is optionally substituted by E, $C_1$-$C_{24}$alkoxy, which is optionally substituted by E and/or interrupted by D, $C_6$-$C_{18}$aryloxy, which is optionally substituted by E, $C_7$-$C_{18}$arylalkoxy, which is optionally substituted by E, $C_1$-$C_{24}$alkylthio, which is optionally substituted by E and/or interrupted by D, $C_1$-$C_{24}$alkylselenium, which is optionally substituted by E and/or interrupted by D, $C_1$-$C_{24}$alkyltellurium, which is optionally substituted by E and/or interrupted by D, $C_2$-$C_{20}$heteroaryl which is substituted by E, or $C_6$-$C_{18}$aralkyl, which is optionally substituted by E, or two groups $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{70}$, $R^{71}$, $R^{72}$, $R^{73}$, $R^{74}$, $R^{75}$, $R^{76}$, $R^{77}$, $R^{80}$, $R^{81}$, $R^{82}$, $R^{83}$, $R^{84}$, $R^{85}$, $R^{86}$, and $R^{87}$, which are neighbouring to each other, are a group

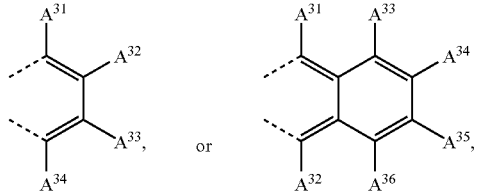

wherein $A^{90}$, $A^{91}$, $A^{92}$, $A^{93}$, $A^{94}$, $A^{95}$, $A^{96}$ and $A^{97}$ are independently of each other H, halogen, hydroxy, $C_1$-$C_{24}$alkyl, $C_1$-$C_{24}$alkyl which is substituted by E and/or interrupted by D, $C_1$-$C_{24}$perfluoroalkyl, $C_5$-$C_{12}$cycloalkyl, $C_5$-$C_{12}$cycloalkyl which is substituted by E and/or interrupted by S—, —O—, or —NR$^{25}$—, $C_5$-$C_{12}$cycloalkoxy, $C_5$-$C_{12}$cycloalkoxy which is substituted by E, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, $C_7$-$C_{25}$aralkyl, $C_7$-$C_{25}$aralkyl, which is substituted by E, $C_7$-$C_{25}$aralkoxy, $C_7$-$C_{25}$aralkoxy which is substituted by E, or —CO—R$^{28}$, $R^{68}$, $R^{69}$, $R^{78}$, $R^{79}$, $R^{88}$ and $R^{89}$ are independently of each other $C_1$-$C_{18}$ alkyl, $C_1$-$C_{24}$alkyl which is substituted by E and/or interrupted by D, $C_6$-$C_{24}$aryl, $C_6$-$C_{24}$aryl which is substituted by E, $C_2$-$C_{20}$heteroaryl, $C_2$-$C_{20}$heteroaryl which is substituted by E, $C_2$-$C_{24}$alkenyl, $C_2$-$C_{24}$alkynyl, $C_1$-$C_{24}$alkoxy, $C_1$-$C_{24}$alkoxy which is substituted by E and/or interrupted by D, or $C_7$-$C_{25}$aralkyl, or $R^{68}$ and $R^{69}$, $R^{78}$ and $R^{79}$, and/or $R^{88}$ and $R^{89}$ form a five- or six-membered ring, or $R^{68}$ and $R^{70}$, $R^{69}$ and $R^{73}$, $R^{77}$ and $R^{78}$ and/or $R^{84}$ and $R^{89}$ are a group

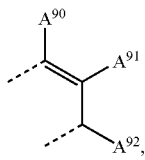

D is —CO—; —COO—; —S—; —SO—; —SO$_2$—; —O—; —NR$^{25}$—; —SiR$^{30}$R$^{31}$—; —POR$^{32}$—; —CR$^{23}$=CR$^{24}$—; or —C≡C—; and E is —OR$^{29}$; —SR$^{29}$; —NR$^{25}$R$^{26}$; —COR$^{28}$; —COOR$^{27}$; —CONR$^{25}$R$^{26}$; —CN; —OCOOR$^{27}$; or halogen; wherein $R^{23}$, $R^{24}$, $R^{25}$ and $R^{26}$ are independently of each other H; C$_6$-C$_{18}$aryl; C$_6$-C$_{18}$aryl which is substituted by C$_1$-C$_{24}$alkyl, or C$_1$-C$_{24}$alkoxy; C$_1$-C$_{24}$alkyl; or C$_1$-C$_{24}$alkyl which is interrupted by —O—; or $R^{25}$ and $R^{26}$ together form a five or six membered ring, $R^{27}$ and $R^{28}$ are independently of each other H; C$_6$-C$_{18}$aryl; C$_6$-C$_{18}$aryl which is substituted by C$_1$-C$_{24}$alkyl, or C$_1$-C$_{24}$alkoxy; C$_1$-C$_{24}$alkyl; or C$_1$-C$_{24}$alkyl which is interrupted by —O—, $R^{29}$ is H; C$_6$-C$_{18}$aryl; C$_6$-C$_{18}$aryl, which is substituted by C$_1$-C$_{24}$alkyl, or C$_1$-C$_{24}$alkoxy; C$_1$-C$_{24}$alkyl; or C$_1$-C$_{24}$alkyl which is interrupted by —O—, $R^{30}$ and $R^{31}$ are independently of each other C$_1$-C$_{24}$alkyl, C$_6$-C$_{18}$aryl, or C$_8$-C$_{18}$aryl, which is substituted by C$_1$-C$_{24}$alkyl, and $R^{32}$ is C$_1$-C$_{24}$alkyl, C$_6$-C$_{18}$aryl, or C$_6$-C$_{18}$aryl, which is substituted by C$_1$-C$_{24}$alkyl.

* * * * *